United States Patent
Faller et al.

(10) Patent No.: US 12,318,107 B2
(45) Date of Patent: *Jun. 3, 2025

(54) HANDPIECE AND BLADE CONFIGURATIONS FOR ULTRASONIC SURGICAL INSTRUMENT

(71) Applicant: Cilag GmbH International, Zug (CH)

(72) Inventors: Craig N. Faller, Batavia, OH (US); Ryan M. Asher, Cincinnati, OH (US); John B. Schulte, West Chester, OH (US); Randal T. Byrum, Mason, OH (US); Jose D. Vasquez, Cincinnati, OH (US); Thomas C. Gallmeyer, Ann Arbor, MI (US); Benjamin M. Boyd, Fairborn, OH (US); Amy L Marcotte, Mason, OH (US); Jacob S. Gee, Cincinnati, OH (US); Jonathan T. Batross, Cincinnati, OH (US); Jeffrey D. Messerly, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 929 days.

This patent is subject to a terminal disclaimer.

(21) Appl. No.: 17/314,677

(22) Filed: May 7, 2021

(65) Prior Publication Data
US 2021/0346048 A1    Nov. 11, 2021

Related U.S. Application Data

(63) Continuation of application No. 15/830,312, filed on Dec. 4, 2017, now Pat. No. 11,103,270, which is a
(Continued)

(51) Int. Cl.
*A61B 17/32* (2006.01)
*A61B 17/29* (2006.01)
(Continued)

(52) U.S. Cl.
CPC ...... *A61B 17/320092* (2013.01); *A61B 17/29* (2013.01); *A61B 17/2909* (2013.01);
(Continued)

(58) Field of Classification Search
CPC .... A61B 17/320092; A61B 17/320068; A61B 2017/320078; A61B 2017/320069;
(Continued)

(56) References Cited

U.S. PATENT DOCUMENTS 5,318,570 A * 6/1994 Hood ................. A61B 17/8847
601/2
5,322,055 A   6/1994 Davison et al.
(Continued)

FOREIGN PATENT DOCUMENTS

DE    9403248 U1    8/1994
DE    29713490 U1   10/1997
(Continued)

OTHER PUBLICATIONS

Brazilian Office Action dated Feb. 19, 2020, for Application No. BR112016011943-6, 4 pages.
(Continued)

*Primary Examiner* — Katherine H Schwiker
(74) *Attorney, Agent, or Firm* — Frost Brown Todd LLP

(57) ABSTRACT

A surgical apparatus comprises a body, an ultrasonic transducer, a shaft, and an end effector. The ultrasonic transducer is operable to convert electrical power into ultrasonic vibrations. The body comprises a pivotal trigger. The shaft couples the end effector and the body together. The end effector comprises a clamp arm and an ultrasonic blade in acoustic communication with the ultrasonic transducer. The ultrasonic blade is operable to deliver ultrasonic vibrations to tissue. Pivotal movement of the trigger causes movement of the clamp arm. The trigger includes a compliant feature
(Continued)

configured to limit the amount of force delivered to tissue by the clamp arm. The flexible feature may comprise a flexible band, living hinge, a series of living hinges, or a flexible tab.

17 Claims, 43 Drawing Sheets

Related U.S. Application Data continuation of application No. 14/090,444, filed on Nov. 26, 2013, now Pat. No. 9,943,325.

(51) Int. Cl.
*A61B 90/00* (2016.01)
*A61B 17/00* (2006.01)

(52) U.S. Cl.
CPC .... *A61B 90/03* (2016.02); *A61B 2017/00367* (2013.01); *A61B 2017/292* (2013.01); *A61B 2017/320069* (2017.08); *A61B 2017/320071* (2017.08); *A61B 2017/320078* (2017.08); *A61B 2017/320089* (2017.08); *A61B 2017/320093* (2017.08); *A61B 2017/320094* (2017.08); *A61B 2017/320095* (2017.08); *A61B 2090/031* (2016.02)

(58) Field of Classification Search
CPC ....... A61B 2017/320071; A61B 2017/320072; A61B 2017/320073; A61B 2017/320074; A61B 2017/320075; A61B 2017/320077; A61B 2017/320082; A61B 2017/320093; A61B 2017/320094; A61B 2017/320095; A61B 2017/320098
See application file for complete search history.

(56) References Cited

U.S. PATENT DOCUMENTS

| | | | |
|---|---|---|---|
| 5,527,313 A | 6/1996 | Scott et al. | |
| 5,562,699 A | 10/1996 | Heimberger et al. | |
| 5,653,721 A | 8/1997 | Knodel et al. | |
| 5,873,873 A | 2/1999 | Smith et al. | |
| 5,980,510 A | 11/1999 | Tsonton et al. | |
| 6,269,178 B1 | 7/2001 | Takeo | |
| 6,280,407 B1 | 8/2001 | Manna et al. | |
| 6,325,811 B1 | 12/2001 | Messerly | |
| 6,423,082 B1 | 7/2002 | Houser et al. | |
| 6,500,188 B2 | 12/2002 | Harper et al. | |
| 6,569,178 B1 | 5/2003 | Miyawaki et al. | |
| 6,660,017 B2 | 12/2003 | Beaupre | |
| 6,773,444 B2 | 8/2004 | Messerly | |
| 6,783,524 B2 | 8/2004 | Anderson et al. | |
| 7,714,481 B2 | 5/2010 | Sakai | |
| 8,025,630 B2 | 9/2011 | Murakami et al. | |
| 8,043,303 B2 | 10/2011 | Razvi et al. | |
| 8,057,498 B2 | 11/2011 | Robertson | |
| 8,409,244 B2 | 4/2013 | Hinman et al. | |
| 8,461,744 B2 | 6/2013 | Wiener et al. | |
| 8,523,889 B2 | 9/2013 | Stulen et al. | |
| 8,591,536 B2 | 11/2013 | Robertson | |
| 8,623,027 B2 | 1/2014 | Price et al. | |
| 8,636,725 B2 | 1/2014 | Amann et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,358,407 B2 | 6/2016 | Akagane | |
| 9,381,058 B2 | 7/2016 | Houser et al. | |
| 9,393,037 B2 | 7/2016 | Olson et al. | |
| 9,872,698 B2 | 1/2018 | Van Tol et al. | |
| 9,943,325 B2 | 4/2018 | Faller et al. | |
| 11,103,270 B2 | 8/2021 | Faller et al. | |
| 2002/0156493 A1* | 10/2002 | Houser | A61B 17/320068 606/169 |
| 2003/0114874 A1* | 6/2003 | Craig | A61B 17/320092 606/169 |
| 2003/0204199 A1 | 10/2003 | Novak et al. | |
| 2003/0212392 A1* | 11/2003 | Fenton | A61B 17/320068 606/28 |
| 2005/0049546 A1* | 3/2005 | Messerly | A61B 17/320092 606/169 |
| 2006/0009790 A1 | 1/2006 | Blake, III et al. | |
| 2006/0079874 A1 | 4/2006 | Faller et al. | |
| 2007/0016236 A1* | 1/2007 | Beaupre | A61B 17/320092 606/169 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0088785 A1 | 4/2009 | Masuda | |
| 2009/0248051 A1* | 10/2009 | Masuda | A61B 18/1445 606/169 |
| 2010/0204721 A1 | 8/2010 | Young et al. | |
| 2011/0022052 A1 | 1/2011 | Jorgensen | |
| 2012/0022583 A1 | 1/2012 | Sugalski et al. | |
| 2012/0116265 A1 | 5/2012 | Houser et al. | |
| 2012/0116391 A1 | 5/2012 | Houser et al. | |
| 2012/0239068 A1 | 9/2012 | Morris et al. | |
| 2013/0204247 A1 | 8/2013 | Triplett | |
| 2014/0031809 A1* | 1/2014 | Takabayashi | A61B 18/18 606/169 |
| 2015/0080924 A1 | 3/2015 | Stulen et al. | |

FOREIGN PATENT DOCUMENTS

| | | | |
|---|---|---|---|
| EP | 2484301 A1 | 8/2012 | |
| JP | H08-38492 A | 2/1996 | |
| JP | 2001-524842 A | 12/2001 | |
| JP | 2010-534523 A | 11/2010 | |
| JP | 2014-516270 A | 7/2014 | |
| WO | WO 2012/129292 A2 | 9/2012 | |
| WO | WO 2014/001200 A1 | 1/2014 | |
| WO | WO 2014/150163 A1 | 9/2014 | |

OTHER PUBLICATIONS

Chinese Search Report dated Mar. 14, 2018, for Application No. 201480064505.2, 2 pages.
Chinese Office Action dated Mar. 23, 2018, for Application No. 201480064505.2, 2 pages.
European Examination Report dated Apr. 21, 2021, for Application No. 14805457.0, 8 pages.
Indian Office Action dated Jan. 29, 2020, for Application No. 201617018139, 8 pages.
International Search Report and Written Opinion dated Apr. 8, 2015, for Application No. PCT/US2014/065626, 19 pages.
Japanese Office Action, Notice of Reasons for Refusal, and First Search, dated Sep. 11, 2018, for Application No. 2016-534217, 18 pages.
Japanese Office Action, Notice of Reasons for Refusal, dated Feb. 19, 2019, for Application No. 2016-534217, 3 pages.
Mexican Office Action, First Substantive Examination Requirement, dated Sep. 23, 2020, for Application No. MX/a/2016/006843, 3 pages.
U.S. Appl. No. 61/410,603, filed Nov. 5, 2010.
U.S. Appl. No. 61/734,636, filed Dec. 7, 2012.

* cited by examiner

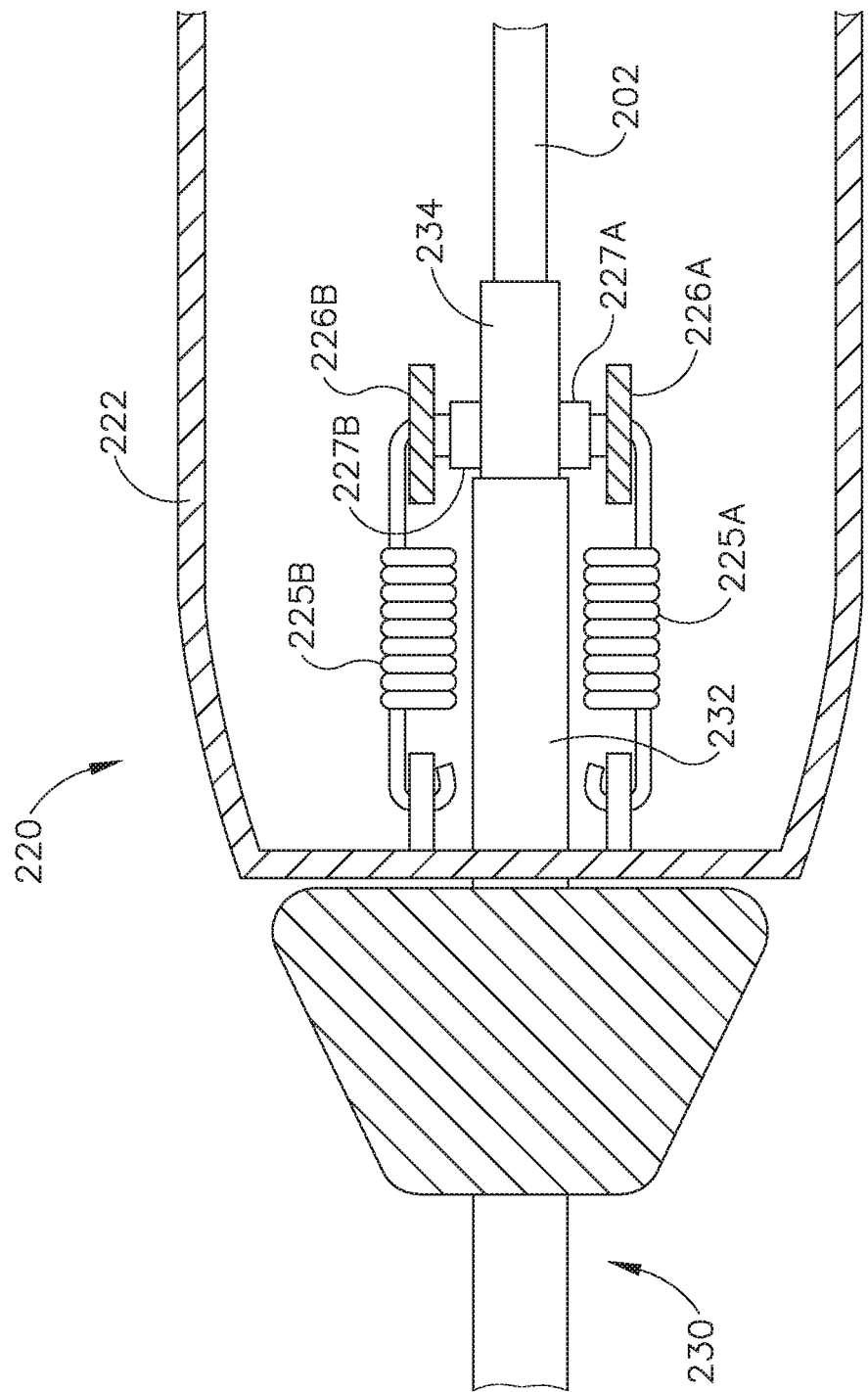

HANDPIECE AND BLADE CONFIGURATIONS FOR ULTRASONIC SURGICAL INSTRUMENT

This application is a continuation of U.S. patent application Ser. No. 15/830,312, entitled "Handpiece and Blade Configurations for Ultrasonic Surgical Instrument," filed Dec. 4, 2017 and published as U.S. Pub. No. 2018/0153574 on Jun. 7, 2018, issued as U.S. Pat. No. 11,103,270 on Aug. 31, 2021, which is a continuation of U.S. patent application Ser. No. 14/090,444, entitled "Handpiece and Blade Configurations for Ultrasonic Surgical Instrument," filed Nov. 26, 2013 and issued as U.S. Pat. No. 9,943,325 on Apr. 17, 2018.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 1, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on July 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," issued as U.S. Pat. No. 9,393,037 on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6A depicts a top view of the instrument of FIG. 5A with the trigger assembly in the first position;

Figure 1:
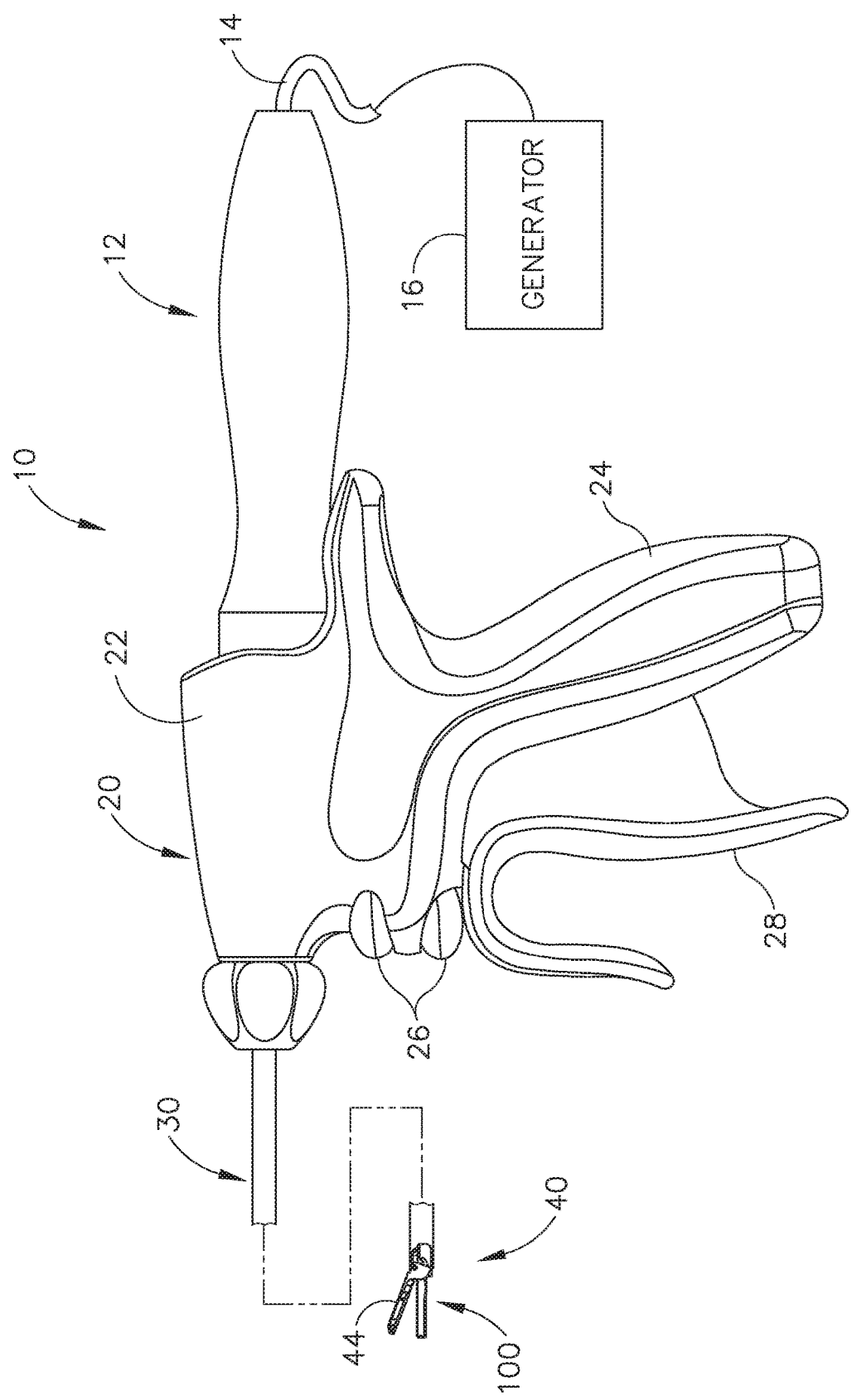
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980, 510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, issued as U.S. Pat. No. 8,623,027 on Jan. 1, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265; U.S. patent application Ser. No. 13/538,588, issued as U.S. Pat. No. 9,393,037 on Jul. 19, 2016; U.S. patent application Ser. No. 13/657,553, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
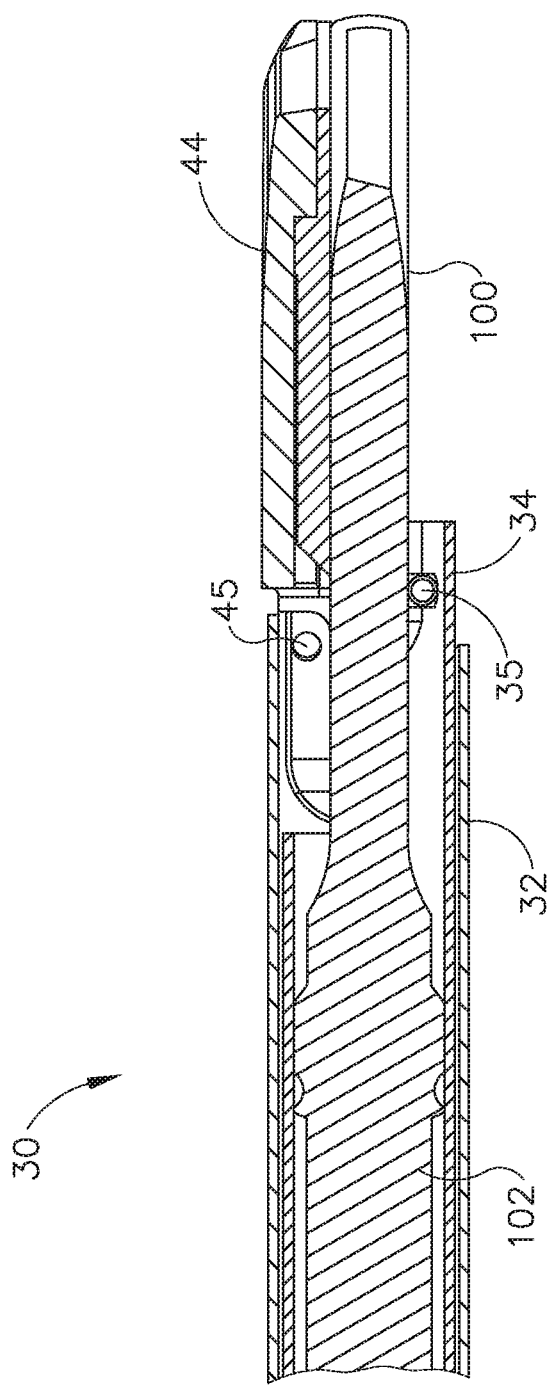
FIG. 2 depicts a side cross-sectional view of an end effector of the instrument of FIG. 1 in a closed position.
Figure 3:
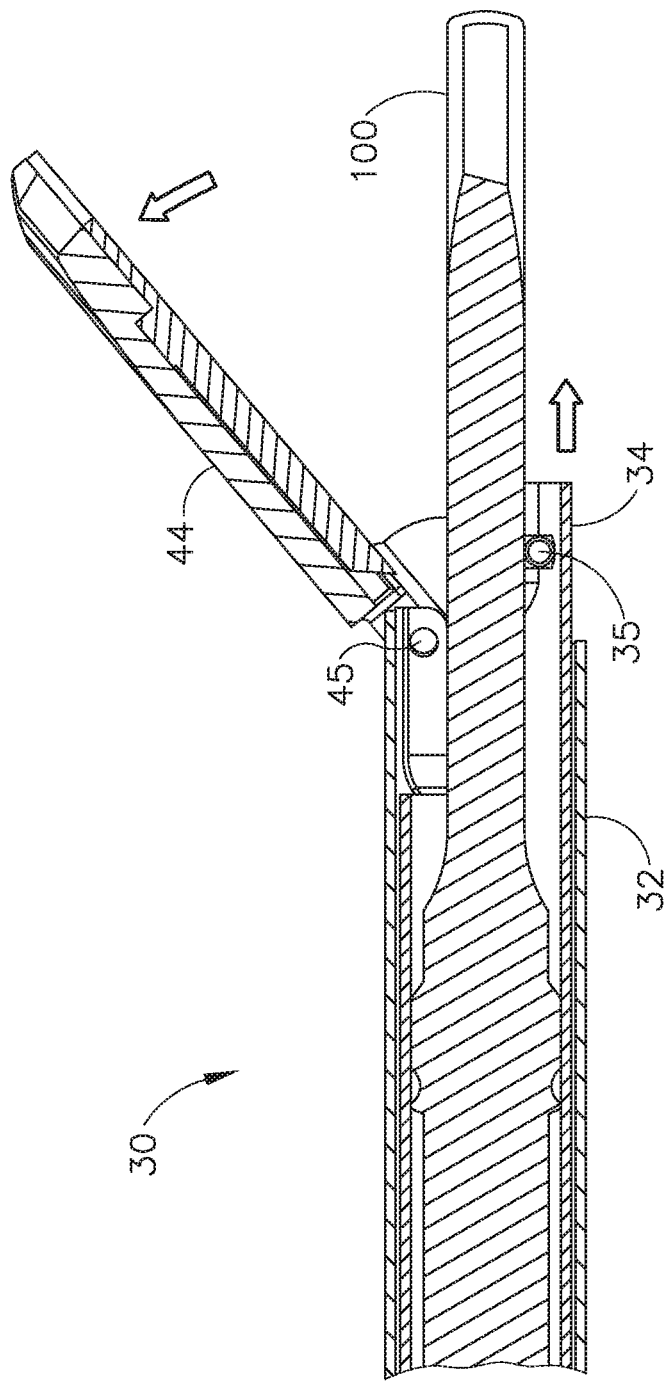
FIG. 3 depicts a side cross-sectional view of an end effector of the instrument of FIG. 1 in an open position.
Figure 4:
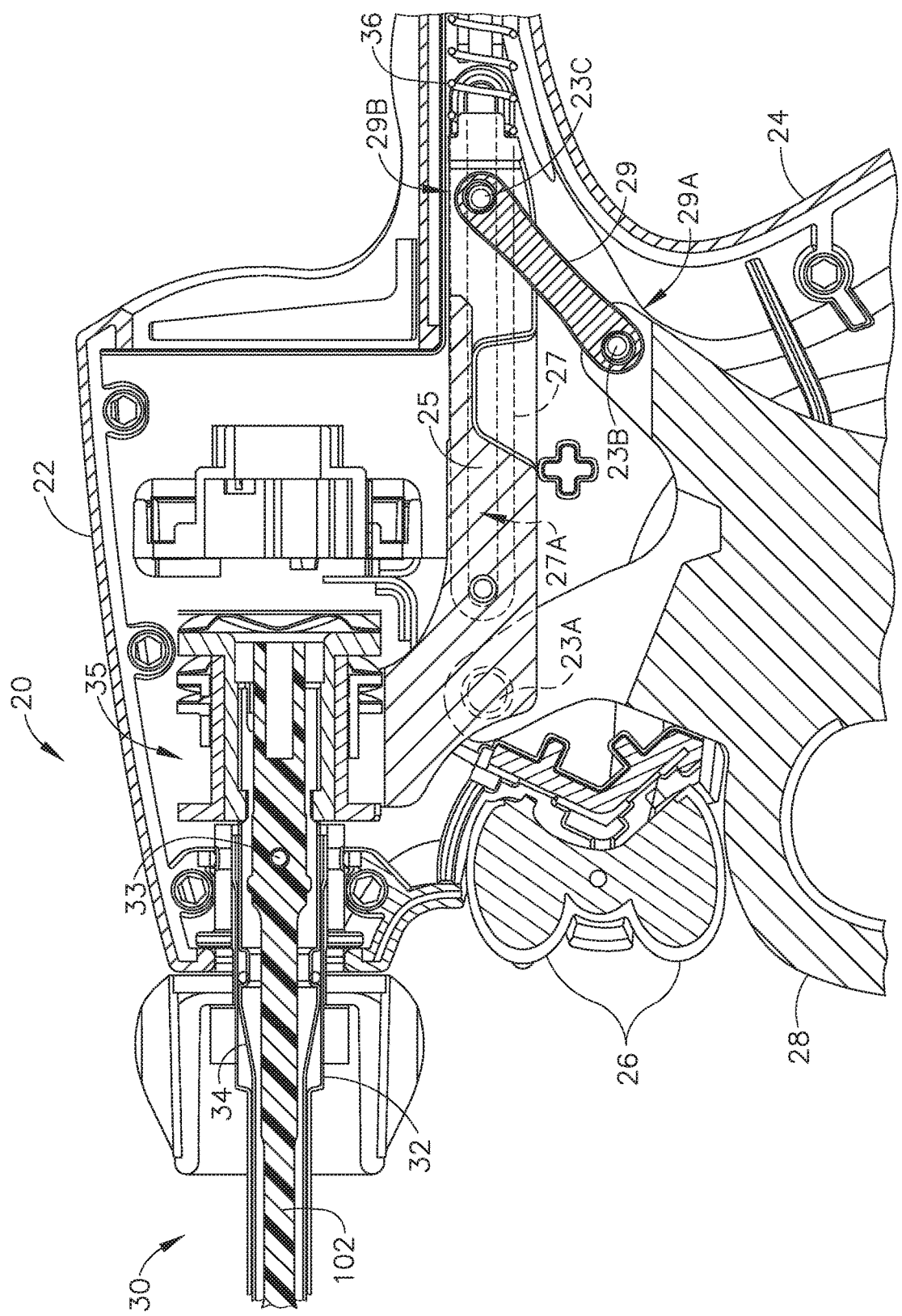
FIG. 4 depicts a cross-sectional view of a handle assembly of the instrument of FIG. 1.

Instrument (10) of the present example comprises a handle assembly (20), a shaft assembly (30), and an end effector (40). As shown in FIGS. 2-4, shaft assembly (30) comprises an outer sheath (32), an inner tube (34) slidably disposed within outer sheath (32), and a waveguide (102) disposed within inner tube (34). As will be discussed in more detail below, longitudinal translation of inner tube (34) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. As shown in FIG. 4, trigger (28) is pivotably coupled to handle assembly (20) via a pin (23A) such that trigger (28) rotates about an axis located below shaft assembly (30).

Trigger (28) is coupled with a yoke (25) via a linkage (29) such that rotation of trigger (28) about pin (23A) causes longitudinal translation of yoke (25). A first end (29A) of linkage (29) is rotatably coupled with a proximal portion of trigger (28) via a pin (23B). A second end (29B) of linkage (29) is rotatably coupled with a proximal portion of yoke (25) via a pin (23C). A pair of elongate oval-shaped projections (27) extend inwardly from interior surfaces of body (22). An interior surface of each oval-shaped projection (27) defines an elongate oval-shaped slot (27A). Pin (23C) passes completely through the proximal portion of yoke (25) and second end (29B) of linkage (29) such that ends of pin (23C) extend from opposite sides of yoke (25). These ends of pin (23C) are slidably and rotatably disposed within oval-shaped slots (27A). A pin (23D) passes completely through a distal portion of yoke (25) such that ends of pin (23D) extend from opposite sides of yoke (25). These ends of pin (23D) are slidably and rotatably disposed within oval-shaped slots (27A). It should therefore be understood that yoke (25) is longitudinally translatable via pins (23C, 23D) within oval-shaped slots (27A) between a proximal longitudinal position and a distal longitudinal position. Furthermore, because the proximal portion of trigger (28) is coupled with yoke (25) via linkage (29), it should be understood that pivoting of trigger (28) toward pistol grip (24) will cause proximal longitudinal translation of yoke (25) within oval-shaped slots (27A); and that pivoting of trigger (28) away from pistol grip (24) will cause distal longitudinal translation of yoke (25) within oval-shaped slots (27A).

A distal portion of yoke (25) is coupled with inner tube (34) of shaft assembly (30) via a coupling assembly (35). As discussed above, inner tube (34) is longitudinally translatable within outer sheath (32), such that inner tube (34) is configured to longitudinally translate concurrently with yoke (25). Furthermore, because pivoting of trigger (28) toward pistol grip (24) causes proximal longitudinal translation of yoke (25), it should be understood that pivoting of trigger (28) toward pistol grip (24) will cause proximal longitudinal translation of inner tube (34) relative to outer sheath (32) and handle assembly (20). Finally, because pivoting of trigger (28) away from pistol grip (24) causes distal longitudinal translation of yoke (25), it should be understood that and that pivoting of trigger (28) away from pistol grip (24) will cause distal longitudinal translation of inner tube (34) relative to outer sheath (32) and handle assembly (20). As shown in FIG. 4, a spring (36) is positioned within a proximal end of body (22) of handle assembly (20). Spring (36) bears against a portion of body (22) and a proximal end of yoke (25) to thereby bias yoke (25) toward the distal position. Biasing of yoke (25) toward the distal position causes inner tube (34) to be biased distally and further causes trigger (28) to be biased away from pistol grip (24).

As shown in FIGS. 2 and 3, end effector (40) includes an ultrasonic blade (00) and a pivoting clamp arm (44). Clamp arm (44) is pivotably coupled with a distal end of outer sheath (32) of shaft assembly (30) above ultrasonic blade (100) via a pin (45). As best seen in FIG. 3, a distal end of inner tube (34) is rotatably coupled with a proximal end of clamp arm (44) below ultrasonic blade (100) via a pin (35) such that longitudinal translation of inner tube (34) causes rotation of clamp arm (44) about pin (45) toward and away from ultrasonic blade (100) to thereby clamp tissue between clamp arm (44) and ultrasonic blade (100) to cut and/or seal the tissue. In particular, proximal longitudinal translation of inner tube (34) relative to outer sheath (32) and handle assembly (20) causes clamp arm (44) to move toward ultrasonic blade (100); and distal longitudinal translation of inner tube (34) relative to outer sheath (32) and handle assembly (20) causes clamp arm (44) to move away from ultrasonic blade (100). It should therefore be understood that pivoting of trigger (28) toward pistol grip (24) will cause clamp arm (44) to move toward ultrasonic blade (100); and that pivoting of trigger (28) away from pistol grip (24) will cause clamp arm (44) to move away from ultrasonic blade (100). In some versions, one or more resilient members are used to bias clamp arm (44) and/or trigger (28) to the open position shown in FIG. 4.

An ultrasonic transducer assembly (12) extends proximally from body (22) of handle assembly (20). While transducer assembly (12) is shown in FIG. 1, transducer assembly (12) is omitted from FIG. 4. Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,989,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (102), which extends through shaft assembly (30) to reach ultrasonic blade (100). Waveguide (102) is secured within shaft assembly (30) via a pin (33), which passes through waveguide (102) and shaft assembly (30). Pin (33) is located at a position along the length of waveguide (102) corresponding to a node associated with resonant ultrasonic vibrations communicated through waveguide (102). As noted above, when ultrasonic blade (100) is in an activated state (i.e., vibrating ultrasonically), ultrasonic blade (100) is operable to effectively cut through and seal tissue, particularly when the tissue is being clamped between clamp arm (44) and ultrasonic blade (100). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of ultrasonic blade (100) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (12) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide (102) to reach ultrasonic blade (100), thereby providing oscillation of ultrasonic blade (100) at the resonant ultrasonic frequency. Thus, when tissue is secured between ultrasonic blade (100) and clamp arm (44), the ultrasonic oscillation of ultrasonic blade (100) may simultaneously sever the tissue and denature the proteins in adjacent tissue cells, thereby providing a coagulative effect with relatively little thermal spread. In some versions, an electrical current may also be provided through ultrasonic blade (100) and clamp arm (44) to also seal the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively activate transducer assembly (12) to activate ultrasonic blade (100). In the present example, two buttons (26) are provided—one for activating ultrasonic blade (100) at a low power and another for activating ultrasonic blade (100) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265; U.S. patent application Ser. No. 13/538,588, issued as U.S. Pat. No. 9,393,037 on Jul. 19, 2016; and/or U.S. patent application Ser. No. 13/657,553, issued as U.S. Pat. No. 9,095,367 on Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

II. Exemplary Trigger Assembly with Upper Pivot and Spring

Although trigger (28) of instrument (10) discussed above rotates about an axis located below shaft assembly (30), in some versions of instrument (10), the axis about which trigger (28) rotates may be located above shaft assembly (30). FIGS. 5A-7 show such an instrument (210) having a trigger (228) that rotates about an axis located above a shaft assembly (230). Instrument (210) of the present example is configured to operate substantially similar to instrument (10) discussed above except for the differences discussed below. In particular, instrument (210) is configured to clamp tissue between a pivoting clamp arm (244) and an ultrasonic blade (201) to thereby cut and/or seal the tissue.

Figure 5A:
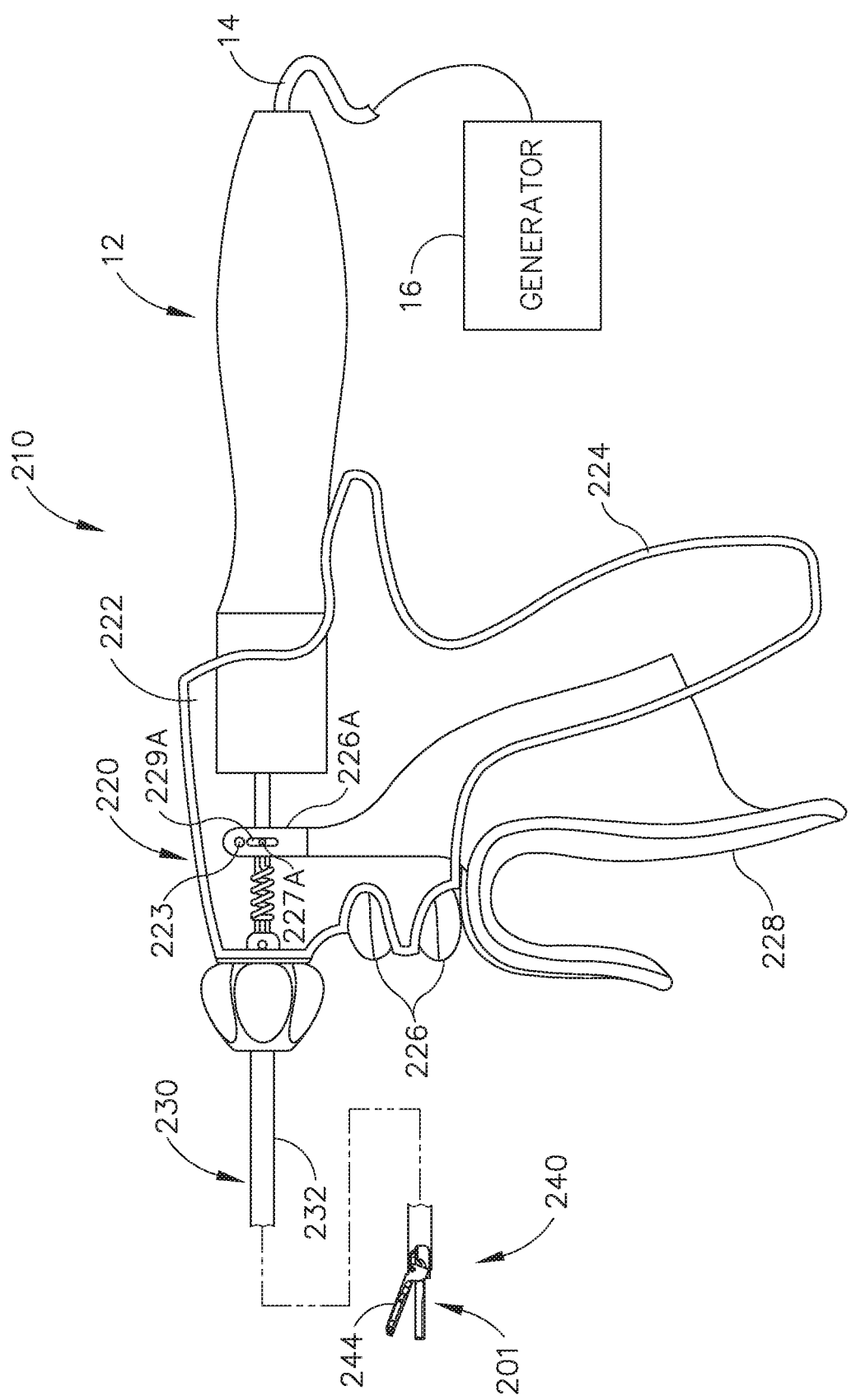
FIG. 5A depicts a side elevational view of a variation of the instrument of FIG. 1 with an exemplary alternative trigger assembly in a first position.
Figure 5B:
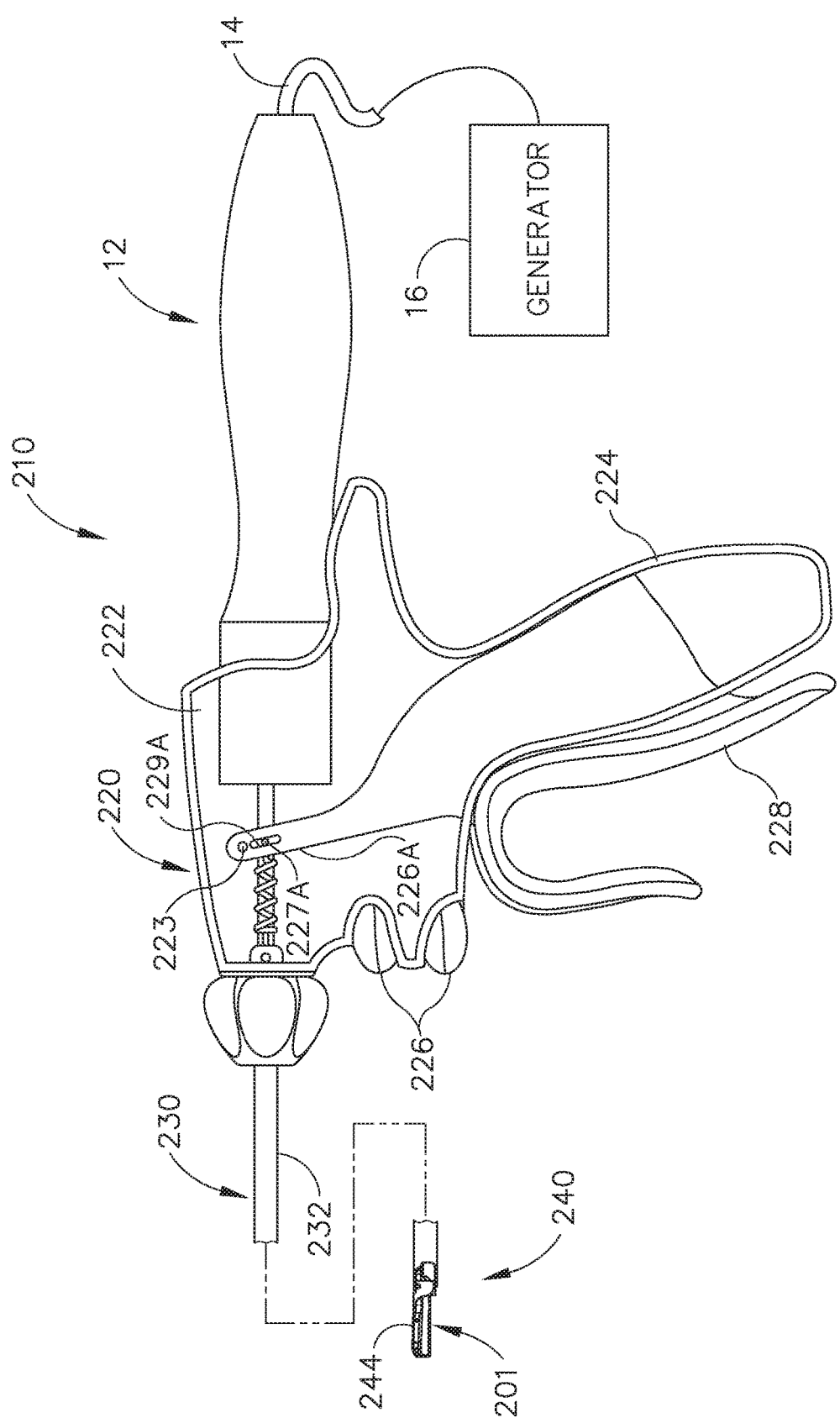
FIG. 5B depicts a side elevational view of the instrument of FIG. 5A with the trigger assembly moved into a second position.
Figure 6B:
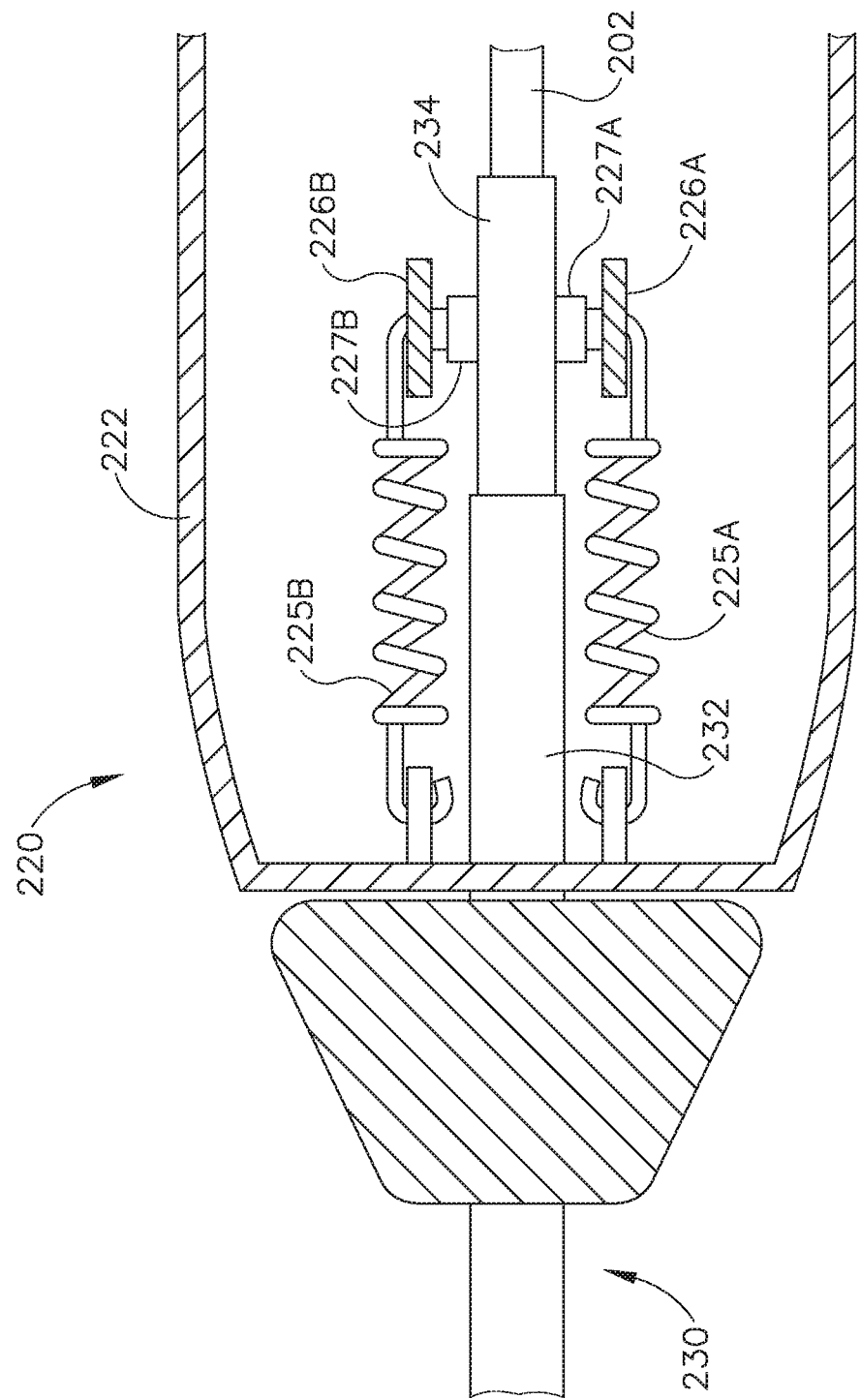
FIG. 6B depicts a top view of the instrument of FIG. 5A with the trigger assembly moved to the second position.

Instrument (210) of the present example comprises a handle assembly (220), shaft assembly (230), and an end effector (240). Shaft assembly (230) comprises an outer sheath (232), an inner tube (234) slidably disposed within outer sheath (232), and a waveguide (202) disposed within inner tube (234). As will be discussed in more detail below, longitudinal translation of inner tube (234) causes actuation of clamp arm (244) of end effector (240). Handle assembly (220) comprises a body (222) including a pistol grip (224) and a pair of buttons (226). Handle assembly (220) also includes a trigger (228) that is pivotable toward and away from pistol grip (224). As shown in FIGS. 5A and 5B, trigger (228) is pivotably coupled to handle assembly (220) via a pin (223) such that trigger (228) rotates about an axis located above shaft assembly (230).

Figure 7:
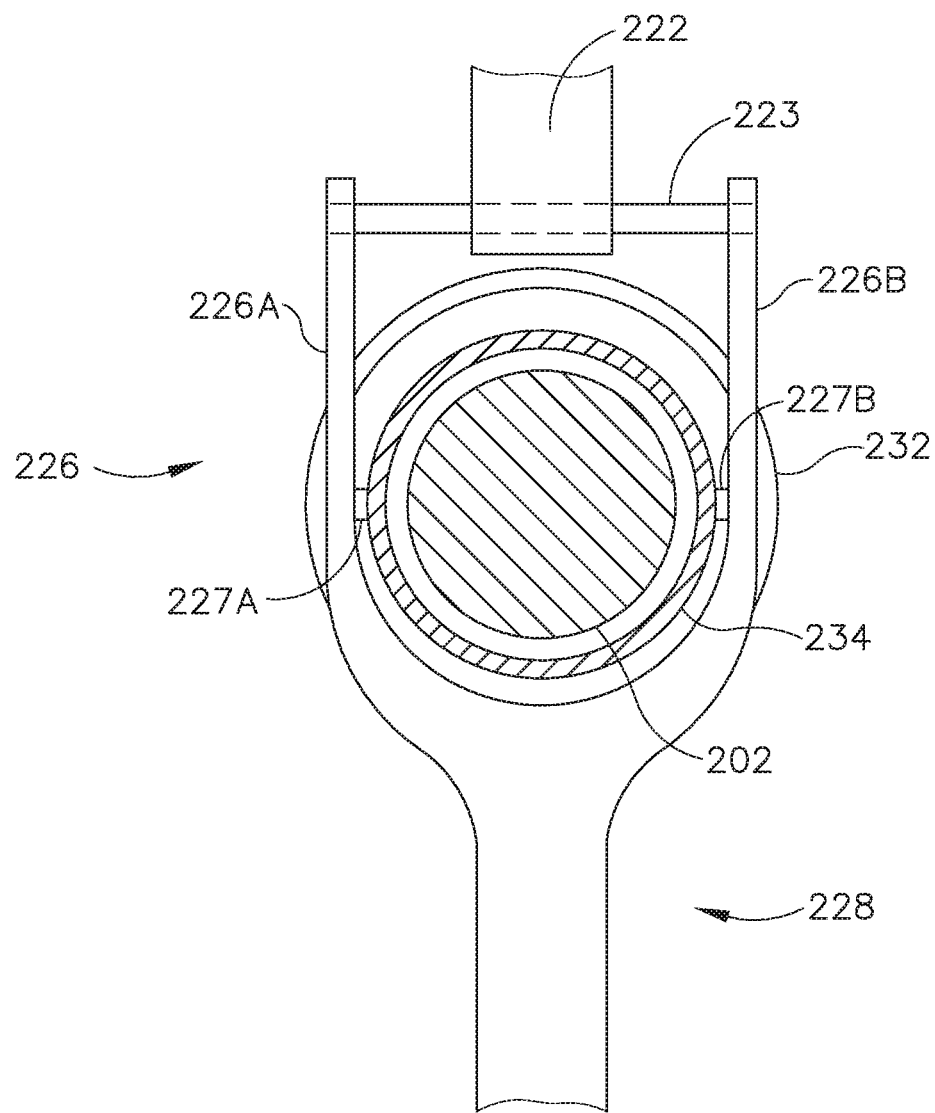
FIG. 7 depicts a partial cross-sectional view of the trigger assembly of FIG. 5A.

As best seen in FIG. 7, a top portion of trigger (228) includes a U-shaped member (226). U-shaped member (226) comprises a first arm (226A) and a second arm (226B). Inner tube (234) passes between first arm (226A) and second arm (226B) of U-shaped member (226). A pair of pins (227A, 227B) project from opposite sides of inner tube (234). A portion of each arm (226A, 226B) of U-shaped member (226), below pin (223) includes a vertical slot (229A, 229B). Pins (227A, 227B) are slidably and rotatably disposed within vertical slots (229A, 229B) such that rotation of trigger (228) causes longitudinal translation of inner tube (234). As discussed above, inner tube (234) is longitudinally translatable within outer sheath (232). It should therefore be understood that pivoting of trigger (228) toward pistol grip (224) will cause proximal longitudinal translation of inner tube (234) relative to handle assembly (220) and outer sheath (232); and that pivoting of trigger (228) away from pistol grip (224) will cause distal longitudinal translation of inner tube (234) relative to handle assembly (220) and outer sheath (232) as shown in FIGS. 5A-6B.

End effector (240) includes ultrasonic blade (201) and clamp arm (244). End effector (240) is configured to operate substantially similar to end effector (40) discussed above. In particular, longitudinal translation of inner tube (234) relative to handle assembly (220) and outer sheath (232) causes rotation of clamp arm (244) toward and away from ultrasonic blade (201) to thereby clamp tissue between clamp arm (244) and ultrasonic blade (201) to cut and/or seal the tissue. Furthermore, proximal longitudinal translation of inner tube (234) relative to handle assembly (220) and outer sheath (232) causes clamp arm (244) to move toward ultrasonic blade (201); and distal longitudinal translation of inner tube (234) relative to handle assembly (220) and outer sheath (232) causes clamp arm (244) to move away from ultrasonic blade (201). It should therefore be understood that pivoting of trigger (228) toward pistol grip (224) will cause clamp arm (244) to move toward ultrasonic blade (201); and that, pivoting of trigger (228) away from pistol grip (224) will cause clamp arm (244) to move away from ultrasonic blade (100).

As shown in FIGS. 5A-6B, instrument (210) of the present example further comprises a pair of springs (225A, 225B). A first end of each spring of pair of springs (225A, 225B) is coupled with body (222) of handle assembly (220). A second end each spring of pair of springs (225A, 225B) is coupled with a respective arm (226A, 226B) of U-shaped member (226) of trigger (228) below pin (223) such that trigger (228) is biased toward a position away from pistol grip (224). Furthermore, because trigger (228) is biased toward a position away from pistol grip (224), it should be understood that clamp arm (244) is biased toward ultrasonic blade (201). It should be understood that springs (225A, 225B) may be incorporated with any appropriate trigger assembly discussed below.

III. Exemplary Trigger Assembly with Complaint Feature

In some versions of instrument (10, 210), it may be desirable to limit the amount of force that a clamp arm (44, 244) may apply to tissue. As will be discussed in more detail below, the force applied by clamp arm (44, 244) may be limited by providing a trigger having a force limiting feature. Such force limiting features may comprise a component that is configured to deform upon experiencing a predetermined amount of force. This compliance of the force limiting feature may effectively limit the transfer of force from actuating a trigger (28, 228) to a respective clamp arm (44, 244) such that after the force limiting feature has deformed, only a nominal amount of additional force will be communicated to the clamp arm (44, 244) as the operator actuates trigger (28, 228) further. This additional force may be effectively insubstantial in that the additional force does not create any clinically significant tissue effects. The force limiting feature may nevertheless continue to permit the same amount of force to be applied by the clamp arm (44, 244) to the tissue as was applied before the force limiting feature began deforming. In other words, the tissue may still be clamped with approximately the same amount of force by clamp arm (44, 244) as was applied by clamp arm (44, 244) right before the compliant feature began deforming. Several merely illustrative examples of compliant features that may be used to effectively limit the force applied to tissue will be described in greater detail below, while other examples will be apparent to those of ordinary skill in the art in view of the teachings herein.

A. Exemplary Trigger Assembly with Upper Pivot and Flexible Band

Figure 8A:
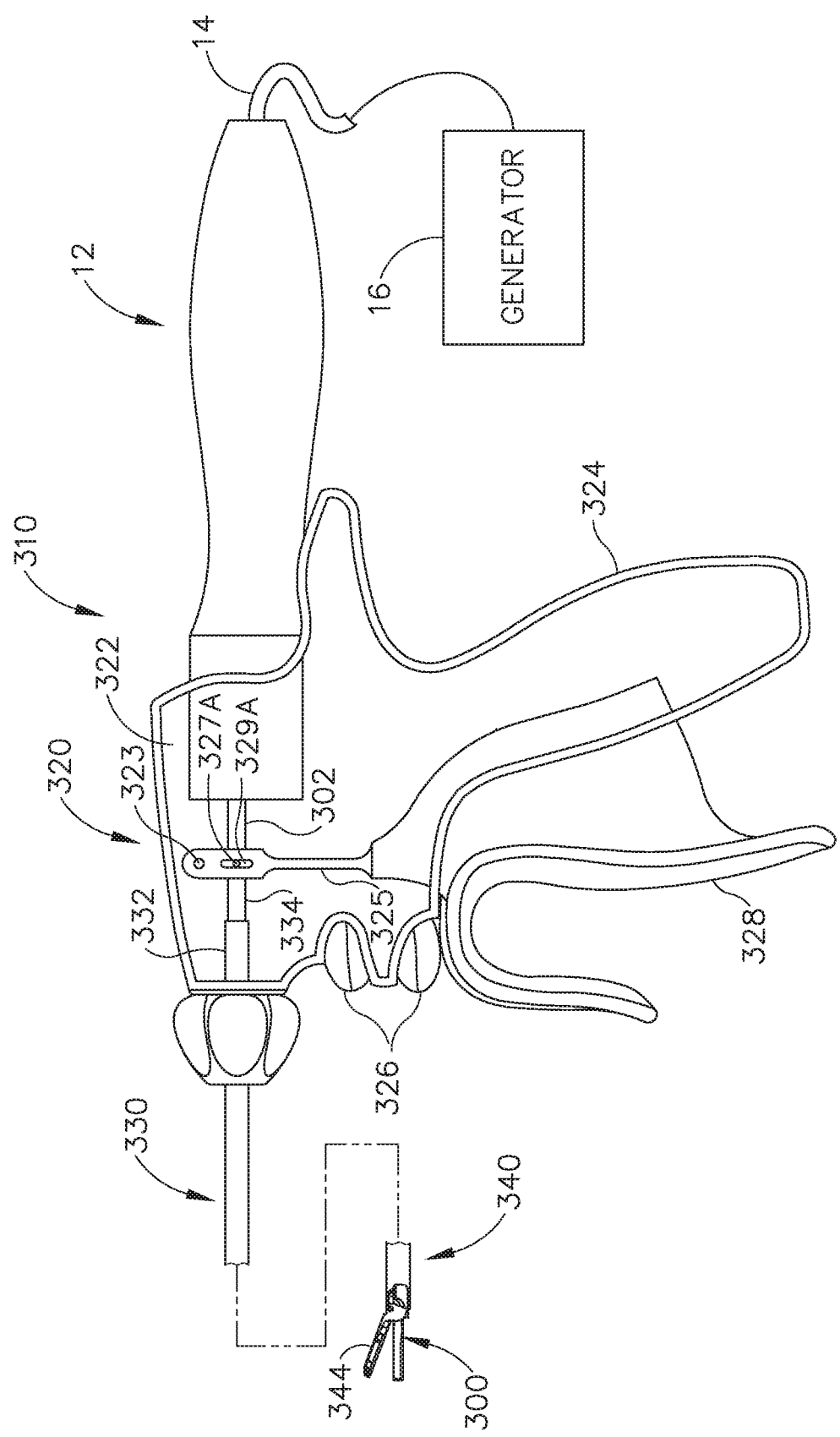
FIG. 8A depicts a side elevational view of another variation of the instrument of FIG. 1 with another exemplary alternative trigger assembly in a first position.
Figure 8B:
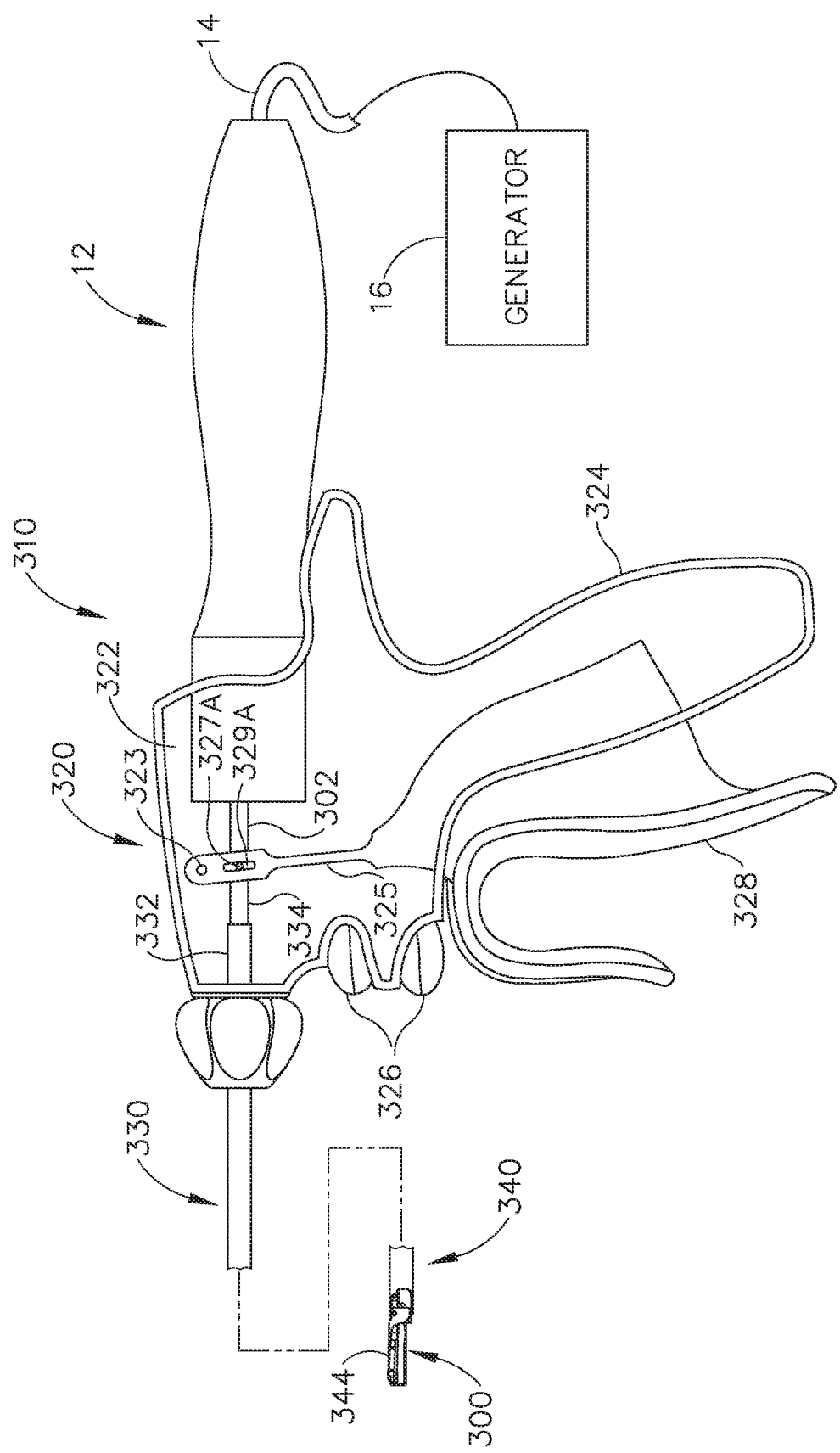
FIG. 8B depicts a side elevational view of the instrument of FIG. 8A with the trigger assembly moved into a second position.
Figure 8C:
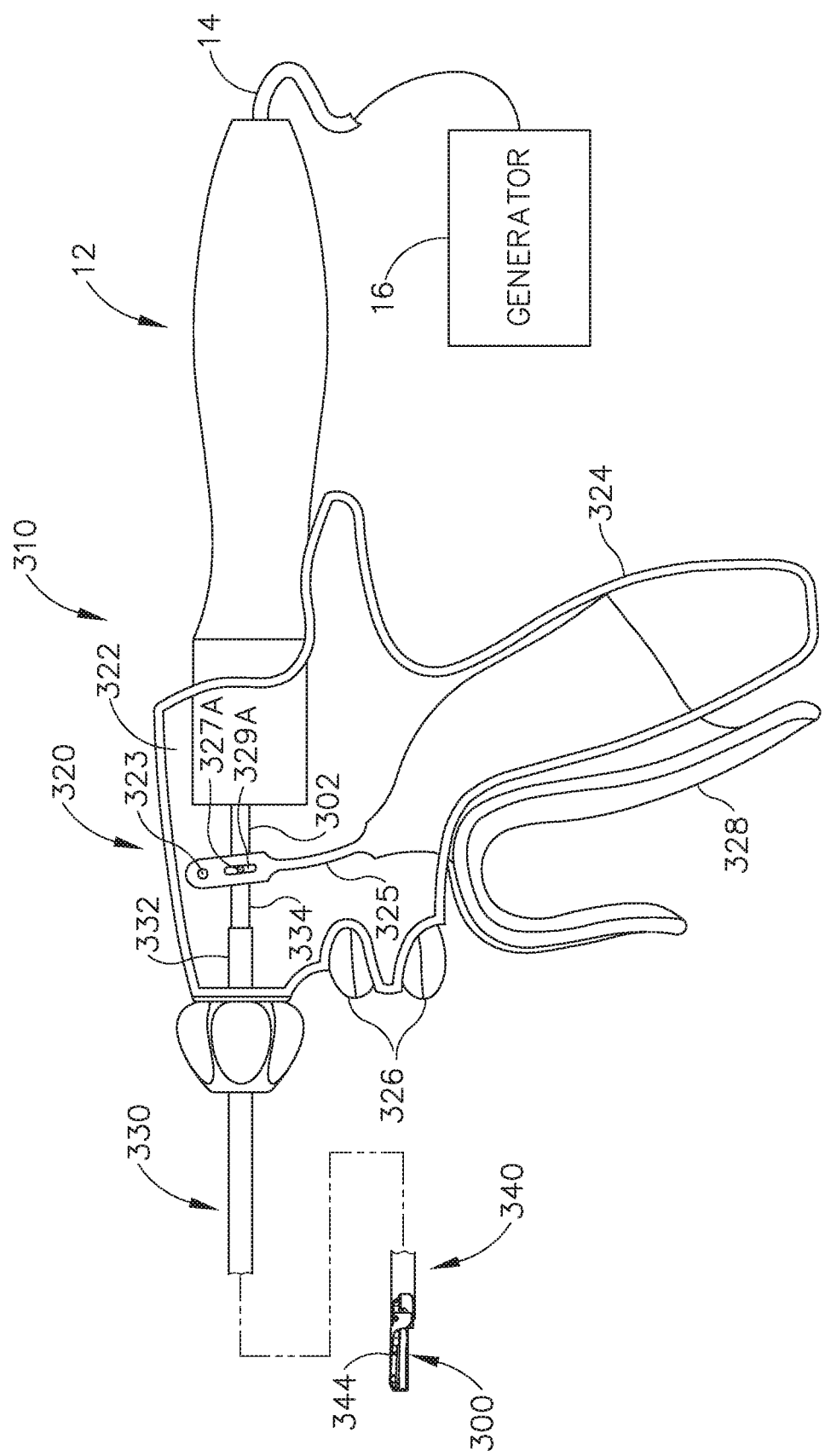
FIG. 8C depicts a side elevational view of the instrument of FIG. 8A with the trigger assembly moved into a third position.

FIGS. 8A-8C show another instrument (310) having a trigger (328) that rotates about an axis located above a shaft assembly (330). Instrument (310) of the present example is configured to operate substantially similar to instruments (10, 210) discussed above except for the differences discussed below. In particular, instrument (310) is configured to clamp tissue between a pivoting clamp arm (344) and an ultrasonic blade (300) to thereby cut and/or seal the tissue.

Instrument (310) of the present example comprises a handle assembly (320), shaft assembly (330), and an end effector (340). Shaft assembly (330) comprises an outer sheath (332), an inner tube (334) slidably disposed within outer sheath (332), and a waveguide (302) disposed within inner tube (334). As will be discussed in more detail below, longitudinal translation of inner tube (334) relative to handle assembly (320) and outer sheath (332) is configured to cause actuation of clamp arm (344) of end effector (340). Handle assembly (320) comprises a body (322) including a pistol grip (324) and a pair of buttons (326). Handle assembly (320) also includes a trigger (328) that is pivotable toward and away from pistol grip (324). Trigger (328) is pivotably coupled to body (322) of handle assembly (320) via a pin (323) such that trigger (328) rotates about an axis located above shaft assembly (330).

A portion of trigger (328), below pin (323), is coupled with inner tube (334) in a manner similar to trigger (228) and inner tube (234) of instrument (210) discussed above. In particular, a pair of pins (327A, 327B) projecting from opposite sides of inner tube (334) are slidably and rotatably disposed within a pair of vertical slots (329A, 329B) of trigger (328) such that rotation of trigger (328) causes longitudinal translation of inner tube (334). As discussed above, inner tube (334) is longitudinally translatable within outer sheath (332). It should therefore be understood that pivoting of trigger (328) toward pistol grip (324) will cause proximal longitudinal translation of inner tube (334) relative to handle assembly (320) and outer sheath (332); and that, pivoting of trigger (328) away from pistol grip (324) will cause distal longitudinal translation of inner tube (334) relative to handle assembly (320) and outer sheath (332).

End effector (340) includes ultrasonic blade (300) and clamp arm (344). End effector (340) is configured to operate substantially similar to end effector (40) discussed above. In particular, longitudinal translation of inner tube (334) relative to handle assembly (320) and outer sheath (332) causes rotation of clamp arm (344) toward and away from ultrasonic blade (300) to thereby clamp tissue between clamp arm (344) and ultrasonic blade (300) to cut and/or seal the tissue. Furthermore, proximal longitudinal translation of inner tube (334) relative to handle assembly (320) and outer sheath (332) causes clamp arm (344) to move toward ultrasonic blade (300); and distal longitudinal translation of inner tube (334) relative to handle assembly (320) and outer sheath (332) causes clamp arm (344) to move away from ultrasonic blade (300). It should therefore be understood that pivoting of trigger (328) toward pistol grip (324) will cause clamp arm (344) to move toward ultrasonic blade (300); and that pivoting of trigger (328) away from pistol grip (324) will cause clamp arm (344) to move away from ultrasonic blade (300).

It should be understood that force will be applied to the tissue between clamp arm (344) and ultrasonic blade (300) by proximal longitudinal translation of inner tube (334); and that additional longitudinal translation of inner tube (334) will apply additional force to the tissue between clamp arm (344) and ultrasonic blade (300). Trigger (328) of the present example comprises a flexible band (325). The rigidity of flexible band (325) is configured to allow only a predetermined amount of force to be applied to the tissue between clamp arm (344) and ultrasonic blade (300). As shown in FIG. 8B, as trigger (328) is moved toward pistol grip (324) though a first range of motion, flexible band (325) remains substantially straight such that pivoting movement of trigger (328) is communicated to inner tube (334) to thereby drive clamp arm (344) toward ultrasonic blade (300) and thus apply force to the tissue. As shown in FIG. 8C, at a particular point during pivoting of trigger (328), clamp arm (344) and ultrasonic blade (300) apply a predetermined amount of force to the tissue clamped there between. At this point, flexible band (325) begins to deform such that additional pivoting of trigger (328) toward pistol grip (324) is not substantially communicated to inner tube (334); and such that no substantial additional force will be applied to the tissue between clamp arm (344) and ultrasonic blade (300). In other words, compliant deformation by flexible band (325) absorbs additional force applied to trigger (328) after trigger (328) has traveled through the first range of motion.

It should be understood that flexible band (325) may have any rigidity such that any appropriate amount of force may be applied to the tissue between clamp arm (344) and ultrasonic blade (300). Various suitable degrees of rigidity, and corresponding clamping force restrictions provided by compliance in flexible band (325), will be apparent to those of ordinary skill in the art in view of the teachings herein. It should also be understood that flexible band (325) of the present example is plastically deformable, such that flexible band (325) returns to a substantially straight configuration as shown in FIGS. 8A-8B after a deforming load is removed from flexible band (325).

B. Exemplary Trigger Assembly with Upper Pivot and Living Hinge

Figure 9B:
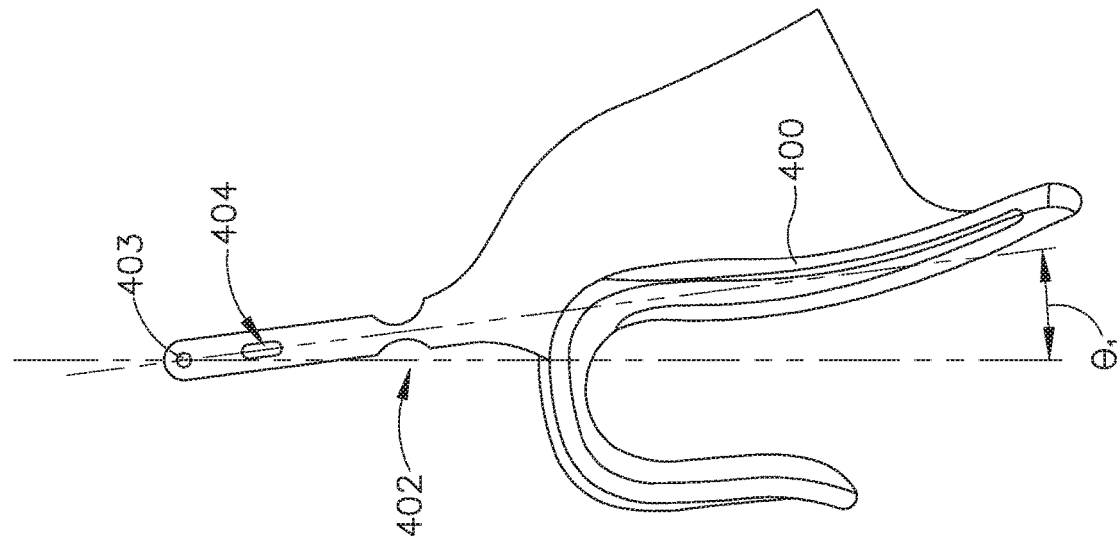
FIG. 9B depicts a side elevational view of the trigger assembly of FIG. 9A moved into a second position.
Figure 9A:
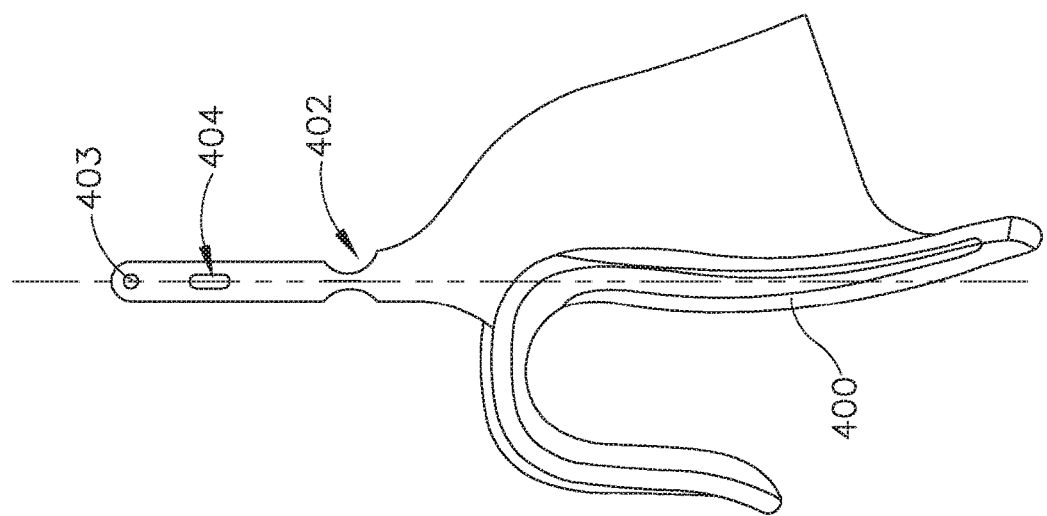
FIG. 9A depicts a side elevation view of yet another exemplary alternative trigger assembly in a first position.
Figure 9C:
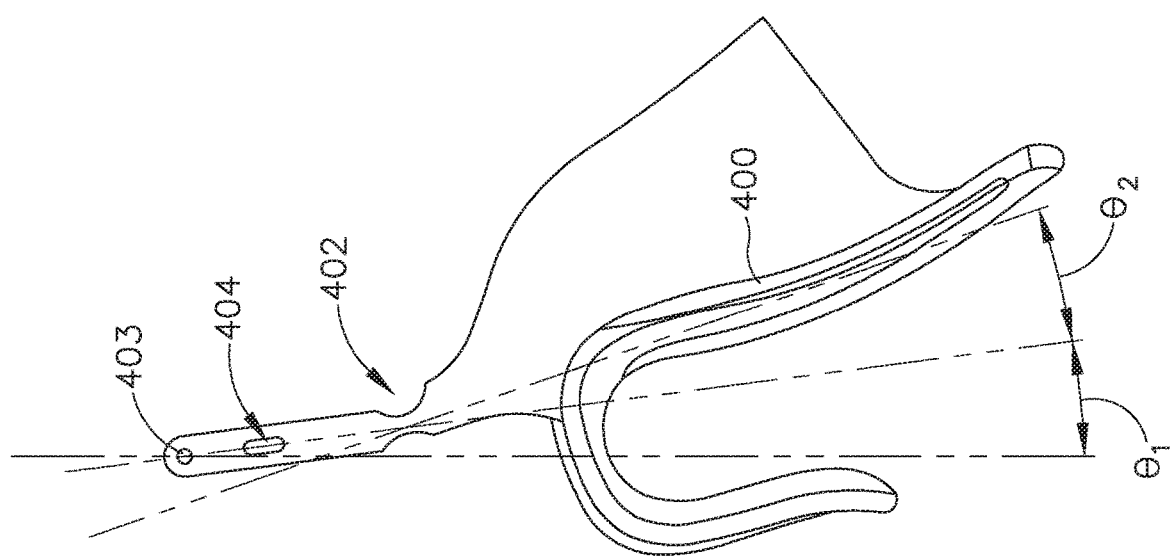
FIG. 9C depicts a side elevational view of the trigger assembly of FIG. 9A moved into a third position.

FIGS. 9A-9C show an exemplary alternative trigger (400) that may replace triggers (228, 328) discussed above. Trigger (400) is configured to operate substantially similar to triggers (228, 328) discussed above except for the differences discussed below. In particular, pivoting of trigger (400) causes longitudinal translation of an inner tube (not shown) to thereby drive a clamp arm (not shown) toward and/or away from an ultrasonic blade (not shown) and to thereby cut and/or seal the tissue. It should be understood that force will be applied to tissue between the clamp arm and the ultrasonic blade by proximal longitudinal translation of the inner tube and that additional longitudinal translation of the inner tube will apply additional force to the tissue between the clamp arm and the ultrasonic blade.

Trigger (400) of the present example comprises a living hinge (402), a pivot coupling (403), and a vertical slot (404). It should be understood that trigger (400) may be coupled within a handle assembly (not shown) via pivot coupling (403) either above or below a shaft assembly (not shown). It should further be understood that pivotal movement of trigger (400) may be transferred to the shaft assembly via a pin (not shown) disposed within vertical slot (404). The rigidity of living hinge (402) is configured to allow only a predetermined amount of force to be applied to the tissue between the clamp arm and the ultrasonic blade. As shown in FIG. 9B, as trigger (400) is pivoted through a first range of angular motion ($\Theta_1$), living hinge (402) remains substantially straight such that pivoting movement of trigger (400) through range of motion ($\Theta_1$) is communicated to the inner tube to thereby drive the clamp arm toward the ultrasonic blade and thus apply force to the tissue. As shown in FIG. 9C, at a particular point during pivoting of trigger (400), the clamp arm and the ultrasonic blade apply a predetermined amount of force to the tissue clamped there between. At this point, living hinge (402) begins to plastically deform such that additional pivoting of trigger (400) through a second range of angular motion ($\Theta_2$) is not substantially communicated to the inner tube and such that no substantial additional force will be applied to the tissue between the clamp arm and the ultrasonic blade. In other words, plastic deformation of living hinge (402) absorbs additional force applied to trigger (400) after trigger (400) has traveled through range of motion ($\Theta_1$).

It should be understood that living hinge (402) may have any rigidity such that any appropriate amount of force may be applied to the tissue between the clamp arm and the ultrasonic blade. Various suitable degrees of rigidity, and corresponding clamping force restrictions provided by compliance in living hinge (402), will be apparent to those of ordinary skill in the art in view of the teachings herein.

C. Exemplary Trigger Assembly with Upper Pivot and a Plurality of Living Hinges FIGS. 10A-10E show an exemplary alternative trigger (410) that may replace triggers (228, 328) discussed above, Trigger (410) is configured to operate substantially similar to triggers (228, 328, 400) discussed above except for the differences discussed below. In particular, pivoting of trigger (410) causes longitudinal translation of an inner tube (not shown) to thereby drive a clamp arm (not shown) toward and/or away from an ultrasonic blade (not shown) and to thereby cut and/or seal the tissue. It should be understood that force will be applied to tissue between the clamp arm and the ultrasonic blade by proximal longitudinal translation of the inner tube and that additional longitudinal translation of the inner tube will apply additional force to the tissue between the clamp arm and the ultrasonic blade.

Figure 10B:
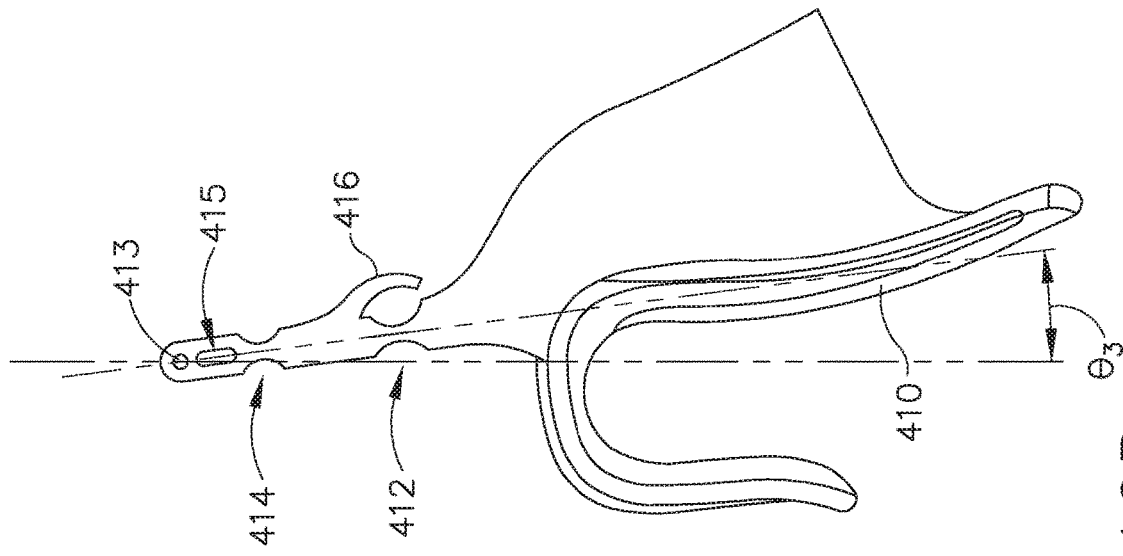
FIG. 10B depicts a side elevational view of the trigger assembly of FIG. 10A moved into a second position.
Figure 10A:
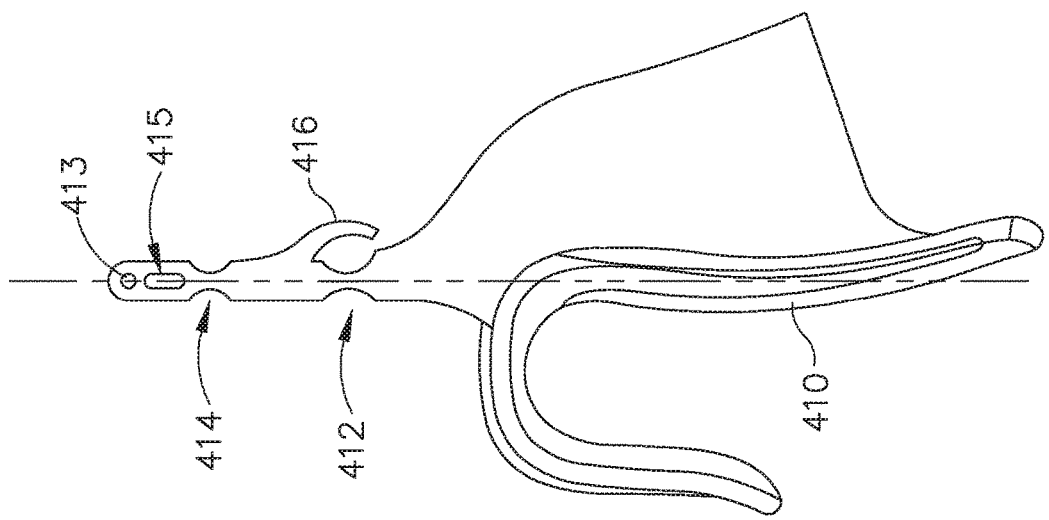
FIG. 10A depicts a side elevation view of yet another exemplary alternative trigger assembly in a first position.
Figure 10D:
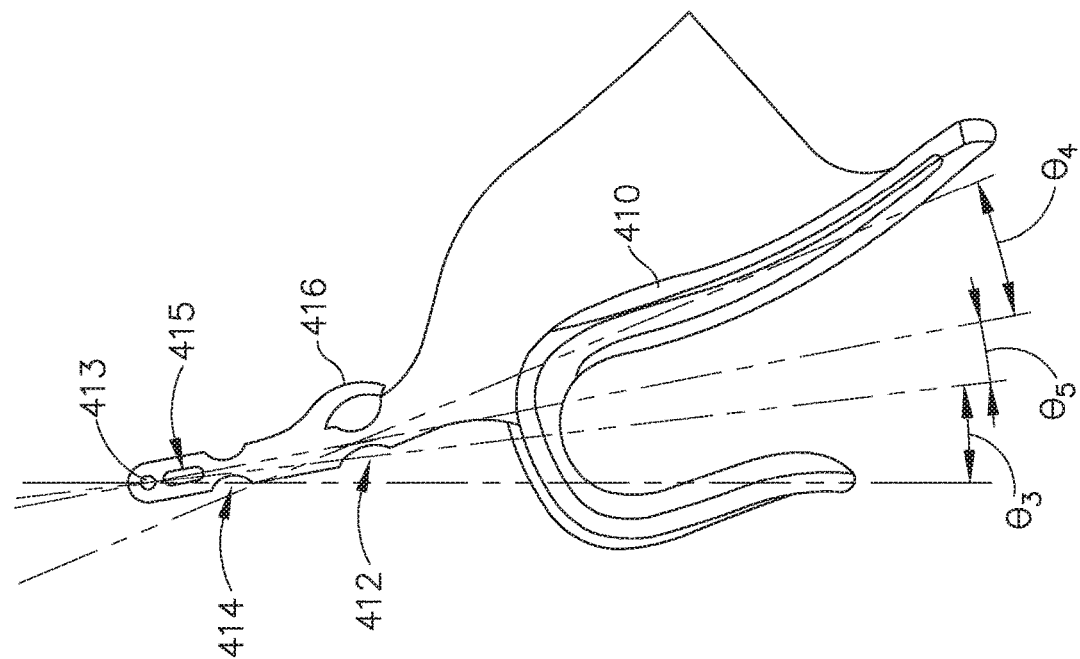
FIG. 10D depicts a side elevational view of the trigger assembly of FIG. 10A moved into a fourth position.
Figure 10C:
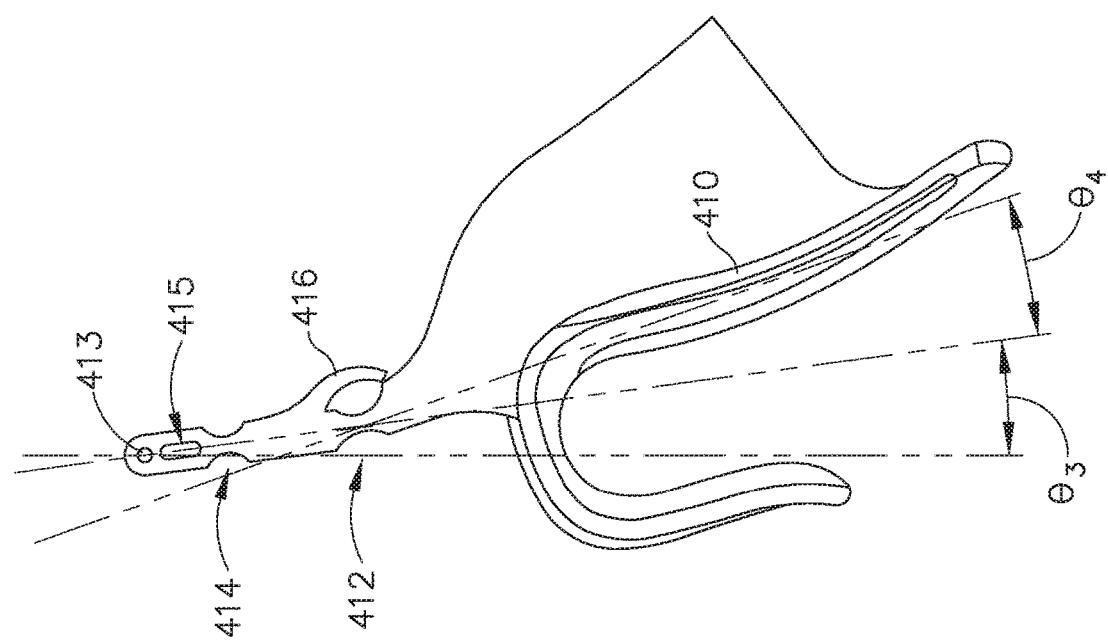
FIG. 10C depicts a side elevational view of the trigger assembly of FIG. 10A moved into a third position.

Trigger (410) of the present example comprises a pair of living hinges (412, 414), a stiffening member (416), a pivot coupling (413), and a vertical slot (415). It should be understood that trigger (410) may be coupled within a handle assembly (not shown) via pivot coupling (413) either above or below a shaft assembly (not shown). It should further be understood that pivotal movement of trigger (400) may be transferred to the shaft assembly via a pin (not shown) disposed within vertical slot (415). The rigidity of each living hinge (412, 414) is configured to allow only a predetermined amount of force to be applied to the tissue between the clamp arm and the ultrasonic blade. As will be discussed in more detail below, however, living hinge (412) and living hinge (414) each comprise a different rigidity. As shown in FIG. 10B, as trigger (410) is pivoted through a first range of angular motion ($\Theta_3$), each living hinge (412, 414) remains substantially straight such that pivoting movement of trigger (410) through range of motion ($\Theta_3$) is communicated to the inner tube to thereby drive the clamp arm toward the ultrasonic blade and thus apply force to the tissue. As shown in FIG. 10C, at a particular point during pivoting of trigger (410), the clamp arm and the ultrasonic blade apply a first predetermined amount of force to the tissue clamped there between. At this point, living hinge (412) begins to plastically deform such that additional pivoting of trigger (410) through a second range of angular motion ($\Theta_4$) is not substantially communicated to the inner tube and such that no substantial additional force will be applied to the tissue between the clamp arm and the ultrasonic blade as trigger (410) moves through second range of angular motion ($\Theta_4$). In other words, plastic deformation of living hinge (412) absorbs additional force applied to trigger (410) after trigger (410) has traveled through second range of angular motion ($\Theta_4$).

Figure 10E:
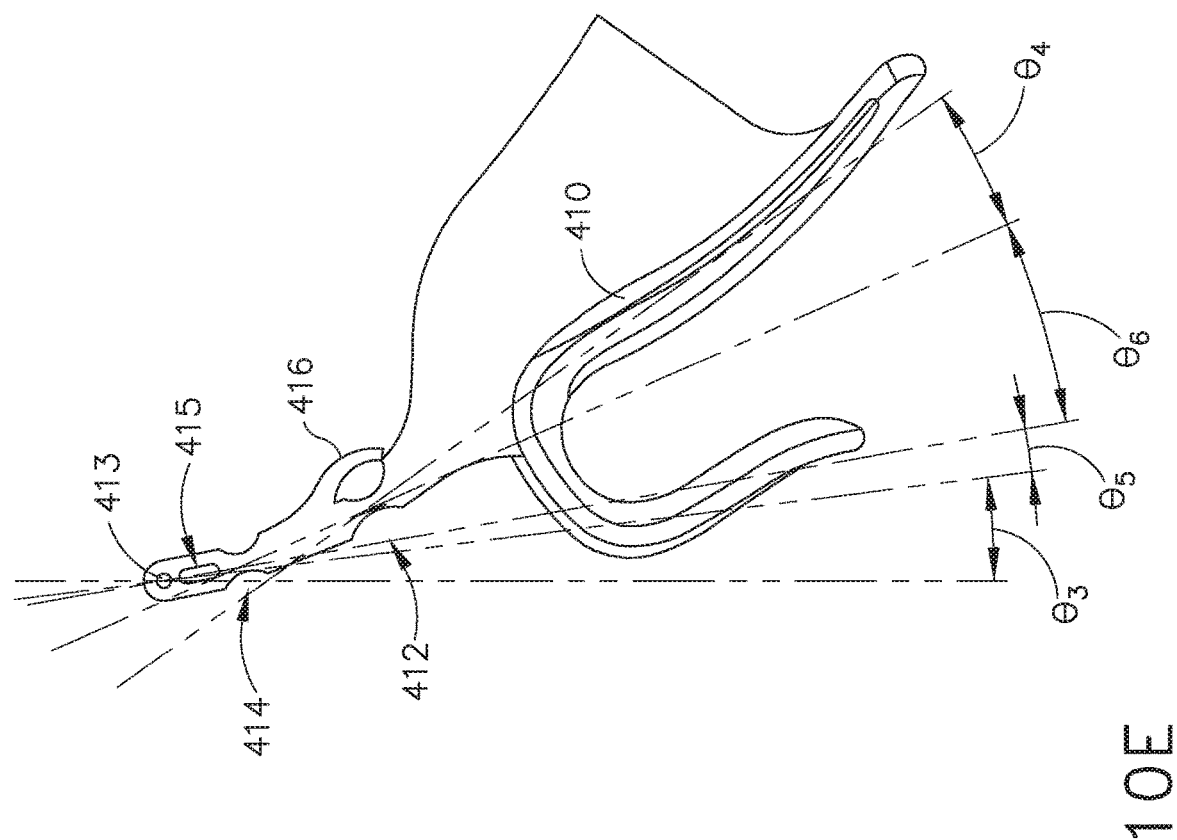
FIG. 10E depicts a side elevational view of the trigger assembly of FIG. 10A moved into a fifth position.

As shown in FIG. 10C, at a particular point during pivoting of trigger (410) through second range of angular motion ($\Theta_4$), living hinge (412) plastically deforms to a point where stiffening member (416) contacts an exterior surface of trigger (410). Contact between stiffening member (416) and the exterior surface of trigger (410) prevents living hinge (412) from plastically deforming further. Thus, as shown in FIG. 10D, as trigger (410) is pivoted further, a third range of angular motion ($\Theta_5$) is communicated to the inner tube to thereby drive the clamp arm toward the ultrasonic blade and thus apply additional force to the tissue. As shown in FIG. 10E, at a particular point during pivoting of trigger (410) through third range of angular motion ($\Theta_5$), the clamp arm and the ultrasonic blade apply a second predetermined amount of force to the tissue clamped there between. At this point, living hinge (414) begins to plastically deform such that additional pivoting of trigger (410) through a fourth range of angular motion ($\Theta_6$) is not substantially communicated to the inner tube and such that no substantial additional force will be applied to the tissue between the clamp arm and the ultrasonic blade as trigger (410) moves through fourth range of angular motion ($\Theta_6$), In other words, plastic deformation of living hinge (414) absorbs additional force applied to trigger (410) after trigger (410) has traveled through fourth range of angular motion ($\Theta_4$).

It should be understood that living hinges (412, 414) may have any rigidity such that any appropriate amount of force may be applied to the tissue between the clamp arm and the ultrasonic blade. Various suitable degrees of rigidity, and corresponding clamping force restrictions provided by compliance in living hinges (412, 414), will be apparent to those of ordinary skill in the art in view of the teachings herein.

D. Exemplary Trigger Assembly with Flexible Tab

Figure 11A:
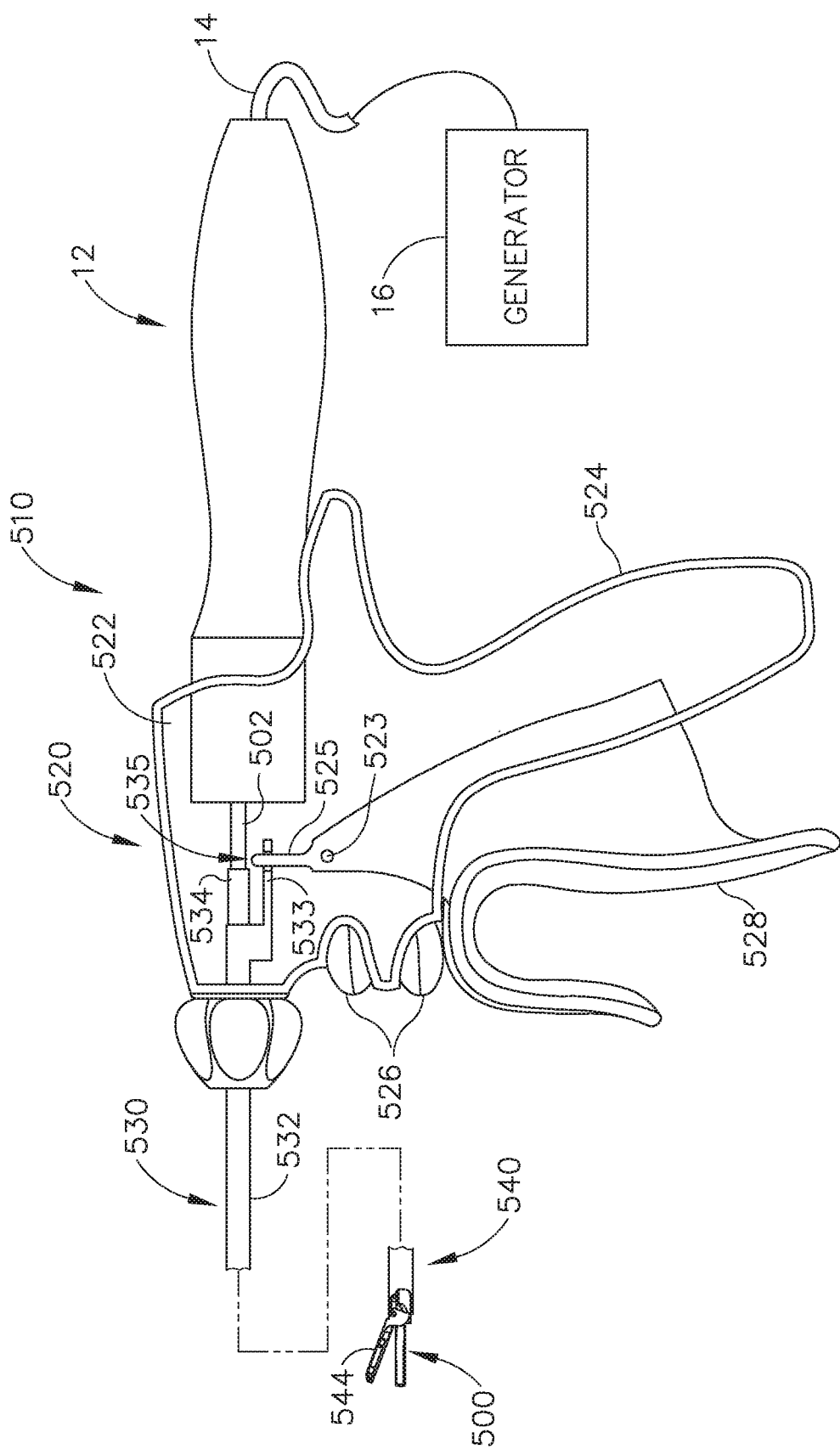
FIG. 11A depicts a side elevational view of yet another variation of the instrument of FIG. 1 with yet another exemplary alternative trigger assembly in a first position.
Figure 11B:
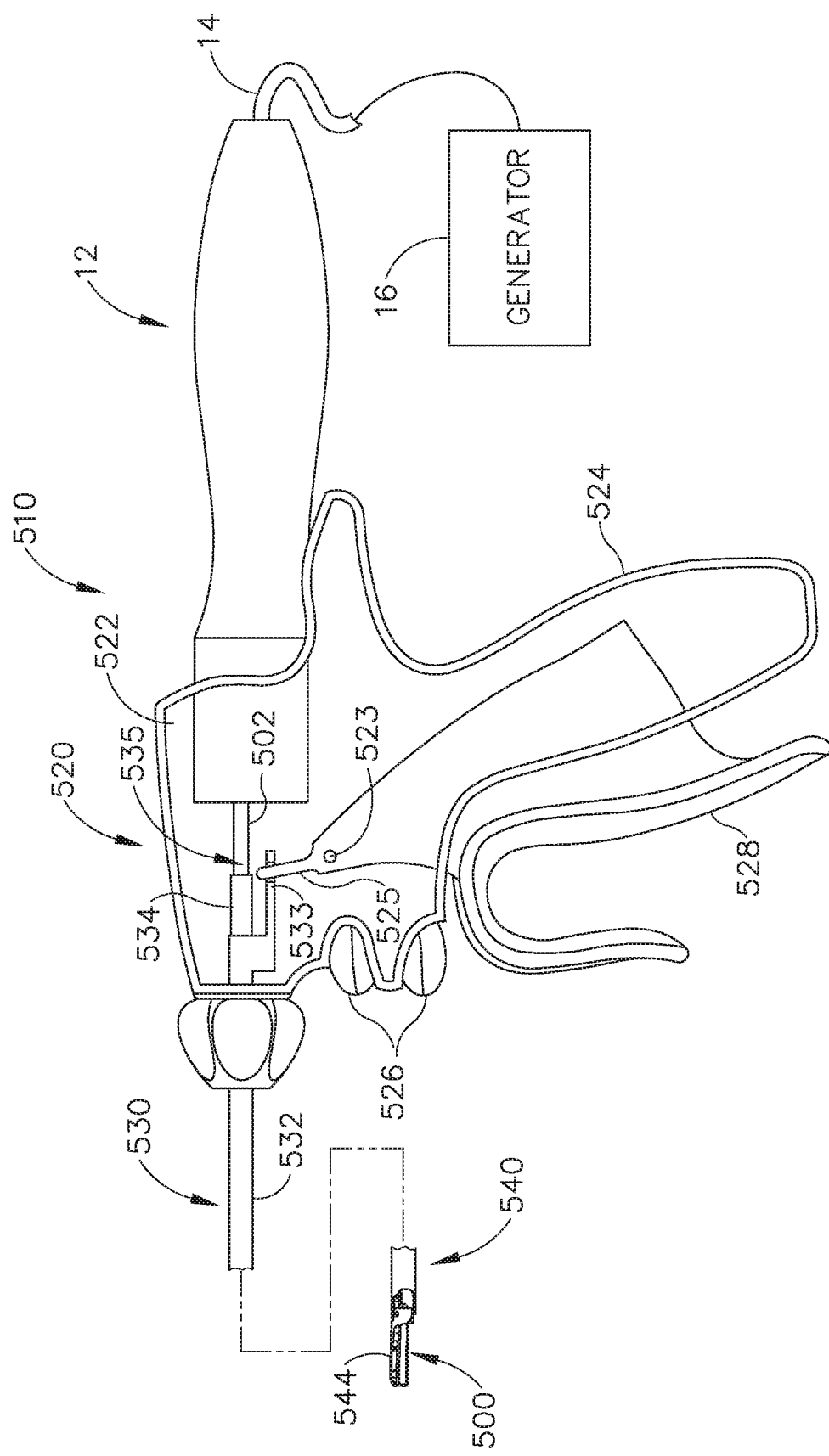
FIG. 11B depicts a side elevational view of the instrument of FIG. 11A with the trigger assembly moved into a second position.
Figure 11C:
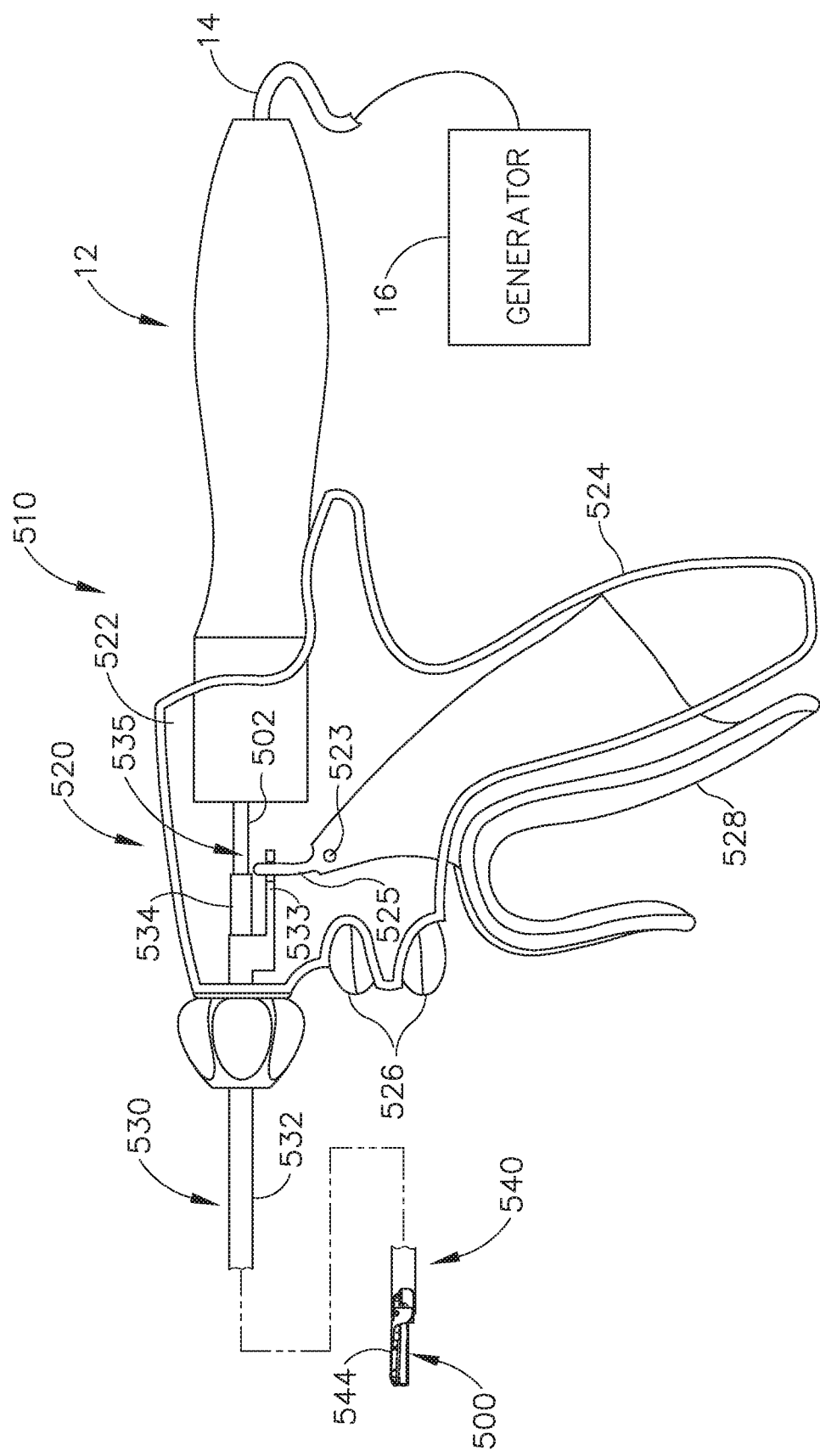
FIG. 11C depicts a side elevational view of the instrument of FIG. 11A with the trigger assembly moved into a third position.

FIGS. 11A-11C show such an instrument (510) having a trigger (528) that rotates about an axis located below a shaft assembly (530). Instrument (510) of the present example is configured to operate substantially similar to instrument (10) discussed above except for the differences discussed below. In particular, instrument (510) is configured to clamp tissue between a pivoting clamp arm (544) and an ultrasonic blade (500) to thereby cut and/or seal the tissue.

Instrument (510) of the present example comprises a handle assembly (520), shaft assembly (530), and an end effector (540). Shaft assembly (530) comprises an outer sheath (532), an inner tube (534) slidably disposed within outer sheath (532), and a waveguide (502) disposed within inner tube (534). As will be discussed in more detail below, longitudinal translation of outer sheath (532) relative to handle assembly (520) and inner tube (534) causes actuation of clamp arm (544) of end effector (540). Handle assembly (520) comprises a body (522) including a pistol grip (524) and a pair of buttons (526). Handle assembly (520) also includes trigger (528) that is pivotable toward and away from pistol grip (524). Trigger (528) is pivotably coupled to handle assembly (520) via a pin (523) such that trigger (528) rotates about an axis located below shaft assembly (530).

As best seen in FIG. 11A-11C, a flexible tab (525) extends from a top portion of trigger (528). An arm (533) extends proximally from a proximal end of outer sheath (532) parallel to inner tube (534) such that a gap is defined between arm (533) and inner tube (534). Arm (533) includes a slot (535). Tab (525) is disposed within slot (535) such that pivotal movement of trigger (528) causes longitudinal translation of outer sheath (532). It should therefore be understood that, pivoting of trigger (528) toward pistol grip (524) will cause distal longitudinal translation of outer sheath (532) relative to handle assembly (520) and inner tube (534); and that pivoting of trigger (528) away from pistol grip (524) will cause proximal longitudinal translation of outer sheath (526) relative to handle assembly (520) and inner tube (534).

End effector (540) includes ultrasonic blade (500) and pivoting clamp arm (544). Clamp arm (544) is rotatably coupled with a distal end of outer sheath (532) of shaft assembly (530) above ultrasonic blade (500). A distal end of inner tube (534) is pivotably coupled with a proximal end of clamp arm (544) below ultrasonic blade (500) such that longitudinal translation of outer sheath (532) relative to handle assembly (520) and inner tube (534) causes rotation of clamp arm (544) toward and away from ultrasonic blade (500) to thereby clamp tissue between clamp arm (544) and ultrasonic blade (500) to cut and/or seal the tissue. In particular, distal longitudinal translation of outer sheath (532) relative to handle assembly (520) and inner tube (534) causes clamp arm (544) to move toward ultrasonic blade (500); and proximal longitudinal translation of inner tube (534) relative to handle assembly (520) and inner tube (534) causes clamp arm (544) to move away from ultrasonic blade (500). It should therefore be understood that pivoting of trigger (528) toward pistol grip (524) will cause clamp arm (544) to move toward ultrasonic blade (500); and that pivoting of trigger (528) away from pistol grip (524) will cause clamp arm (544) to move away from ultrasonic blade (500).

It should be understood that force will be applied to the tissue between clamp arm (544) and ultrasonic blade (500) by distal longitudinal translation of outer sheath (532) relative to handle assembly (520) and inner tube (534); and that additional longitudinal translation of outer sheath (532) relative to handle assembly (520) and inner tube (534) will apply additional force to the tissue between clamp arm (544) and ultrasonic blade (500). The rigidity of flexible tab (525) is configured to allow only a predetermined amount of force to be applied to the tissue between clamp arm (544) and ultrasonic blade (500). As shown in FIG. 11B, as trigger (528) is moved toward pistol grip (524) through a first range of motion, flexible tab (525) remains substantially straight such that pivoting movement of trigger (528) is communicated to outer sheath (532) to thereby drive clamp arm (544) toward ultrasonic blade (500) and thus apply clamping force to the tissue. As shown in FIG. 11C, at a particular point during pivoting of trigger (528), clamp arm (544) and ultrasonic blade (500) apply a predetermined amount of force to the tissue clamped there between. At this point, flexible tab (525) begins to plastically deform such that additional pivoting of trigger (528) toward pistol grip (524) is not substantially communicated to outer sheath (532) and such that no substantial additional force will be applied to the tissue between clamp arm (544) and ultrasonic blade (500). In other words, plastic deformation of flexible tab (525) absorbs additional force applied to trigger (528) after trigger (528) has traveled through the first range of motion.

It should be understood that flexible tab (525) may have any rigidity such that any appropriate amount of force may be applied to the tissue between clamp arm (544) and ultrasonic blade (500). Various suitable degrees of rigidity, and corresponding clamping force restrictions provided by compliance in flexible tab (525), will be apparent to those of ordinary skill in the art in view of the teachings herein.

IV. Exemplary Trigger Assembly with Adjustable Restriction Feature

Figure 12A:
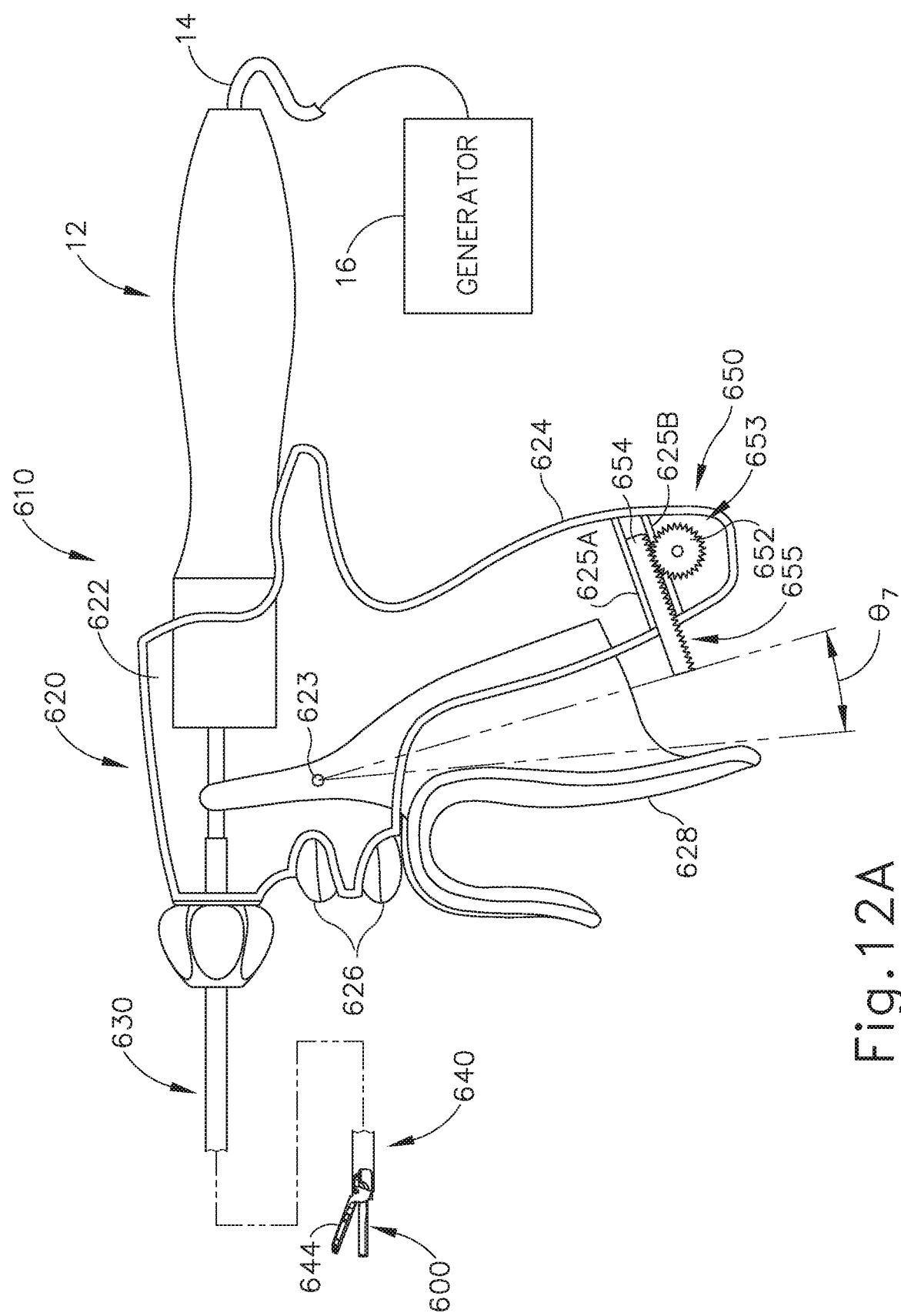
FIG. 12A depicts a side elevational view of yet another variation of the instrument of FIG. 1 with yet another exemplary alternative trigger assembly having a stopping mechanism in first position.
Figure 12B:
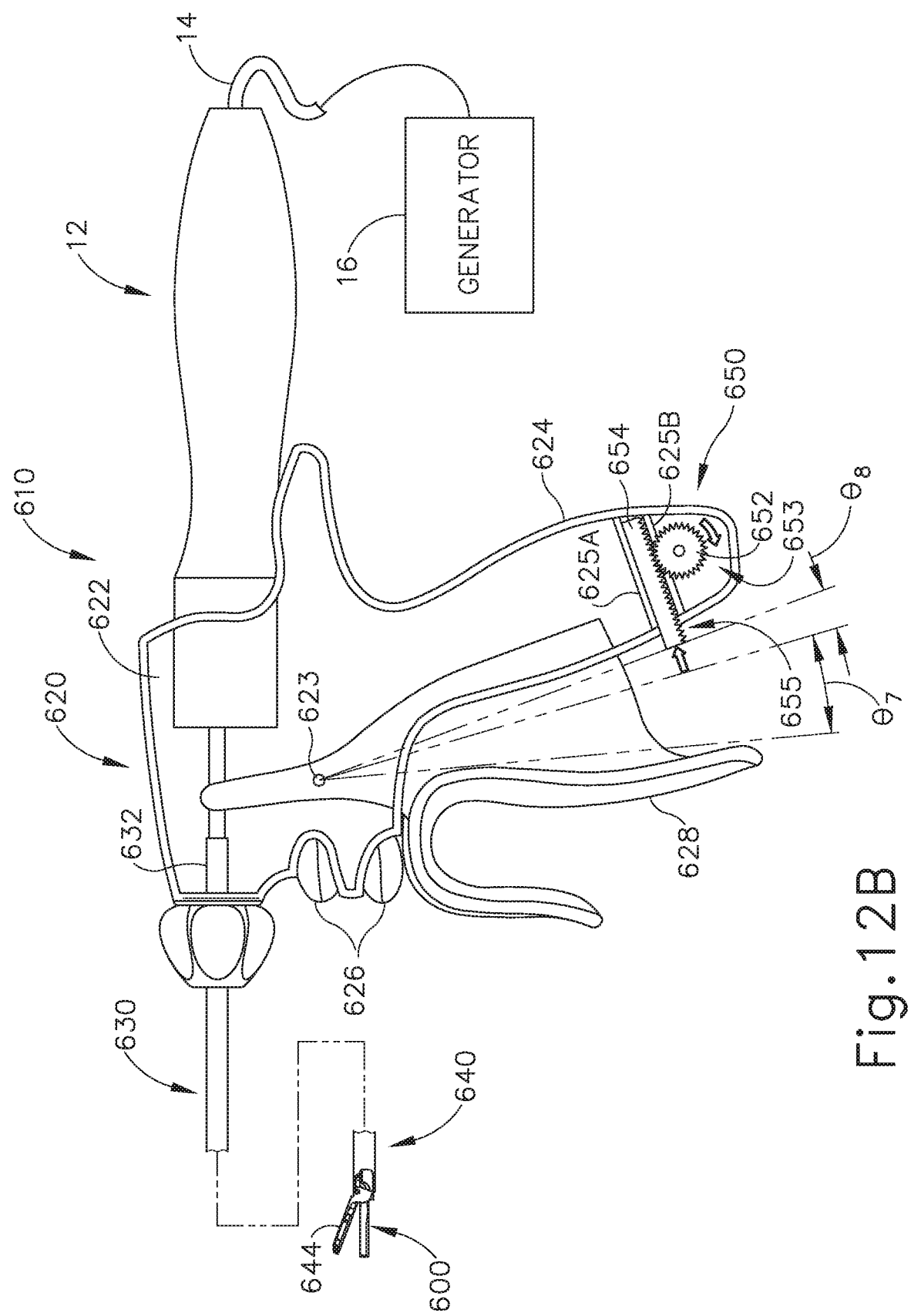
FIG. 12B depicts a side elevational view of the instrument and trigger assembly of FIG. 12A with the stopping mechanism moved into a second position.

In some versions of instruments (10, 210, 310, 510) discussed above, it may be desirable to limit that range of angular motion though which triggers (28, 228, 328, 528) may be pivoted. This may be done in addition to or in lieu of restricting the amount of force that may be applied to a clamp arm by a trigger. FIGS. 12A and 12B show an exemplary alternative instrument (610). Instrument (610) of the present example is configured to operate substantially similar to instruments (10, 210, 310, 510) discussed above except for the differences discussed below. In particular, instrument (610) is configured to clamp tissue between a pivoting clamp arm (644) and an ultrasonic blade (600) to thereby cut and/or seal the tissue.

Instrument (610) of the present example comprises a handle assembly (620), shaft assembly (630), and an end effector (640). Handle assembly (620) comprises a body (622) including a pistol grip (624) and a pair of buttons (626). Handle assembly (620) also includes trigger (628) that is pivotable toward and away from pistol grip (624). Trigger (628) is pivotably coupled to handle assembly (620) via a pin (623) such that trigger (628) rotates about an axis located below shaft assembly (630). As will be understood from the discussion below, however, trigger (628) may rotate about an axis located at any appropriate position, including but not limited to a position above shaft assembly (630).

Handle assembly (620) further comprises an adjustable restriction feature (650). Restriction feature (650) is configured to limit the range of motion of trigger (628). Restriction feature (650) of the present example comprises a pinion gear (652) and a rack (654). Pinion gear (652) is rotatably coupled with pistol grip (624) of body (622) of handle assembly (620) such that pinion gear (652) freely rotates. Rack (654) is disposed within a pair of guides (625A, 625B) that project from an interior surface of body (622) such that rack (654) slides within guides (625A, 6258B) between a distal position and a proximal position. An exterior surface of pinion gear (652) presents a plurality of teeth (653). A bottom surface of rack (654) presents a plurality of teeth (655). Plurality of teeth (653) of pinion gear (652) engages plurality of teeth (655) of rack (654) such that rotation of pinion gear (652) causes translation of rack (654) within guides (625A, 625B). A distal end of rack (654) is configured to contact trigger (628) to thereby limit the range of motion of trigger (628). As shown in FIG. 12A, in the distal position, the range of motion of trigger (628) is limited to a first range of angular motion (Θ₇). As shown in FIG. 12B, when rack (654) is moved into the proximal position, the range of motion of trigger (628) is operable to move between first range of angular motion (Θ₇) as well as an additional range of angular motion (Θ₈). It should be understood that, by limiting the range of motion of trigger (628), the range of motion of clamp arm (644) is also be limited. Thus, it should be understood that clamp arm (644) is configured to clamp down upon tissue with more force with rack (654) in the proximal position as opposed to the distal portion. Rack (654) may positioned at any point between the distal position and the proximal position.

Rotation of pinion gear (652) may be controlled by a knob (not shown) protruding from pistol grip (624). Pinion gear (652) may also be "locked," such that pinion gear (652) may not be rotated, such that rack (654) is also "locked" in position. It should be understood that rotation of gear (652) and translation of rack (654) may be driven by any appropriate method in addition to or in lieu of a knob, including but not limited to a motor that drives rotation of pinion gear (652) and translation of rack (654). Furthermore, rack (654) may be translated by a linear actuator, such that pinion gear (652) is not necessary. Other suitable ways in which rack (654) may be actuated will be apparent to those of ordinary skill in the art in view of the teachings herein.

V. Alternative Clamp Arms and Blade Tips

In some versions of instruments (10, 210, 310, 510, 610) discussed above, it may be desirable to provide an end effector having a clamp arm and/or ultrasonic blade with geometric profiles that provide for improved dissection of tissue, more efficient cutting of tissue, and/or more efficient manipulation of tissue. FIGS. 13-21 show exemplary end effectors that may be used with any instrument (10, 210, 310, 510, 610) discussed above. The clamp arms discussed below are configured to operate substantially similar to clamp arms (44, 244, 344, 544, 644) discussed above, except for the differences discussed below. In particular, the clamp arms discussed below are configured to clamp tissue against an ultrasonic blade to thereby cut and/or seal the tissue. Also, the ultrasonic blades discussed below are configured to operate substantially similar to ultrasonic blades (100, 200, 300, 500, 600) discussed above, except for the differences discussed below. In particular, the ultrasonic blades discussed below are configured to vibrate at ultrasonic frequencies and thereby cut and/or seal the tissue.

It should be understood that the exemplary ultrasonic blades discussed below may be used alone or in conjunction with the exemplary clamp arms discussed below. It should also be understood that the exemplary ultrasonic blades discussed below may be used with any appropriate clamp arm discussed herein; and that the exemplary clamp arms discussed below may be used with any appropriate ultrasonic blade discussed herein.

A. First Exemplary Clamp Arm and Blade Tip

Figure 13:
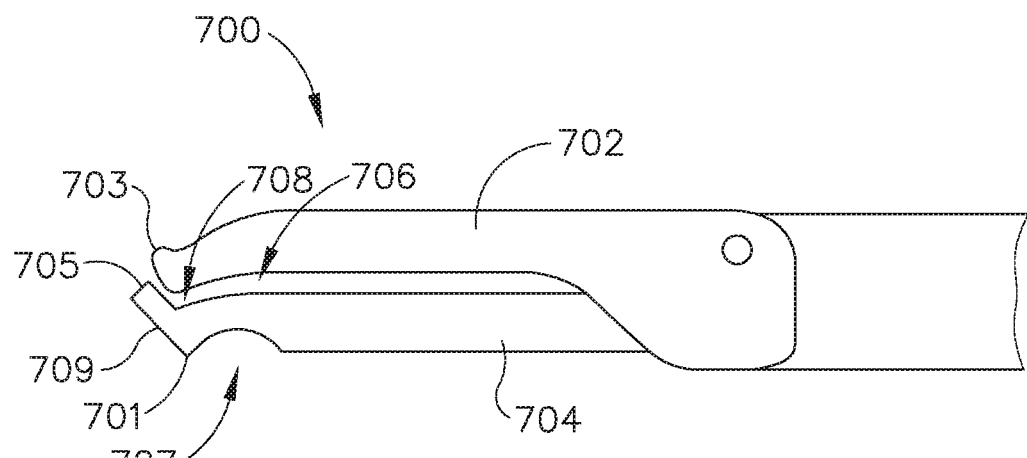
FIG. 13 depicts a side elevational view of an exemplary clamp arm and blade tip operable to be used with the instrument of FIG. 1.

FIG. 13 shows an exemplary alternative end effector (700). End effector (700) comprises a clamp arm (702) and an ultrasonic blade (704). A distal tip of clamp arm (702) presents an arcuate projection (703) extending generally upwardly from a top surface of clamp arm (702). A distal tip of ultrasonic blade (704) comprises a rectangular projection (705) extending upwardly and distally from a top surface of ultrasonic blade (704). A top surface of a distal end of ultrasonic blade (704) proximal of projection (705) presents a curved profile (706). Curved profile (706) is curved downwardly and terminates at projection (705) thereby forming a pocket (708). In a closed position, the distal tip of clamp arm (702) is positioned within pocket (708) between curved profile (706) and projection (705). Projection (705) extends beyond a distal tip of clamp arm (702), and as will be discussed below, this may provide a user with better access to thereby use projection (705). A distal surface (709) of projection (705) presents a flat planar surface (709). A bottom surface of the distal end of ultrasonic blade (704) presents an arcuate recess (707). A sharp edge (701) is formed on the bottom surface of ultrasonic blade (704) between arcuate recess (707) and projection (705).

Pocket (708) and projection (705) may be used to prevent tissue and/or vessels from squeezing out of the distal end of end effector (700) as clamp arm (702) applies clamping force to the tissue and/or vessels. Surface (709) of projection (705) may be used to seal vessels that do not extend adequately from tissue to allow a user to clamp the vessel between clamp arm (702) and ultrasonic blade (704). In other words, surface (709) may be used to provide spot sealing or "bleeder touch ups." Ultrasonic blade (704)—including surface (709) of projection (705) and/or clamp arm (702) may also be used to apply monopolar and/or bipolar RE energy to tissue. Sharp edge (701) may be used to slice through tissue without having to damp the tissue between clamp arm (702) and ultrasonic blade (704), in a back-scoring type of movement or otherwise. It should also be understood that pocket (708) and/or recess (707) may be used to cradle and cauterize/seal vessels and ducts, without transecting the tissue forming the vessels or ducts.

B. Second Exemplary Clamp Arm and Blade Tip

Figure 14:
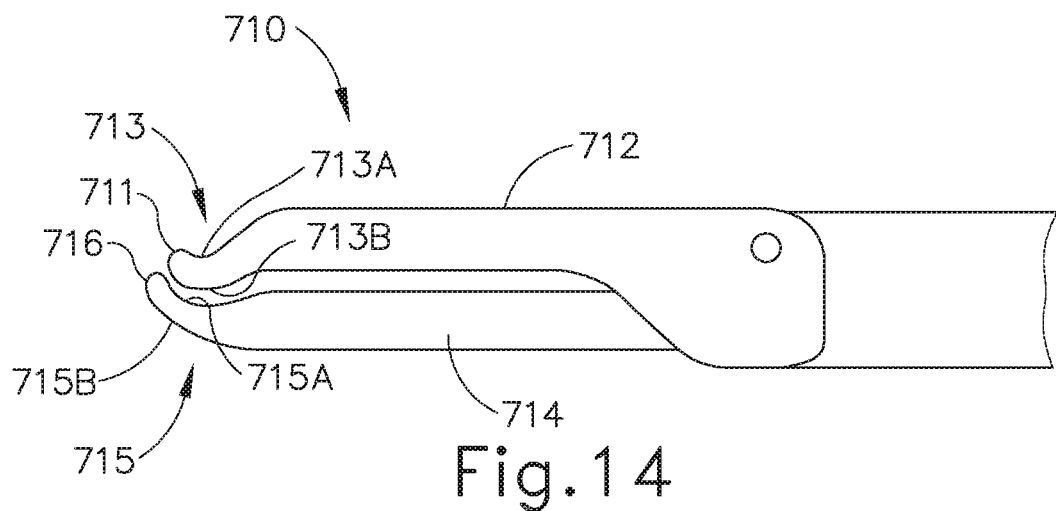
FIG. 14 depicts a side elevational view of an exemplary alternative clamp arm and blade tip operable to be used with the instrument of FIG. 1.

FIG. 14 shows another exemplary alternative end effector (710). End effector (710) comprises a clamp arm (712) and an ultrasonic blade (714). A distal tip of clamp arm (712) comprises a curved profile (713) that terminates into an arcuate tip (711). Arcuate tip (711) extends generally upwardly from the distal tip of clamp arm (712). Curved profile (713) includes a concave top curve (713A) and a convex bottom curve (713B). Bottom curve (713B) forms a concave profile. A distal tip of ultrasonic blade (714) comprises a curved profile (715) that terminates into an arcuate tip (716). Curved profile (715) includes a top curve (715A) and a bottom curve (715B). Top curve (715A) forms a convex profile/pocket into which the concave profile of bottom curve (713B) of clamp arm (712) is positioned when in a closed position. Arcuate tip (716) of ultrasonic blade (714) extends beyond arcuate tip (711) of clamp arm (712), and as will be discussed below, this may provide a user with better access to thereby use arcuate tip (716) and a distal surface of bottom curve (715B).

The convex profile/pocket of top curve (715A) and projection (716) may be used to prevent tissue and/or vessels from squeezing out of the distal end of end effector (710) as clamp arm (712) applies clamping force to the tissue and/or vessels. Bottom curve (715B) and/or arcuate tip (716) may be used to seal vessels that do not extend adequately from tissue to allow a user to clamp the vessel between clamp arm (712) and ultrasonic blade (714). In other words, bottom curve (715B) and/or arcuate tip (716) may be used to provide spot sealing or "bleeder touch ups." Ultrasonic blade (714)—including bottom curve (715B) and arcuate tip (716)—and/or clamp arm (712) may be used to apply monopolar and/or bipolar RF energy to tissue. It should also be understood that the convex profile/pocket of top curve (715A) and projection (716) may be used to cradle and cauterize/seal vessels and ducts, without transecting the tissue forming the vessels or ducts.

C. Third Exemplary Clamp Arm and Blade Tip

Figure 15:
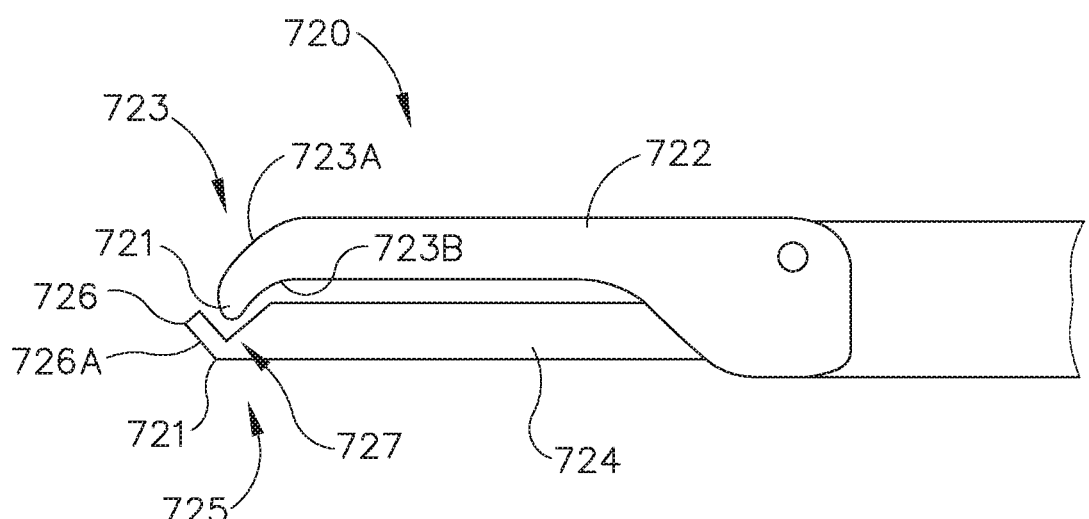
FIG. 15 depicts a side elevational view of another exemplary alternative clamp arm and blade tip operable to be used with the instrument of FIG. 1.

FIG. 15 shows yet another exemplary alternative end effector (720). End effector (720) comprises a clamp arm (722) and an ultrasonic blade (724). A distal tip of clamp arm (722) comprises a curved profile (723) that terminates into an arcuate tip (721). Arcuate tip (721) extends generally downwardly from the distal tip of clamp arm (722). Curved profile (723) includes a top curve (723A) and a bottom curve (723B). Bottom curve (713B) forms a convex profile. A distal end of ultrasonic blade (724) comprises a jagged profile (725) that terminates into a rectangular tip (726) and further defines a sharp edge (721). Jagged profile (725) includes a pocket (727) formed in a top surface of a distal end of ultrasonic blade (724). Arcuate tip (721) is configured to be positioned within pocket (727) of ultrasonic blade (724) when clamp arm (722) is in a closed position. Rectangular tip (726) extends beyond a distal end of clamp arm (722), and as will be discussed below, this may provide a user with better access to thereby use rectangular tip (726). A distal surface of rectangular tip (726) presents a flat planar surface (726A).

Pocket (727) and rectangular tip (726) may be used to prevent tissue and/or vessels from squeezing out of the distal end of end effector (720) as clamp arm (722) applies clamping force to the tissue and/or vessels. Surface (726A) of rectangular tip (726) may be used to seal vessels that do not extend adequately from tissue to allow a user to clamp the vessel between clamp arm (722) and ultrasonic blade (724). In other words, surface (726A) may be used to provide spot sealing or "bleeder touch ups." Ultrasonic blade (724)—including surface (726A) of rectangular tip (726)—and/or clamp arm (722) may be used to apply monopolar and/or bipolar RE energy to tissue, Sharp edge (721) may be used to slice through tissue without having to clamp the tissue between clamp arm (722) and ultrasonic blade (724), in a back-scoring type of movement or otherwise. In some instances, sharp edge (721) may be used in conjunction with pocket (727) to improve grasping of tissue and/or to improve grasping and bluntly tearing tissues for dissection. It should also be understood that pocket (727) may be used to cradle and cauterize/seal vessels and ducts, without transecting the tissue forming the vessels or ducts.

D. Fourth Exemplary Clamp Arm and Blade Tip

Figure 16:
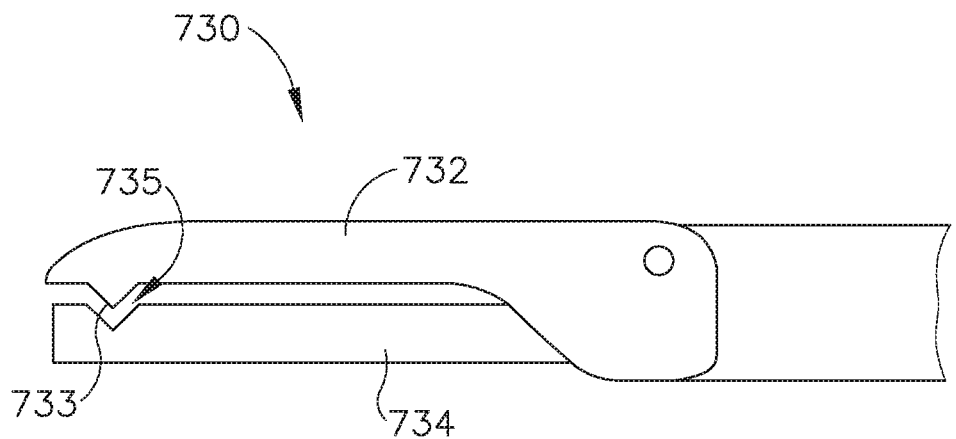
FIG. 16 depicts a side elevational view of yet another exemplary alternative clamp arm and blade tip operable to be used with the instrument of FIG. 1.

FIG. 16 shows yet another exemplary alternative end effector (730). End effector (730) comprises a clamp arm (732) and an ultrasonic blade (734). A distal end of clamp arm (732) includes a triangular projection (733) extending downwardly from clamp arm (732). A distal end of ultrasonic blade (734) includes a triangular pocket (735). Triangular projection (733) is configured to be positioned within triangular pocket (735) of ultrasonic blade (734) when clamp arm (732) is in a closed position. It should be understood that triangular projection (733) and triangular pocket (735) may be positioned anywhere along clamp arm (732) and ultrasonic blade (734) respectively. It should further be understood that clamp arm (732) and ultrasonic blade (734) may comprise a series of triangular projections (733) and triangular pockets (735) spaced along the lengths of clamp arm (732) and ultrasonic blade (734). Triangular pocket (735) and triangular projection (733) may be used to enhance the grip on tissue and prevent tissue and/or vessels from squeezing out of the distal end of end effector (730) as clamp arm (732) applies clamping force to the tissue and/or vessels. Ultrasonic blade (734) and/or clamp arm (732) may also be used to apply monopolar and/or bipolar RF energy to tissue. It should also be understood that pocket (735) may be used to cradle and cauterize/seal vessels and ducts, without transecting the tissue forming the vessels or ducts.

E. Fifth Exemplary Clamp Arm and Blade Tip

Figure 17:
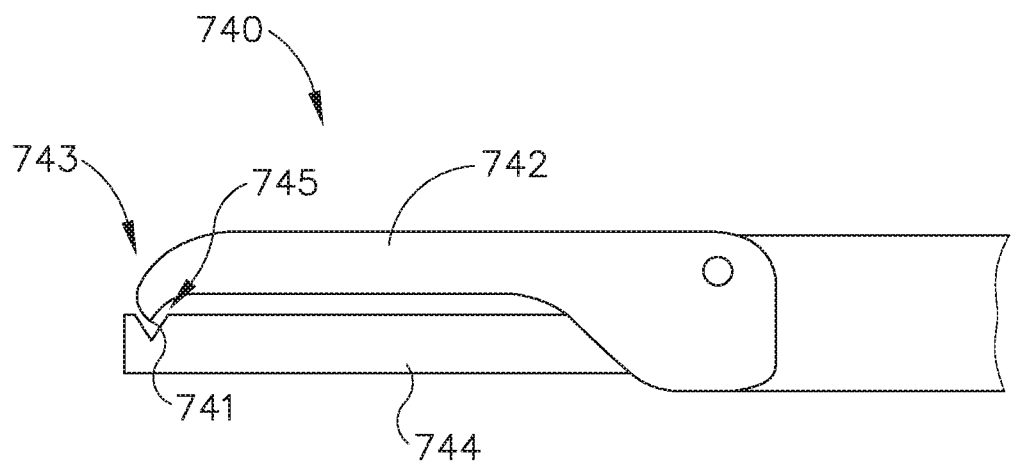
FIG. 17 depicts a side elevational view of yet another exemplary alternative clamp arm and blade tip operable to be used with the instrument of FIG. 1.

FIG. 17 shows yet another exemplary alternative end effector (740). End effector (740) comprises a clamp arm (742) and an ultrasonic blade (744). A distal tip of clamp arm (742) includes a claw-like profile (743) that terminates into a sharp tip (741) extending downwardly from clamp arm (742). A distal end of ultrasonic blade (744) includes a triangular pocket (745). Sharp tip (741) of clamp arm (742) is configured to be positioned within triangular pocket (745) of ultrasonic blade (744) when clamp arm (742) is in a closed position. A distal end of ultrasonic blade (744) extends beyond a distal end of clamp arm (742), which may provide a user with better access to thereby use the distal end of ultrasonic blade (744). Triangular pocket (745) and sharp tip (741) of clamp arm (742) may be used to prevent tissue and/or vessels from squeezing out of the distal end of end effector (740) as clamp arm (732) applies clamping force to the tissue and/or vessels. Ultrasonic blade (744) and/or clamp arm (742) may also be used to apply monopolar and/or bipolar RF energy to tissue. The distal end of ultrasonic blade (744) may be used to seal vessels that do not extend adequately from tissue to allow a user to clamp the vessel between clamp arm (742) and ultrasonic blade (744). In other words, the distal end of ultrasonic blade (744) may be used to provide spot sealing or "bleeder touch ups." The distal end of ultrasonic blade (744) may also be used to slice through tissue without having to clamp the tissue between clamp arm (742) and ultrasonic blade (744), in a back-scoring type of movement or otherwise. It should also be understood that pocket (745) may be used to cradle and cauterize/seal vessels and ducts, without transecting the tissue forming the vessels or ducts.

F. Sixth Exemplary Clamp Arm and Blade Tip

Figure 18:
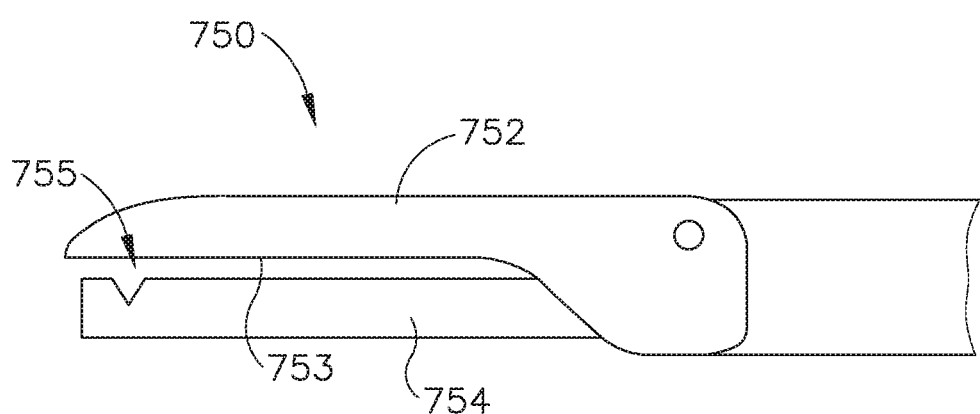
FIG. 18 depicts a side elevational view of yet another exemplary alternative clamp arm and blade tip operable to be used with the instrument of FIG. 1.

FIG. 18 shows yet another exemplary alternative end effector (750). End effector (750) comprises a clamp arm (752) and an ultrasonic blade (754). Clamp arm (752) includes a substantially flat bottom surface (753). A distal end of ultrasonic blade (754) includes a triangular pocket (755). It should be understood that triangular pocket (755) may be positioned anywhere along ultrasonic blade (754). It should further be understood that ultrasonic blade (754) may comprise a series triangular pockets (755) spaced along the length of ultrasonic blade (754). Triangular pocket (755) may be used to prevent tissue and/or vessels from squeezing out of the distal end of end effector (750) as clamp arm (752) applies clamping force to the tissue and/or vessels. Ultrasonic blade (754) and/or clamp arm (752) may also be used to apply monopolar and/or bipolar RF energy to tissue. It should also be understood that pocket (755) may be used to cradle and cauterize/seal vessels and ducts, without transecting the tissue forming the vessels or ducts.

G. Seventh Exemplary Clamp Arm and Blade Tip

Figure 19:
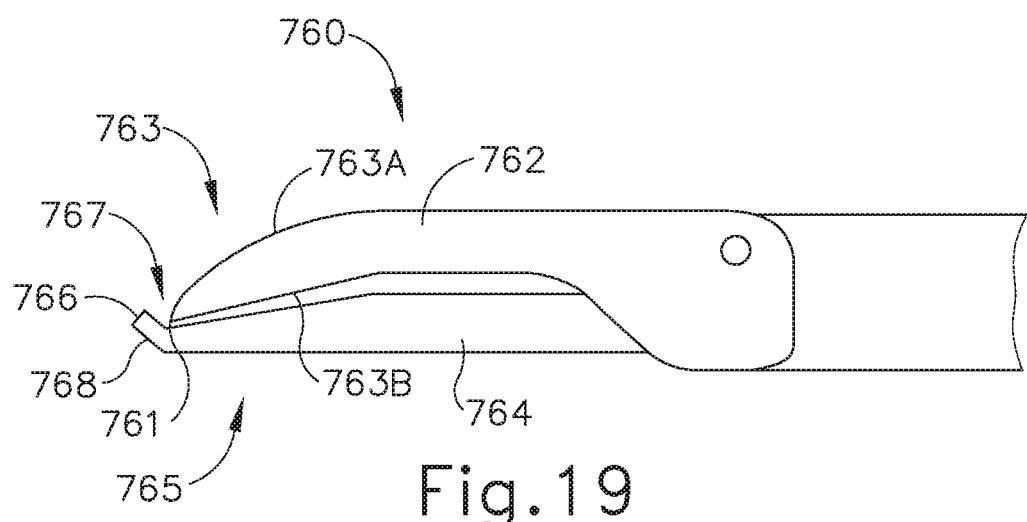
FIG. 19 depicts a side elevational view of yet another exemplary alternative clamp arm and blade tip operable to be used with the instrument of FIG. 1.

FIG. 19 shows yet another exemplary alternative end effector (760). End effector (760) comprises a clamp arm (762) and an ultrasonic blade (764). A distal end of clamp arm (762) comprises a profile (763) having a curved top surface (763A) and a planar bottom surface (763B) angled downwardly and distally. Profile (763) terminates into sharp tip (761). Sharp tip (761) extends generally downward and distally from the distal end of clamp arm (762). A distal end of ultrasonic blade (764) comprises a profile (765) having an angular top surface (765A) and a substantially flat bottom surface (765B). Profile (765) terminates into a rectangular tip (766). Angular top surface (765A) is sloped downwardly toward rectangular tip (766), which extends at an upward angle. Angular top surface (765A) of profile (765) defines a pocket (767) between the sloped surface and rectangular tip (766). Sharp tip (761) is configured to be positioned within pocket (767) of ultrasonic blade (764) when clamp arm (762) is in a closed position. Rectangular tip (766) extends beyond a sharp tip (761) of clamp arm (762), which may provide a user with better access to thereby use rectangular tip (766). A distal surface of rectangular tip (766) presents a flat planar surface (768). A sharp edge (769) is formed on a bottom surface of ultrasonic blade proximally of rectangular tip (766).

Pocket (767), rectangular tip (766), and sharp tip (761) of clamp arm (762) may be used to prevent tissue and/or vessels from squeezing out of the distal end of end effector (760) as clamp arm (762) applies clamping force to the tissue and/or vessels. Surface (768) of rectangular tip (766) may be used to seal vessels that do not extend adequately from tissue to allow a user to clamp the vessel between clamp arm (762) and ultrasonic blade (764). In other words, surface (768) may be used to provide spot sealing or "bleeder touch ups." Ultrasonic blade (764)—including surface (768) of rectangular tip (766)—and/or clamp arm (762) may be used to apply monopolar and/or bipolar RE energy to tissue. Sharp edge (769) may be used to slice through tissue without having to clamp the tissue between clamp arm (762) and ultrasonic blade (764), in a back-scoring type of movement or otherwise. It should also be understood that pocket (767) may be used to cradle and cauterize/seal vessels and ducts, without transecting the tissue forming the vessels or ducts.

H. Eighth Exemplary Clamp Arm and Blade Tip

Figure 20:
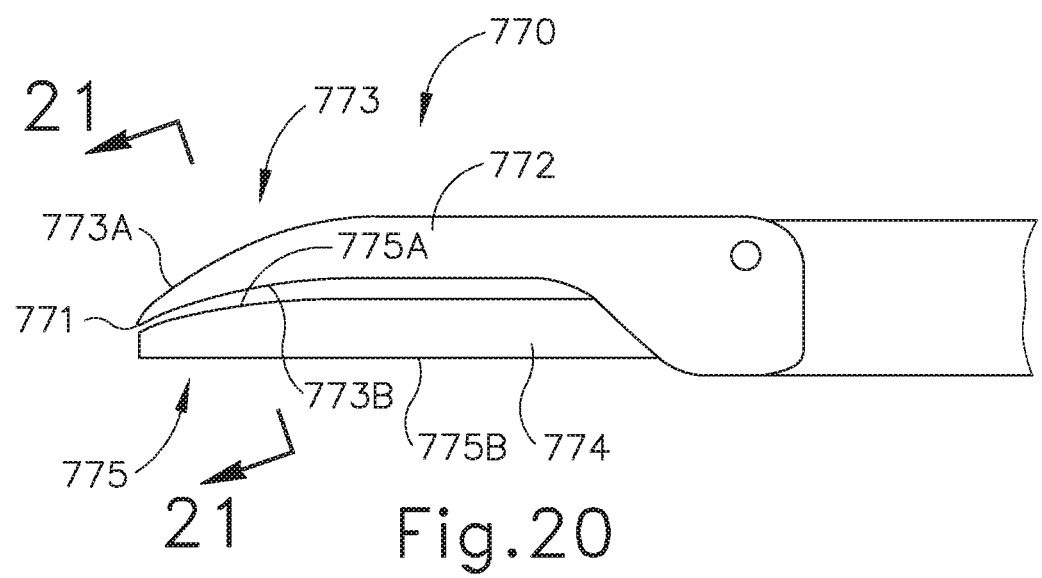
FIG. 20 depicts a side elevational view of yet another exemplary alternative clamp arm and blade tip operable to be used with the instrument of FIG. 1.
Figure 21:
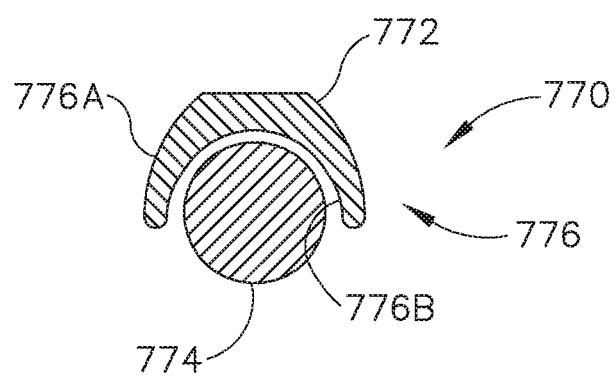
FIG. 21 depicts a cross-sectional view of the clamp arm and blade of FIG. 20 taken along line 21-21 of FIG. 20.

FIGS. 20 and 21 show yet another exemplary alternative end effector (770). End effector (770) comprises a clamp arm (772) and an ultrasonic blade (774). A distal end of clamp arm (772) comprises a curved profile (773) having a curved top surface (773A) and a curved bottom surface (773B). Curved bottom surface (773B) defines a convex profile. Curved profile (773) terminates into sharp tip (771). Sharp tip (771) extends generally downward and distally from the distal end of clamp arm (772). A distal end of ultrasonic blade (774) comprises a profile (775) having a curved top surface (775A) and a substantially flat bottom surface (775B). Curved top surface (775A) defines a concave profile that complements the convex profile of curved bottom surface (773B), as shown in FIG. 21. Clamp arm (772) comprises a cross-sectional profile (776) having a curved bottom surface (776B) and a generally curved top surface (776A). Curved bottom surface (776B) complements an exterior surface of ultrasonic blade (774).

Curved bottom surface (773B) of clamp arm (772) may be used to prevent tissue and/or vessels from squeezing out of the distal end of end effector (770) as clamp arm (772) applies clamping force to the tissue and/or vessels. Ultrasonic blade (774) and/or clamp arm (772) may also be used to apply monopolar and/or bipolar RF energy to tissue.

VI. Alternative Blade Tips

In some versions of instruments (10, 210, 310, 510, 610) discussed above, it may be desirable to provide ultrasonic blades (100, 200, 300, 500, 600) with geometric profiles that provide for improved dissection of tissue, more efficient cutting of tissue, and/or more efficient manipulation of tissue. FIGS. 22-47 show exemplary ultrasonic blades that may be used with any instrument (10, 210, 310, 510, 610) discussed above. The ultrasonic blades discussed below are configured to operate substantially similar to ultrasonic blades (100, 200, 300, 500, 600) discussed above, except for the differences discussed below. In particular, the ultrasonic blades discussed below are configured to vibrate at ultrasonic frequencies and thereby cut and/or seal the tissue.

A. First Exemplary Blade Tip

Figure 22:
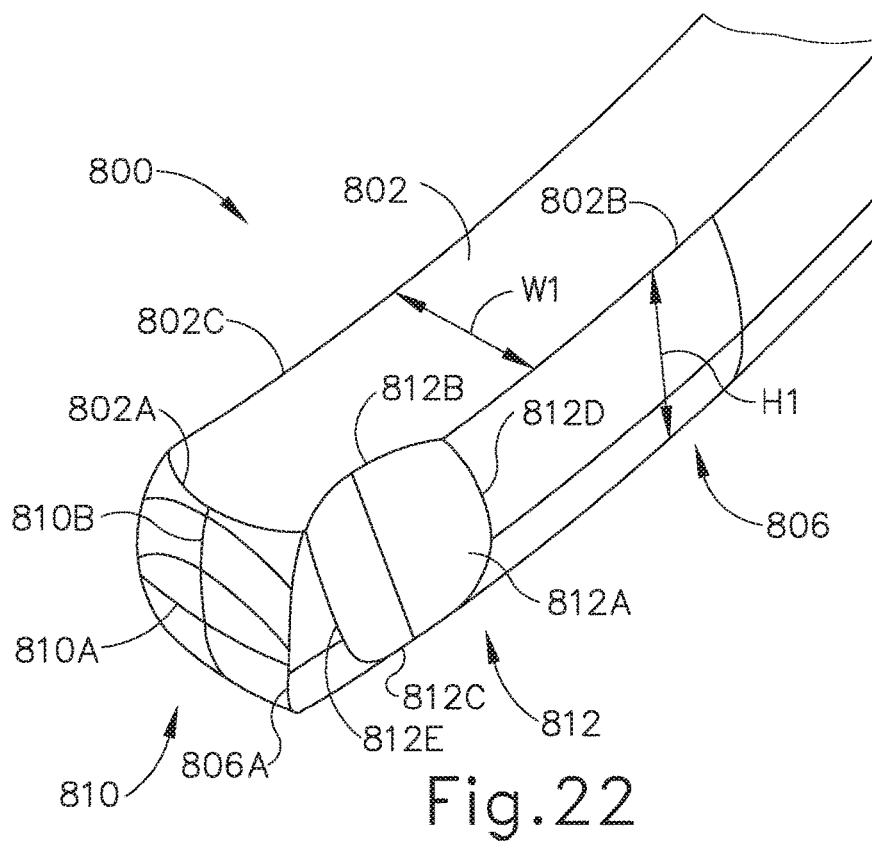
FIG. 22 depicts a perspective view of yet another exemplary alternative blade tip.
Figure 23:
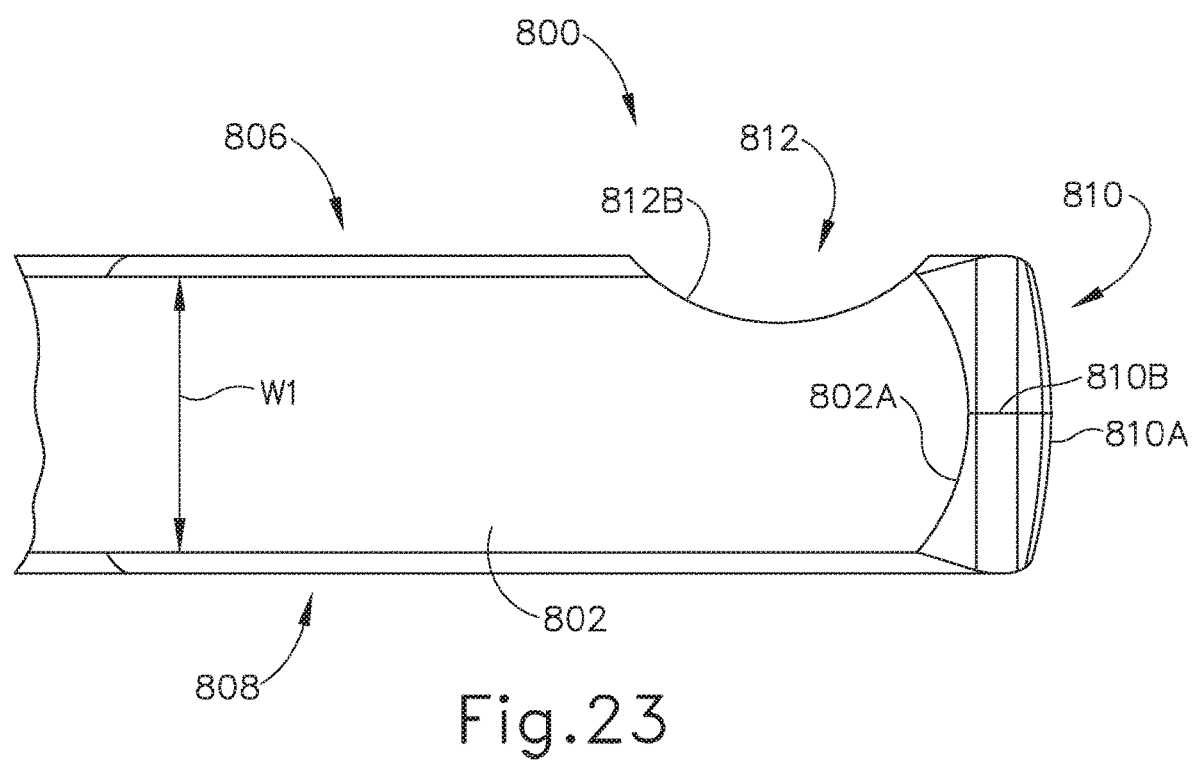
FIG. 23 depicts a top view of the blade tip of FIG. 22.
Figure 24:
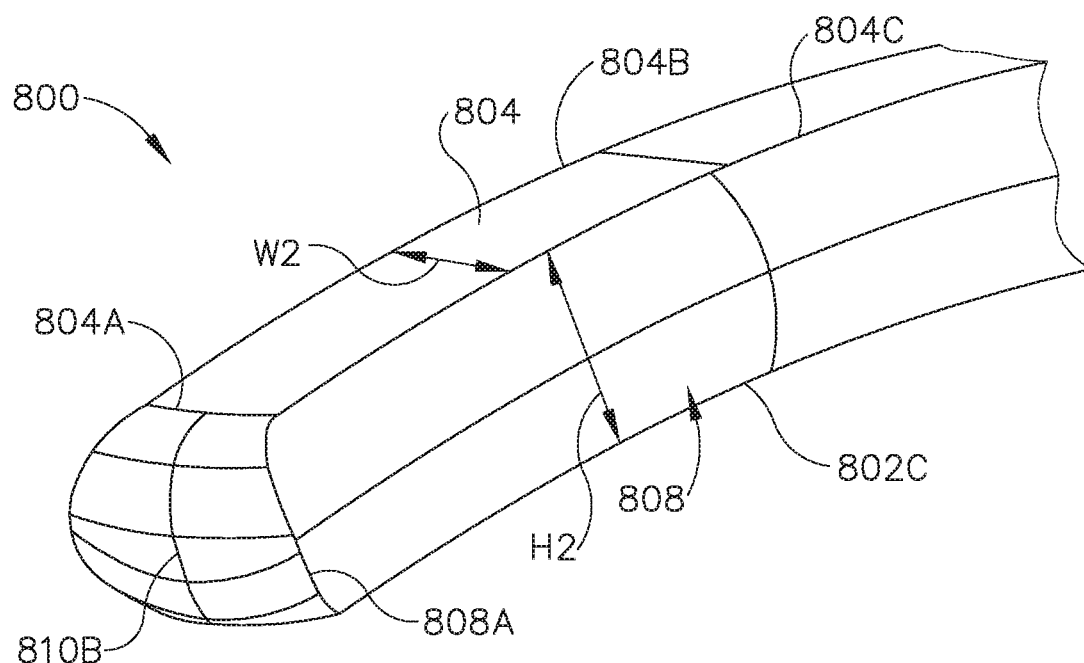
FIG. 24 depicts another perspective view of the blade tip of FIG. 22.
Figure 25:
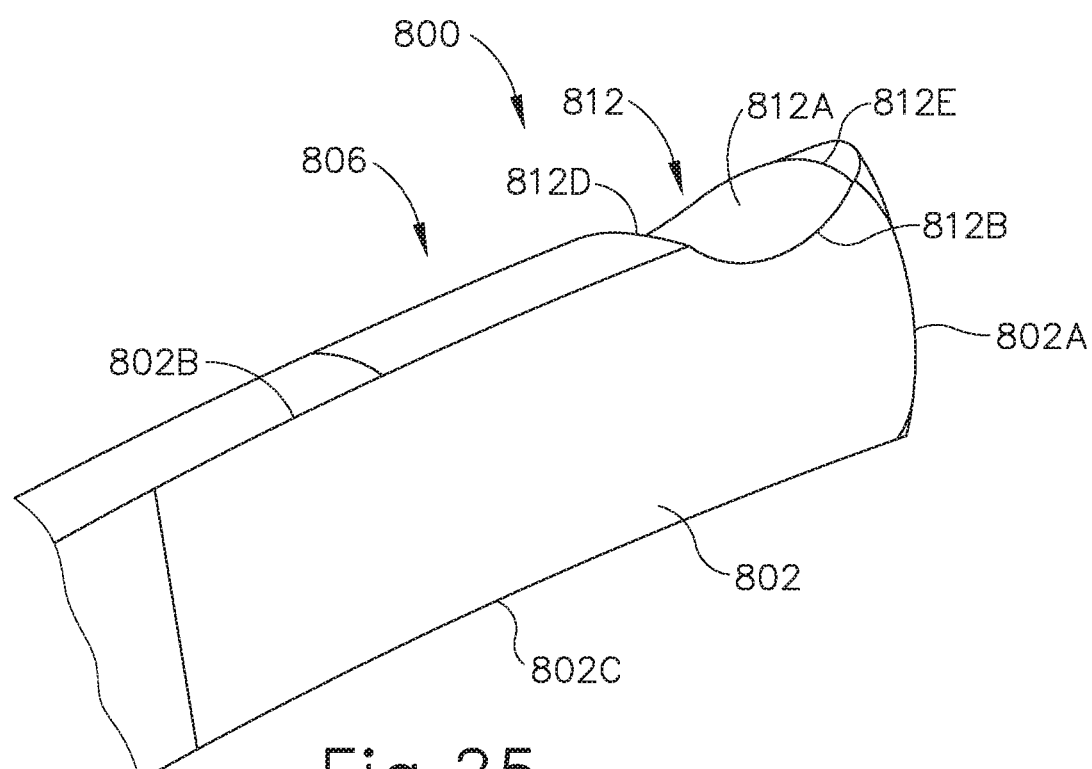
FIG. 25 depicts yet another perspective view of the blade tip of FIG. 22.

FIGS. 22-25 show an exemplary alternative ultrasonic blade tip (800). Blade tip (800) comprises a top surface (802), a bottom surface (804), a first side surface (806), and a second side surface (808). Blade tip (800) comprises a substantially straight plan view profile as best seen in FIG. 23 and a curved elevational view profile as best seen in FIGS. 22 and 24. A width (W1) of top surface (802) is greater than a width (W2) of bottom surface (804). Top surface (802) and bottom surface (804) are substantially flat across widths (W1, W2) although curved along a length of each top surface (802) and bottom surface (804). A distal end of top surface (802) terminates in a curved edge (802A) that is convex opening proximally. A distal end of bottom surface (804) terminates in a curved edge (804A) that is convex opening proximally.

A height (H1) of first side surface (806) and a height (H2) of second side surface (808) are substantially the same. First side surface (806) and second side surface (808) are curved across heights (H1, H2) although substantially flat along the length of each side surface (806, 808). The curvature across heights (H1, H2) is consistent along the length of each side surface (806, 808). A distal end of first side surface (806) terminates in a parabolic edge (806A) that is convex opening proximally. A distal end of second side surface (808) terminates in a parabolic edge (808A) that is convex opening proximally.

The substantially flat width (W1) of top surface (802) transitions to the curved surface of first side surface (806) along an edge (802B). The substantially flat width (W1) of top surface (802) transitions to the curved surface of second side surface (806) along an edge (802C). The substantially flat width (W2) of bottom surface (804) transitions to the curved surface of first side surface (806) along an edge (804B). The substantially flat width (W2) of bottom surface (804) transitions to the curved surface of second side surface (806) along an edge (804C).

Blade tip (800) further comprises a curved distal tip (810). Curved distal tip (810) comprises a curved plan view profile as best seen in FIG. 23 and a curved elevational view profile.

A horizontal distal most edge (810A) of curved distal tip (810) comprises a larger radial circumference than either curved edge (802A) or curved edge (804A). Curved distal tip (810) is oriented such that curved edge (802A) and curved edge (804A) are in substantially the same longitudinal position. A vertical distal most edge (810B) of curved distal tip (810) comprises a larger radial circumference than either parabolic edge (806A) or parabolic edge (808A).

The substantially flat width (W1) of top surface (802) transitions to the curved surfaces of curved distal tip (810) along curved edge (802A). The substantially flat width (W2) of bottom surface (804) transitions to the curved surfaces of curved distal tip (810) along curved edge (804A). The curved surface of first side surface (806) transitions to the curved surfaces of curved distal tip (810) along parabolic edge (806A). The curved surface of second side surface (808) transitions to the curved surfaces of curved distal tip (810) along parabolic edge (808A).

An arcuate cutout (812) is formed in a distal end of blade tip (800). Arcuate cutout (812) is formed in first side surface (806) and extends vertically from top surface (802) to bottom surface (804) such that a portion of each top surface (802) and bottom surface (804) is cutout in an arcuate fashion. Arcuate cutout (812) comprises a curved interior surface (812A). The substantially flat width (W1) of top surface (802) transitions to curved interior surface (812A) of arcuate cutout (812) along curved edge (812B). The substantially flat width (W2) of bottom surface (804) transitions to curved interior surface (812A) of arcuate cutout (812) along curved edge (812C). The curved surface of first side surface (806) transitions to curved interior surface (812A) of arcuate cutout (812) along curved edges (812D, 812E). As best seen in FIG. 22, a distal portion of first side surface (806) remains between parabolic edge (806A) and curved edge (812E).

Arcuate cutout (812) may be used to prevent tissue and/or vessels from squeezing out of the distal end of an end effector (not shown) as a clamp arm (not shown) applies clamping force to the tissue and/or vessels, Any surface (802, 804, 806, 808, 810, etc.) of blade tip (800) may be used to seal vessels that do not extend adequately from tissue (e.g., to provide spot sealing or "bleeder touch ups"). The edges of blade tip (800) (e.g. curved edges (812D, 812E), etc.) may be used to slice through tissue without having to clamp the tissue between the clamp arm and blade tip (800), in a back-scoring type of movement or otherwise. Blade tip (800) may also be used to apply monopolar and/or bipolar RF energy to tissue.

Blade tip (800) may be used with or without a pivoting clamp arm (e.g. clamp arm (44)). Such a clamp arm may pivot toward blade tip (800) to damp tissue against top surface (802), bottom surface (804), first side surface (806), and/or second side surface (808). Blade tip (800) may thus be oriented in any suitable orientation in relation to a pivoting clamp arm. It should therefore be understood that terms such as "top," "bottom," and "side," should not be read as limiting potential relationships between blade tip (800) and a pivoting clamp arm.

B. Second Exemplary Blade Tip

Figure 26:
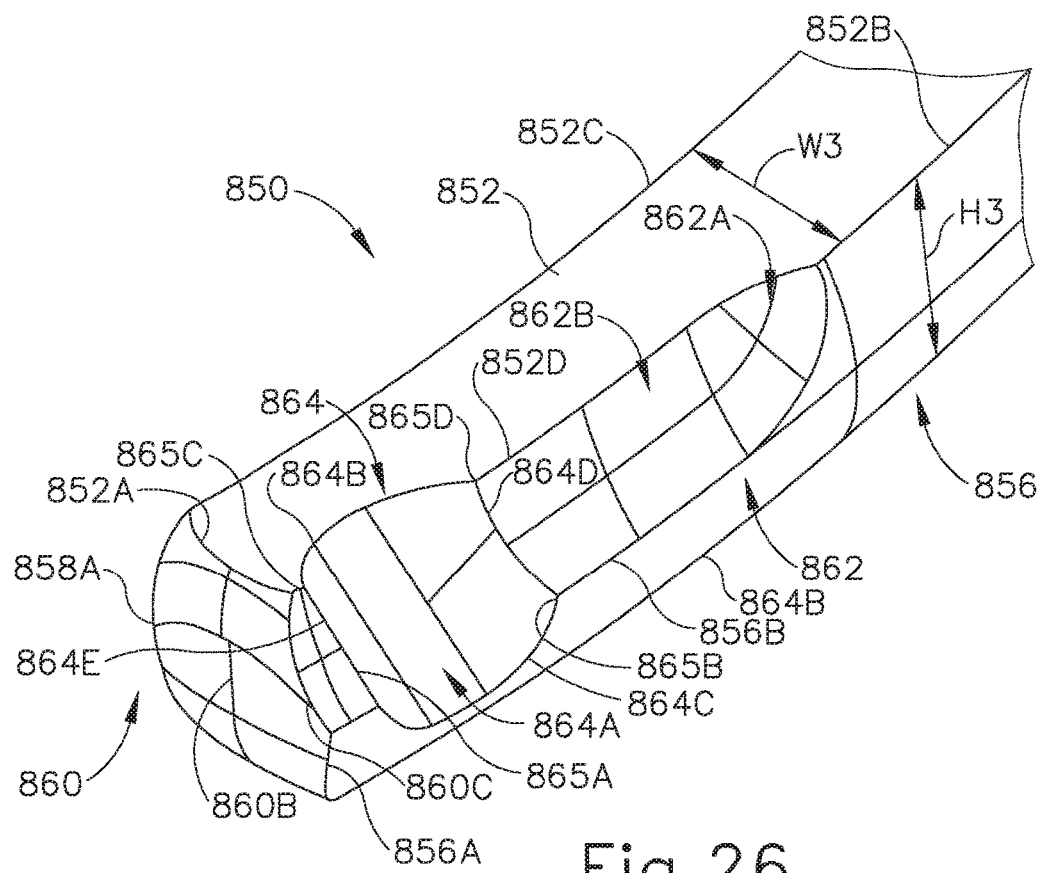
FIG. 26 depicts a perspective view of yet another exemplary alternative blade tip.
Figure 27:
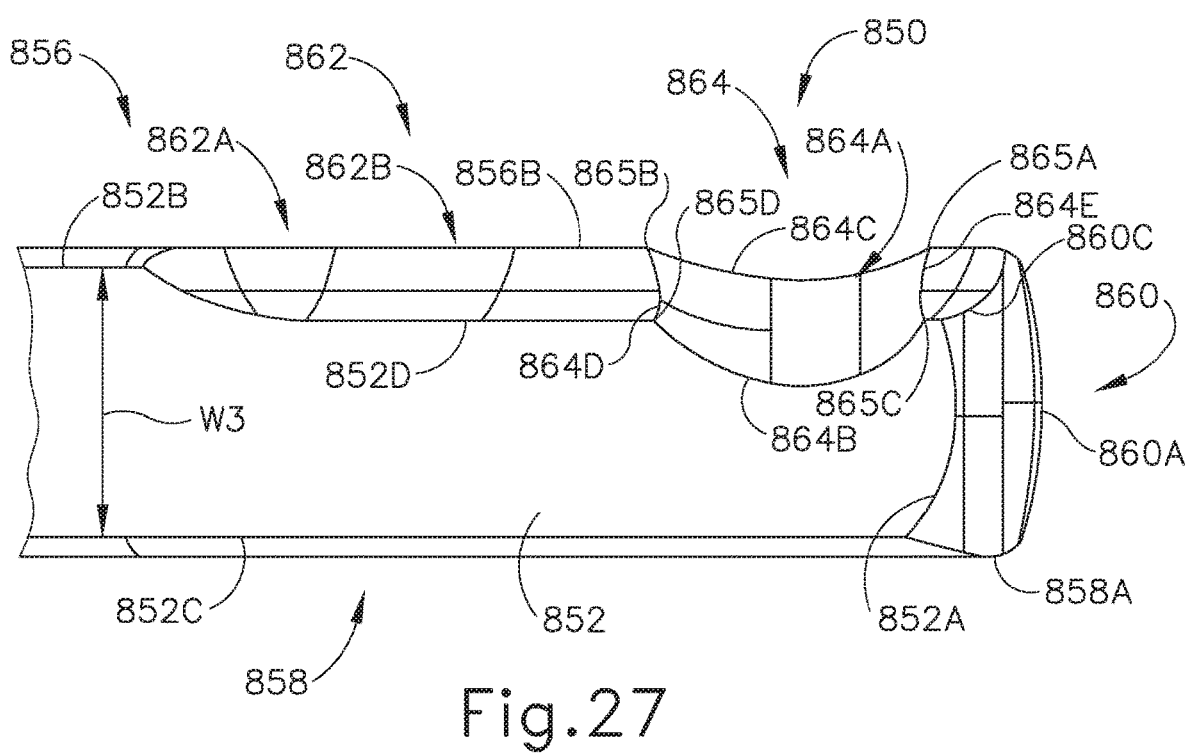
FIG. 27 depicts a top view of the blade tip of FIG. 26.
Figure 28:
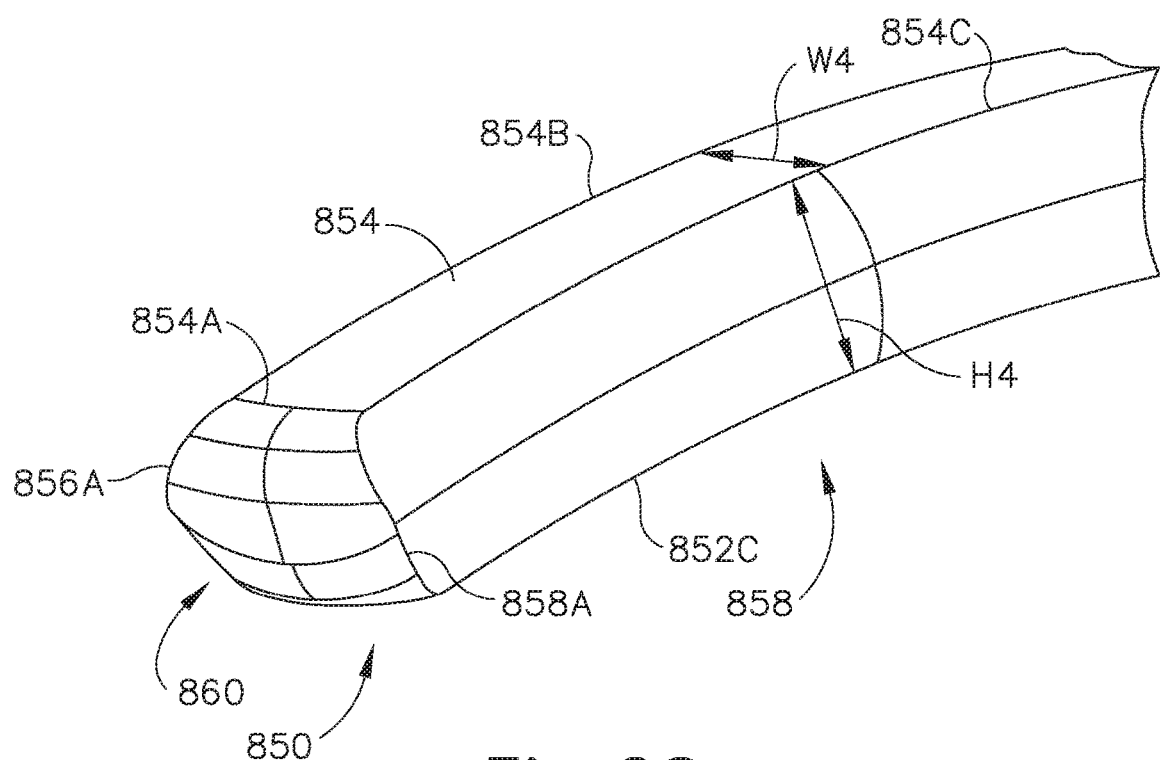
FIG. 28 depicts another perspective view of the blade tip of FIG. 26.
Figure 29:
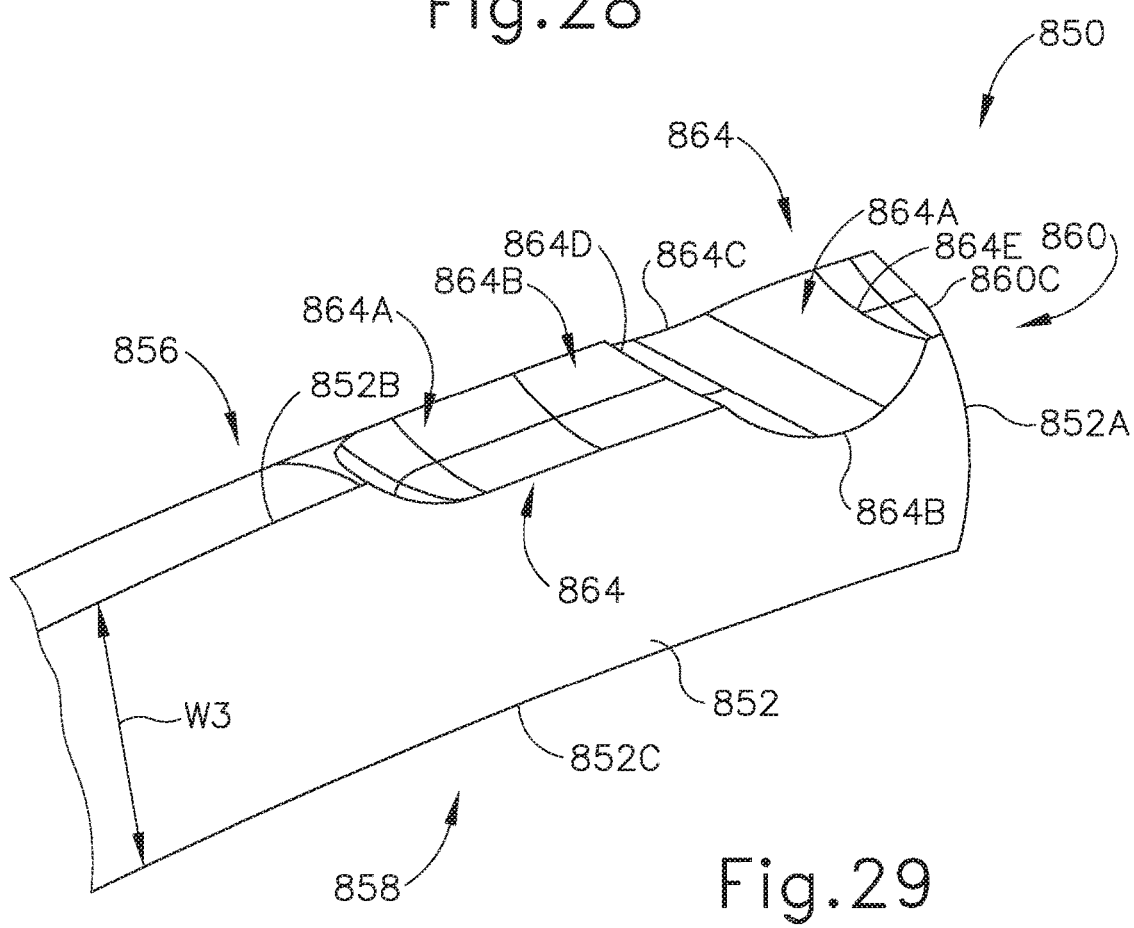
FIG. 29 depicts yet another perspective view of the blade tip of FIG. 26.

FIGS. 26-29 show an exemplary alternative blade tip (850). Blade tip (850) comprises a top surface (852), a bottom surface (854), a first side surface (856), and a second side surface (858). Blade tip (850) comprises a substantially straight plan view profile as best seen in FIG. 27 and a curved elevational view profile as best seen in FIGS. 26 and 28. A width (W3) of top surface (852) is greater than a width (W4) of bottom surface (854). Top surface (852) and bottom surface (854) are substantially flat across widths (W3, W4) although curved along a length of each top surface (852) and bottom surface (854). A distal end of top surface (852) terminates in a curved edge (852A) that is convex opening proximally. A distal end of bottom surface (854) terminates in a curved edge (854A) that is convex opening proximally.

A height (H3) of first side surface (856) and a height (H4) of second side surface (858) are substantially the same. First side surface (856) and second side surface (858) are curved across heights (H3, H4) although substantially flat along the length of each side surface (856, 858). The curvature across heights (H3, H4) is consistent along the length of each side surface (856, 858). A distal end of first side surface (856) terminates in a parabolic edge (856A) that is convex opening proximally. A distal end of second side surface (858) terminates in a parabolic edge (858A) that is convex opening proximally.

The substantially flat width (W3) of top surface (852) transitions to the curved surface of first side surface (856) along an edge (852B). The substantially flat width (W3) of top surface (852) transitions to the curved surface of second side surface (856) along an edge (852C). The substantially flat width (W4) of bottom surface (854) transitions to the curved surface of first side surface (856) along an edge (854B). The substantially flat width (W4) of bottom surface (854) transitions to the curved surface of second side surface (856) along an edge (854C).

Blade tip (850) further comprises a curved distal tip (860). Curved distal tip (860) comprises a curved plan view profile as best seen in FIG. 27 and a curved elevational view profile. A horizontal distal most edge (860A) of curved distal tip (860) comprises a larger radial circumference than either curved edge (852A) or curved edge (854A). A vertical distal most edge (860B) of curved distal tip (860) comprises a larger radial circumference than either parabolic edge (856A) or parabolic edge (858A).

The substantially flat width (W3) of top surface (852) transitions to the curved surfaces of curved distal tip (860) along curved edge (852A). The substantially flat width (W4) of bottom surface (854) transitions to the curved surfaces of curved distal tip (860) along curved edge (854A). The curved surface of first side surface (856) transitions to the curved surfaces of curved distal tip (860) along parabolic edge (856A). The curved surface of second side surface (858) transitions to the curved surfaces of curved distal tip (860) along parabolic edge (858A).

An elongate arcuate cutout (862) is formed in a distal end of blade tip (850). Elongate arcuate cutout (862) is formed in top surface (852) and first side surface (856) along edge (852B). Elongate arcuate cutout (862) originates from a point along edge (852B) and deepens along a curved surface (862A). Elongate arcuate cutout (862) comprises a curved interior surface (862B) that extends at a constant depth distally from the deepest portion of curved surface (862A) to the distal tip of blade tip (850). The substantially flat width (W3) of top surface (852) transitions to curved interior surfaces (862A, 862B) of elongate arcuate cutout (862) along an edge (852D). The curved surface of first side surface (856) transitions to curved interior surfaces (862A, 862B) of elongate arcuate cutout (862) along an edge (856B). The curved surfaces of curved distal tip (860) transition to the curved surfaces of curved interior surface (862A) of elongate arcuate cutout (862) along a curved edge (860C).

An arcuate cutout (864) is formed in a distal end of blade tip (850). Arcuate cutout (864) is formed in top surface (852) and first side surface (856) and extends angularly from top surface (802) to first side surface (856) such that a portion of each top surface (802) and first side surface (856) is cutout. Arcuate cutout (864) comprises a curved interior surface (864A). The substantially flat width (W3) of top surface (852) transitions to curved interior surface (864A) of arcuate cutout (864) along curved edge (864b). The curved surface of first side surface (856) transitions to curved interior surface (864A) of arcuate cutout (864) along curved edge (864C). Curved interior surface (862B) of elongate arcuate cutout (862) transitions to curved interior surface (864A) of arcuate cutout (864) along curved edges (864D, 864E). As best seen in FIG. 26, a distal portion of elongate arcuate cutout (862) remains between curved edge (864E) and curved edge (860C). A plurality of sharp tips (865A, 865B, 865C, 865D) are formed at the intersections of curved edges (864D, 864E) and curved edges (864B, 864C).

Arcuate cutouts (862, 864) may be used to prevent tissue and/or vessels from squeezing out of the distal end of an end effector (not shown) as a clamp arm (not shown) applies clamping force to the tissue and/or vessels. Any surface (852, 854, 856, 858, 860, etc.) of blade tip (850) may be used to seal vessels that do not extend adequately from tissue (e.g., to provide spot sealing or "bleeder touch ups"). The edges of blade tip (850) (e.g. curved edges (864D, 864E), etc.) may be used to slice through tissue without having to clamp the tissue between the clamp arm and blade tip (850), in a back-scoring type of movement or otherwise. The sharp tips of blade tip (850) (e.g. sharp tips (865A, 865B, 865C, 865D), etc.) may also be used to slice through tissue without having to clamp the tissue between the clamp arm and blade tip (850), in a back-scoring type of movement or otherwise. Blade tip (850) may also be used to apply monopolar and/or bipolar RE energy to tissue.

Blade tip (850) may be used with or without a pivoting clamp arm (e.g. clamp arm (44)). Such a clamp arm may pivot toward blade tip (850) to clamp tissue against top surface (852), bottom surface (854), first side surface (856), and/or second side surface (858). Blade tip (850) may thus be oriented in any suitable orientation in relation to a pivoting clamp arm. It should therefore be understood that terms such as "top," "bottom," and "side," should not be read as limiting potential relationships between blade tip (850) and a pivoting clamp arm.

C. Third Exemplary Blade Tip

Figure 30:
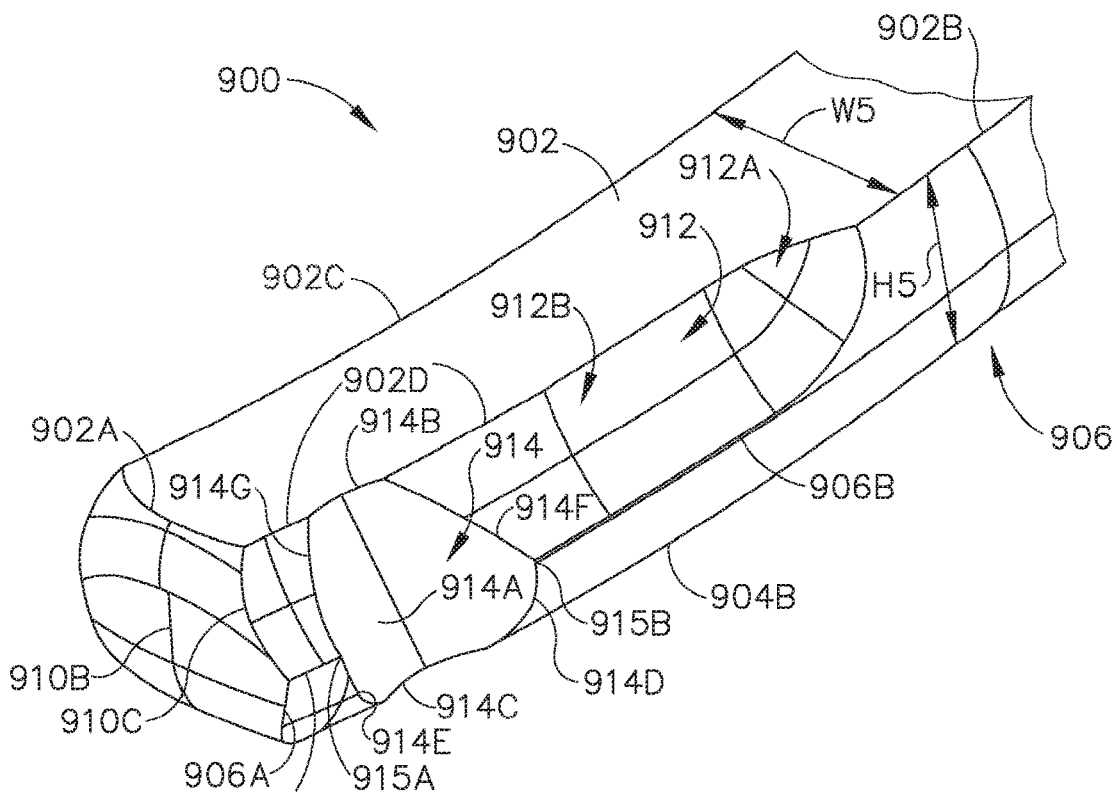
FIG. 30 depicts a perspective view of yet another exemplary alternative blade tip.
Figure 31:
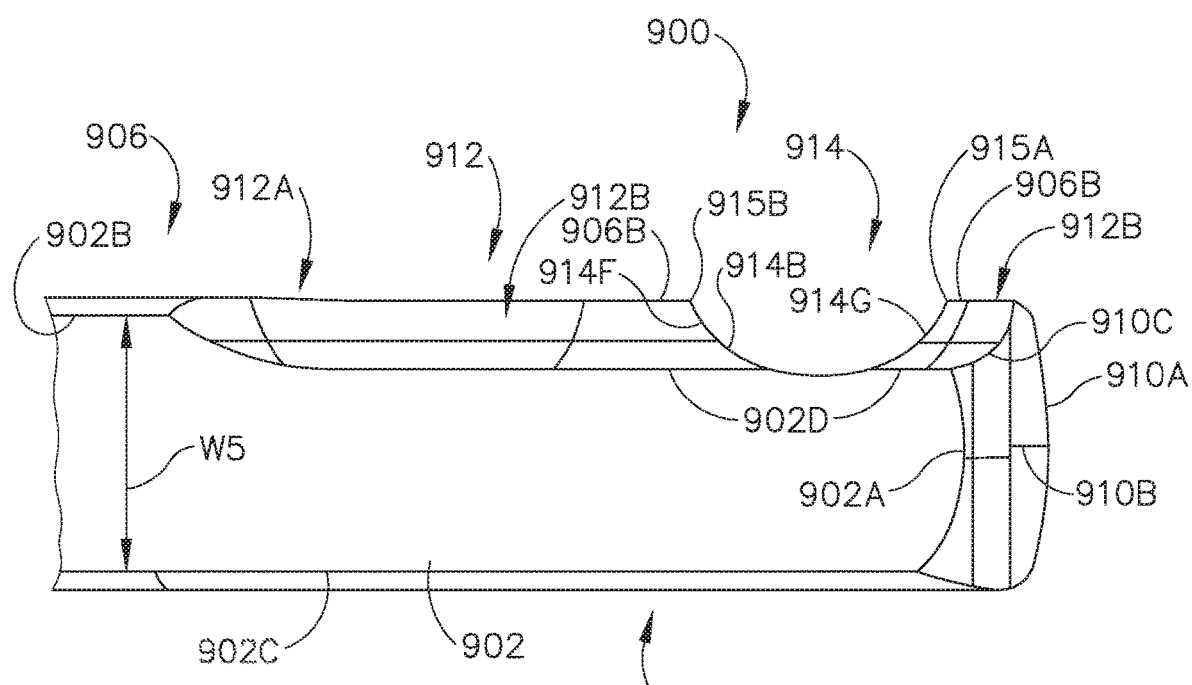
FIG. 31 depicts a top view of the blade tip of FIG. 30.
Figure 32:
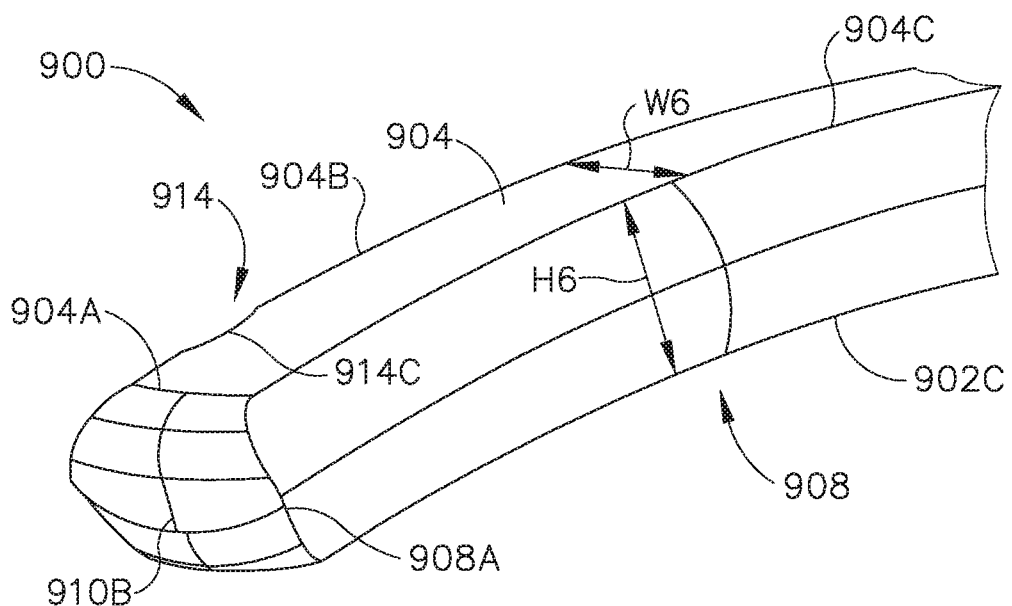
FIG. 32 depicts another perspective view of the blade tip of FIG. 30.
Figure 33:
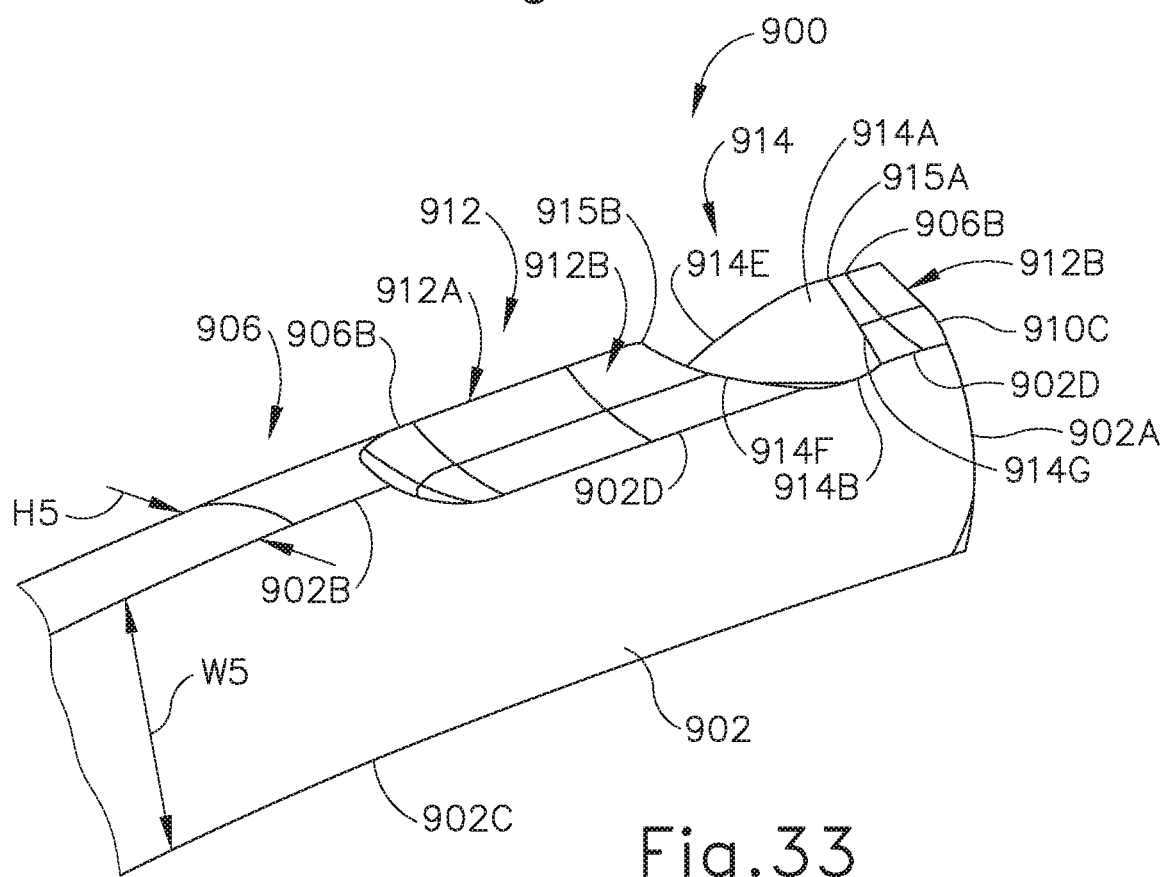
FIG. 33 depicts yet another perspective view of the blade tip of FIG. 30.

FIGS. 30-33 show an exemplary alternative blade tip (900). Blade tip (900) comprises a top surface (902), a bottom surface (904), a first side surface (906), and a second side surface (908). Blade tip (900) comprises a substantially straight plan view profile as best seen in FIG. 31 and a curved elevational view profile as best seen in FIGS. 30 and 32. A width (W5) of top surface (902) is greater than a width (W6) of bottom surface (904), Top surface (902) and bottom surface (904) are substantially flat across widths (W5, W6) although curved along a length of each top surface (902) and bottom surface (904). A distal end of top surface (902) terminates in a curved edge (902A) that is convex opening proximally. A distal end of bottom surface (904) terminates in a curved edge (904A) that is convex opening proximally.

A height (H5) of first side surface (906) and a height (116) of second side surface (908) are substantially the same. First side surface (906) and second side surface (908) are curved across heights (H5, H6) although substantially flat along the length of each side surface (906, 908). The curvature across heights (H5, H6) is consistent along the length of each side surface (906, 908). A distal end of first side surface (906) terminates in a parabolic edge (906A) that is convex opening proximally. A distal end of second side surface (908) terminates in a parabolic edge (908A) that is convex opening proximally.

The substantially flat width (W5) of top surface (902) transitions to the curved surface of first side surface (906) along an edge (902B). The substantially flat width (W5) of top surface (902) transitions to the curved surface of second side surface (906) along an edge (902C). The substantially flat width (W6) of bottom surface (904) transitions to the curved surface of first side surface (906) along an edge (904B). The substantially flat width (W6) of bottom surface (904) transitions to the curved surface of second side surface (906) along an edge (904C).

Blade tip (900) further comprises a curved distal tip (910). Curved distal tip (910) comprises a curved plan view profile as best seen in FIG. 31 and a curved elevational view profile. A horizontal distal most edge (910A) of curved distal tip (910) comprises a larger radial circumference than either curved edge (902A) or curved edge (904A). Curved distal tip (910) is oriented such that curved edge (902A) and curved edge (904A) are in substantially the same longitudinal position. A vertical distal most edge (910B) of curved distal tip (910) comprises a larger radial circumference than either parabolic edge (906A) or parabolic edge (908A).

The substantially flat width (W5) of top surface (902) transitions to the curved surfaces of curved distal tip (910) along curved edge (902A). The substantially flat width (W6) of bottom surface (904) transitions to the curved surfaces of curved distal tip (910) along curved edge (904A). The curved surface of first side surface (906) transitions to the curved surfaces of curved distal tip (910) along parabolic edge (906A). The curved surface of second side surface (908) transitions to the curved surfaces of curved distal tip (910) along parabolic edge (908A).

An elongate arcuate cutout (912) is formed in a distal end of blade tip (900). Elongate arcuate cutout (912) is formed in top surface (902) and first side surface (906) along edge (902B). Elongate arcuate cutout (912) originates from a point along edge (902B) and deepens along a curved surface (912A). Elongate arcuate cutout (912) comprises a curved interior surface (912B) that extends at a constant depth distally from the deepest portion of curved surface (912A) to the distal tip of blade tip (900). The substantially flat width (W5) of top surface (902) transitions to curved interior surfaces (912A, 912B) of elongate arcuate cutout (912) along an edge (902D). The curved surface of first side surface (906) transitions to curved interior surfaces (912A, 912B) of elongate arcuate cutout (912) along an edge (906B). The curved surfaces of curved distal tip (910) transition to the curved surfaces of curved interior surface (912A) of elongate arcuate cutout (912) along a curved edge (910C).

An arcuate cutout (914) is formed in a distal end of blade tip (900). Arcuate cutout (914) is formed in first side surface (906) and extends vertically from top surface (902), through elongate arcuate cutout (912), to bottom surface (904) such that a portion of each top surface (902), elongate arcuate cutout (912), and bottom surface (904) is cutout in an arcuate fashion when view in plan view as shown in FIG. 31. Arcuate cutout (914) comprises a curved interior surface (914A). The substantially flat width (W5) of top surface (902) transitions to curved interior surface (914A) of arcuate cutout (914) along curved edge (914B). The substantially flat width (W6) of bottom surface (904) transitions to curved interior surface (914A) of arcuate cutout (914) along curved edge (914C). The curved surface of first side surface (906) transitions to curved interior surface (914A) of arcuate cutout (914) along curved edges (914D, 914E). The curved surface of curved interior surface (912A) of elongate arcuate cutout (912) transitions to the curved surface of curved interior surface (914A) of arcuate cutout (914) along curved edges (914F, 914G). As best seen in FIG. 30, a distal portion of first side surface (906) remains between parabolic edge (906A) and curved edge (914E); and a distal portion of curved interior surface (912A) of elongate arcuate cutout (912) remains between curved, edge 910C) and curved edge (914G). A pair of sharp tips (915A, 915B) are formed at the intersections of curved edges (914D, 914E) and curved edges (9114F, 914G).

Arcuate cutouts (912, 914) may be used to prevent tissue and/or vessels from squeezing out of the distal end of an end effector (not shown) as a clamp arm (not shown) applies clamping force to the tissue and/or vessels. Any surface (902, 904, 906, 908, 910, etc.) of blade tip (900) may be used to seal vessels that do not extend adequately from tissue (e.g., to provide spot sealing or "bleeder touch ups"). The edges of blade tip (900) (e.g. curved edges (9114F, 914G), etc.) may be used to slice through tissue without having to clamp the tissue between the clamp arm and blade tip (900), in a back-scoring type of movement or otherwise. The sharp tips of blade tip (900) (e.g. sharp tips (915A, 915B), etc.) may also be used to slice through tissue without having to clamp the tissue between the clamp arm and blade tip (900), in a back-scoring type of movement or otherwise. Blade tip (900) may also be used to apply monopolar and/or bipolar RF energy to tissue.

Blade tip (900) may be used with or without a pivoting clamp arm (e.g. clamp arm (44)). Such a clamp arm may pivot toward blade tip (900) to damp tissue against top surface (902), bottom surface (904), first side surface (906), and/or second side surface (908). Blade tip (900) may thus be oriented in any suitable orientation in relation to a pivoting clamp arm. It should therefore be understood that terms such as "top," "bottom," and "side," should not be read as limiting potential relationships between blade tip (900) and a pivoting clamp arm.

D. Fourth Exemplary Blade Tip

Figure 34:
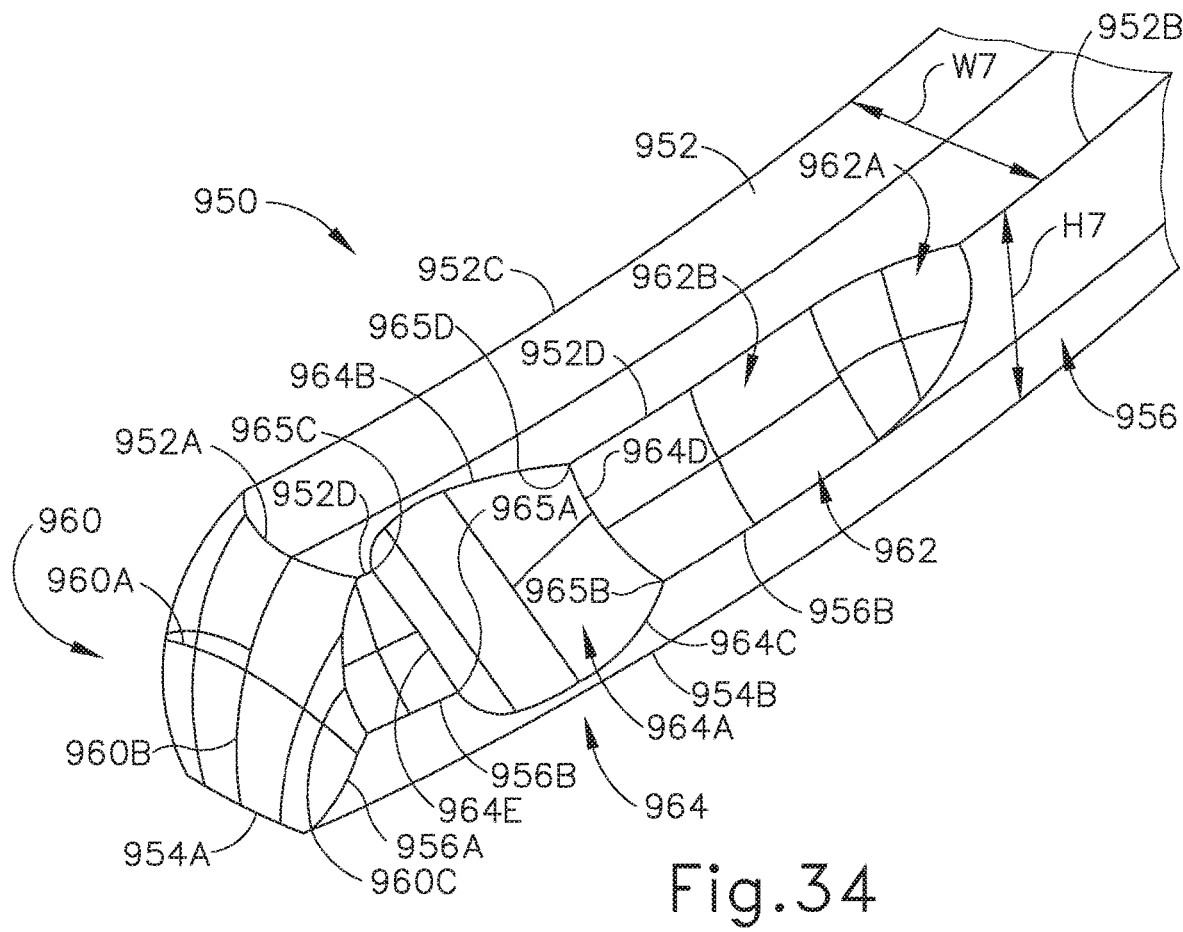
FIG. 34 depicts a perspective view of yet another exemplary alternative blade tip.
Figure 35:
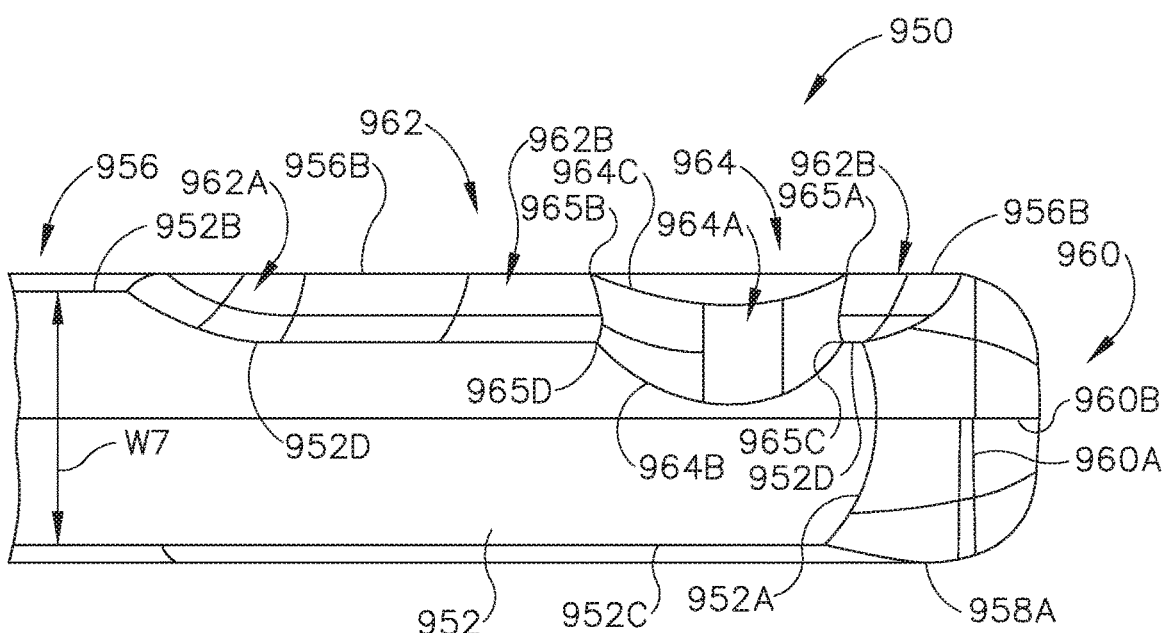
FIG. 35 depicts a top view of the blade tip of FIG. 34.
Figure 36:
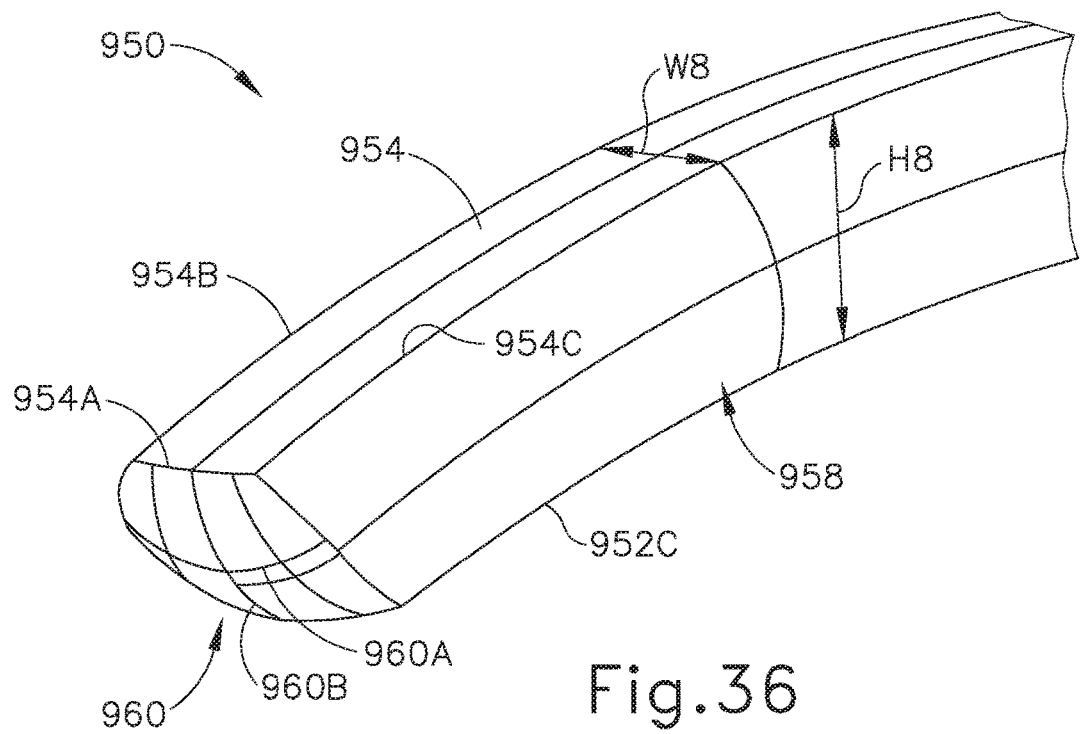
FIG. 36 depicts another perspective view of the blade tip of FIG. 34.
Figure 37:
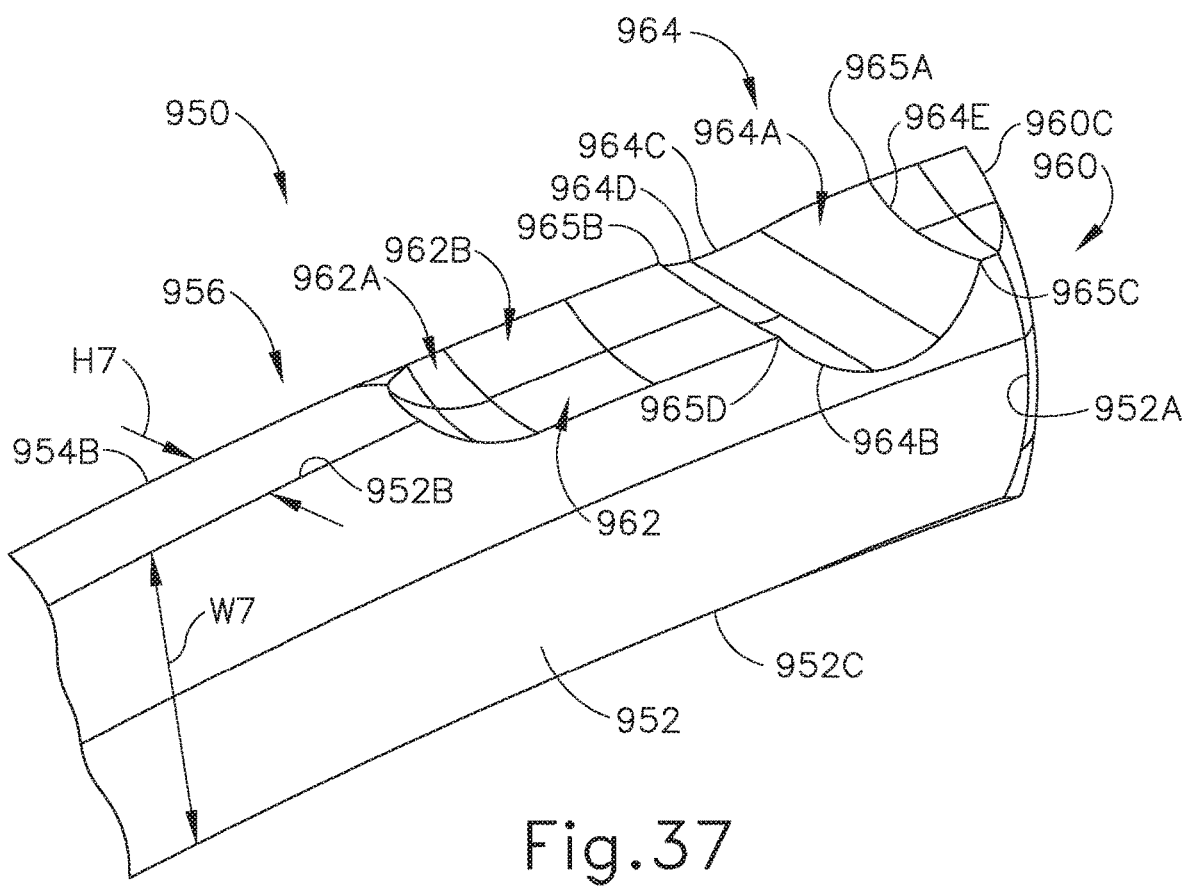
FIG. 37 depicts yet another perspective view of the blade tip of FIG. 34.
Figure 38:
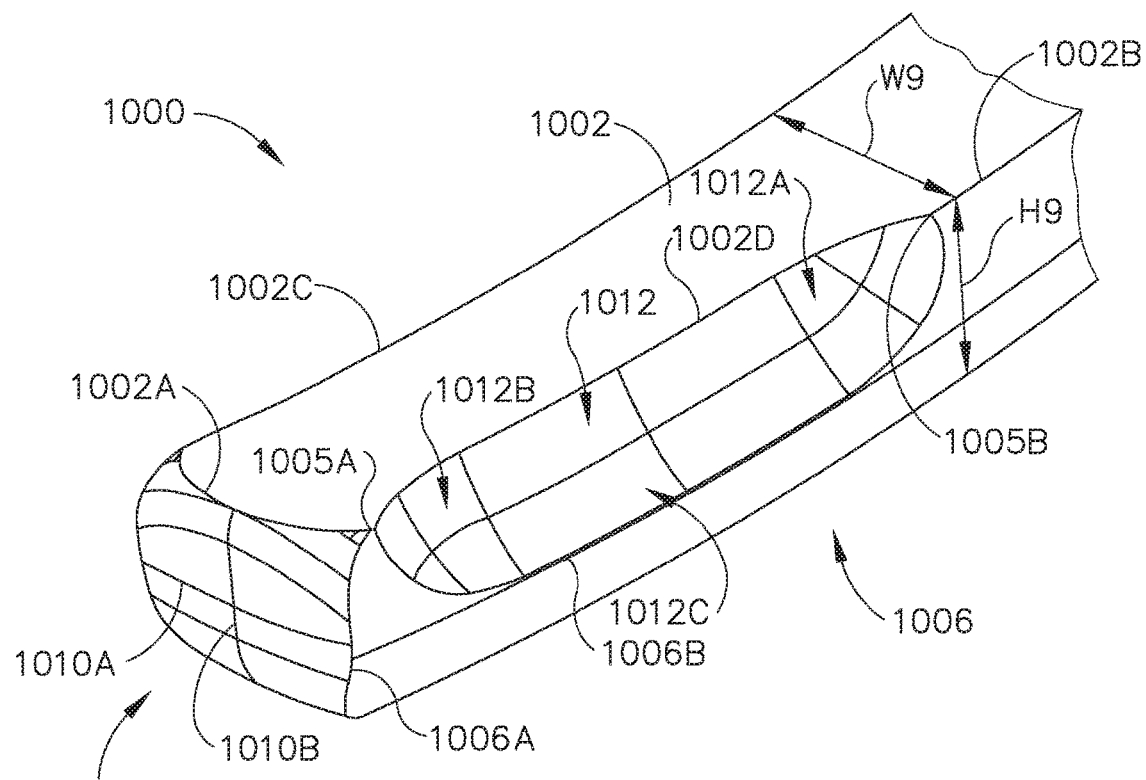
FIG. 38 depicts a perspective view of yet another exemplary alternative blade tip.

FIGS. 34-37 show an exemplary alternative blade tip (950). Blade tip (950) comprises a top surface (952), a bottom surface (954), a first side surface (956), and a second side surface (958). Blade tip (950) comprises a substantially straight plan view profile as best seen in FIG. 35 and a curved elevational view profile as best seen in FIGS. 34 and 36. A width (W7) of top surface (952) is greater than a width (W8) of bottom surface (954). Top surface (952) and bottom surface (954) are substantially flat across widths (W7, W8) although curved along a length of each top surface (952) and bottom surface (954). A distal end of top surface (952) terminates in a curved edge (952A) that is convex opening proximally. A distal end of bottom surface (954) terminates in a curved edge (954A) that is convex opening proximally. Curved edge (954A) has a greater radial circumference than curved edge (952A).

A height (H7) of first side surface (956) and a height (H8) of second side surface (958) are substantially the same. First side surface (956) and second side surface (958) are curved across heights (H7, H8) although substantially flat along the length of each side surface (956, 958). The curvature across heights (H7, H8) is consistent along the length of each side surface (956, 958). A distal end of first side surface (956) terminates in a parabolic edge (956A), A distal end of second side surface (958) terminates in a parabolic edge (958A).

The substantially flat width (W7) of top surface (952) transitions to the curved surface of first side surface (956) along an edge (952B). The substantially flat width (W7) of top surface (952) transitions to the curved surface of second side surface (956) along an edge (952C). The substantially flat width (W8) of bottom surface (954) transitions to the curved surface of first side surface (956) along an edge (954B), The substantially flat width (W8) of bottom surface (954) transitions to the curved surface of second side surface (956) along an edge (954C).

Blade tip (950) further comprises a curved distal tip (960). Curved distal tip (960) comprises a curved plan view profile and a curved elevational view profile. A horizontal distal most edge (960A) of curved distal tip (960) comprises a larger radial circumference than curved edge (952A) and a smaller radial circumference than curved edge (954A). A vertical distal most edge (960B) of curved distal tip (960) comprises a larger radial circumference than either parabolic edge (956A) or parabolic edge (958A), Curved distal tip (960) is oriented such that curved edge (952A) is in a more proximal position than curved edge (954A) such that curved edge (954A) forms a relatively sharp tip at the end of blade tip (950). Curved distal tip (960) is oriented such that curved edge (952A) and curved edge (954A) are in substantially the same longitudinal position.

The substantially flat width (W7) of top surface (952) transitions to the curved surfaces of curved distal tip (960) along curved edge (952A). The substantially flat width (W8) of bottom surface (954) transitions to the curved surfaces of curved distal tip (960) along curved edge (954A). The curved surface of first side surface (956) transitions to the curved surfaces of curved distal tip (960) along curved edge (956A). The curved surface of second side surface (958) transitions to the curved surfaces of curved distal tip (960) along curved edge (958A).

An elongate arcuate cutout (962) is formed in a distal end of blade tip (950). Elongate arcuate cutout (962) is formed in top surface (952) and first side surface (956) along edge (952B). Elongate arcuate cutout (962) originates from a point along edge (952B) and deepens along a curved surface (962A). Elongate arcuate cutout (962) comprises a curved interior surface (962B) that extends at a constant depth distally from the deepest portion of curved surface (962A) to the distal tip of blade tip (950). The substantially flat width (W7) of top surface (952) transitions to curved interior surfaces (962A, 962B) of elongate arcuate cutout (962) along an edge (952D). The curved surface of first side surface (956) transitions to curved interior surfaces (962A, 962B) of elongate arcuate cutout (962) along an edge (956B). The curved surfaces of curved distal tip (960) transition to the curved surfaces of curved interior surface (962A) of elongate arcuate cutout (962) along a curved edge (960C).

An arcuate cutout (964) is formed in a distal end of blade tip (950). Arcuate cutout (964) is formed in first side surface (956) and extends angularly from top surface (952), through elongate arcuate cutout (962), to first side surface (956). Arcuate cutout (964) comprises a curved interior surface (964A). The substantially flat width (W7) of top surface (952) transitions to curved interior surface (964A) of arcuate cutout (964) along curved edge (964B). The curved surface of first side surface (956) transitions to curved interior surface (964A) of arcuate cutout (964) along curved edge (964C). The curved surface of curved interior surface (962A) of elongate arcuate cutout (962) transitions to the curved surface of curved interior surface (964A) of arcuate cutout (964) along curved edges (964D, 964E). As best seen in 34, a distal portion of first side surface (956) remains between curved edge (956A) and curved edge (954C); and a distal portion of curved interior surface (962A) of elongate arcuate cutout (962) remains between curved edge (960C) and curved edge (964E). A plurality of sharp tips (965A, 965B, 965C, 965D) are formed at the intersections of curved edges (964B, 964C) and curved edges (964D, 964E).

Arcuate cutouts (962, 964) may be used to prevent tissue and/or vessels from squeezing out of the distal end of an end effector (not shown) as a clamp arm (not shown) applies clamping force to the tissue and/or vessels. Any surface (952, 954, 956, 958, 960, etc.) of blade tip (950) may be used to seal vessels that do not extend adequately from tissue (e.g., to provide spot sealing or "bleeder touch ups"). The edges of blade tip (950) (e.g. curved edges (964D, 964E), etc.) may be used to slice through tissue without having to clamp the tissue between the clamp arm and blade tip (950), in a back-scoring type of movement or otherwise. The sharp tips of blade tip (950) (e.g. sharp tips (965A, 965B, 965C, 965D), etc.) may also be used to slice through tissue without having to clamp the tissue between the clamp arm and blade tip (950), in a hack-scoring type of movement or otherwise. Blade tip (950) may also be used to apply monopolar and/or bipolar RE energy to tissue.

Blade tip (950) may be used with or without a pivoting clamp arm (e.g. clamp arm (44)). Such a clamp arm may pivot toward blade tip (950) to clamp tissue against top surface (952), bottom surface (954), first side surface (956), and/or second side surface (958). Blade tip (950) may thus be oriented in any suitable orientation in relation to a pivoting clamp arm. It should therefore be understood that terms such as "top," "bottom," and "side," should not be read as limiting potential relationships between blade tip (950) and a pivoting clamp arm.

E. Fifth Exemplary Blade Tip

FIGS. 38-41 show an exemplary alternative blade tip (1000). Blade tip (1000) comprises a top surface (1002), a bottom surface (1004), a first side surface (1006), and a second side surface (1008). Blade tip (1000) comprises a substantially straight plan view profile as best seen in FIG. 35 and a curved elevational view profile as best seen in FIGS. 34 and 36. A width (W9) of top surface (1002) is greater than a width (W10) of bottom surface (1004). Top surface (1002) and bottom surface (1004) are substantially flat across widths (W9, W10) although curved along a length of each top surface (1002) and bottom surface (1004). A distal end of top surface (1002) terminates in a curved edge (1002A) that is convex opening proximally. A distal end of bottom surface (1004) terminates in a curved edge (1004A) that is convex opening proximally. Curved edge (1004A) has a greater radial circumference than curved edge (1002A).

A height (H9) of first side surface (1006) and a height (H10) of second side surface (1008) are substantially the same. First side surface (1006) and second side surface (1008) are curved across heights (H9, H10) although substantially flat along the length of each side surface (1006, 1008). The curvature across heights (H9, H10) is consistent along the length of each side surface (1006, 1008). A distal end of first side surface (1006) terminates in a parabolic edge (1006A). A distal end of second side surface (1008) terminates in a parabolic edge (1008A).

The substantially flat width (W9) of top surface (1002) transitions to the curved surface of first side surface (1006) along an edge (1002B). The substantially flat width (W9) of top surface (1002) transitions to the curved surface of second side surface (1006) along an edge (1002C), The substantially flat width (W10) of bottom surface (1004) transitions to the curved surface of first side surface (1006) along an edge (1004B). The substantially flat width (W10) of bottom surface (1004) transitions to the curved surface of second side surface (1006) along an edge (1004C).

Figure 39:
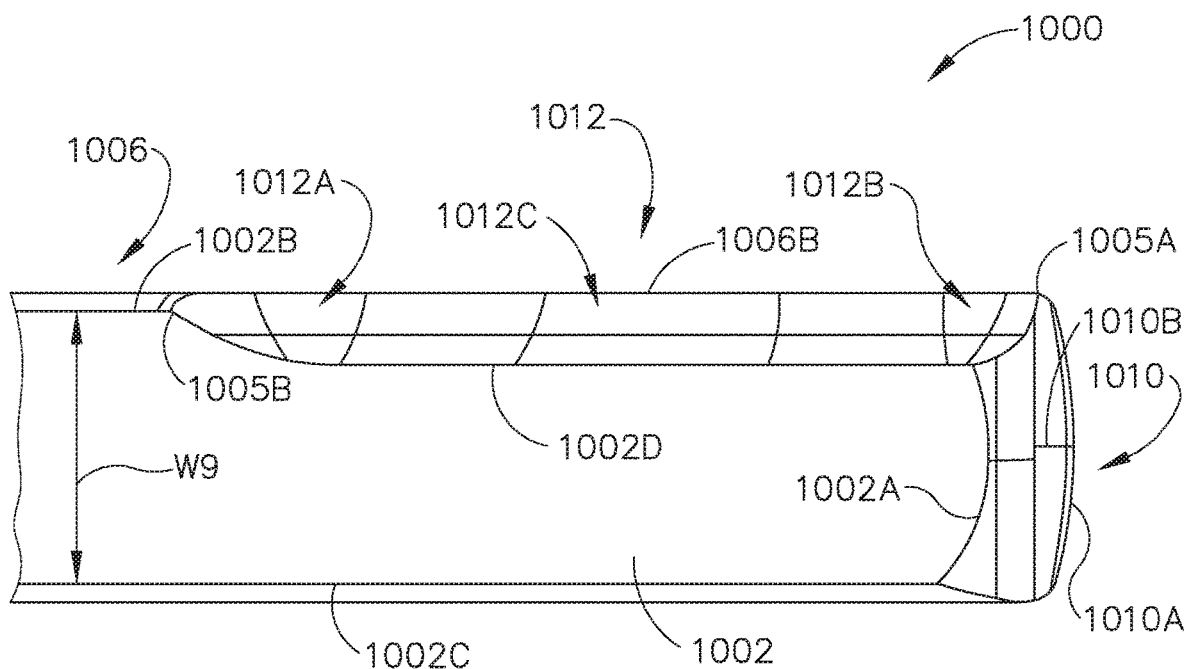
FIG. 39 depicts a top view of the blade tip of FIG. 38.
Figure 40:
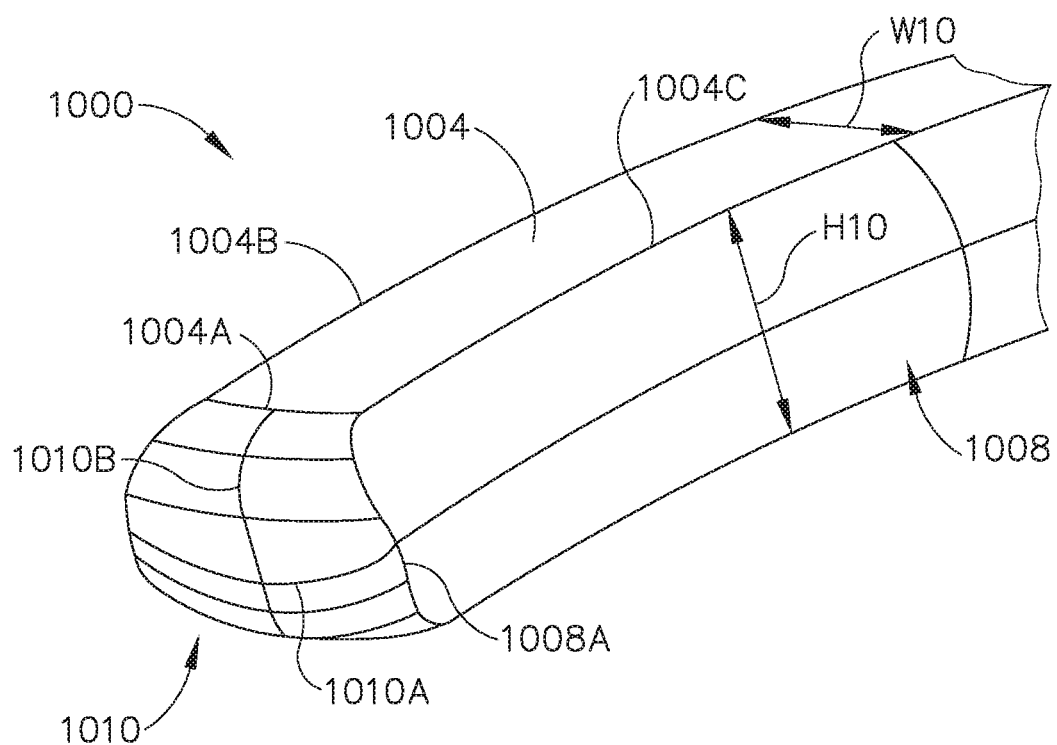
FIG. 40 depicts another perspective view of the blade tip of FIG. 38.
Figure 41:
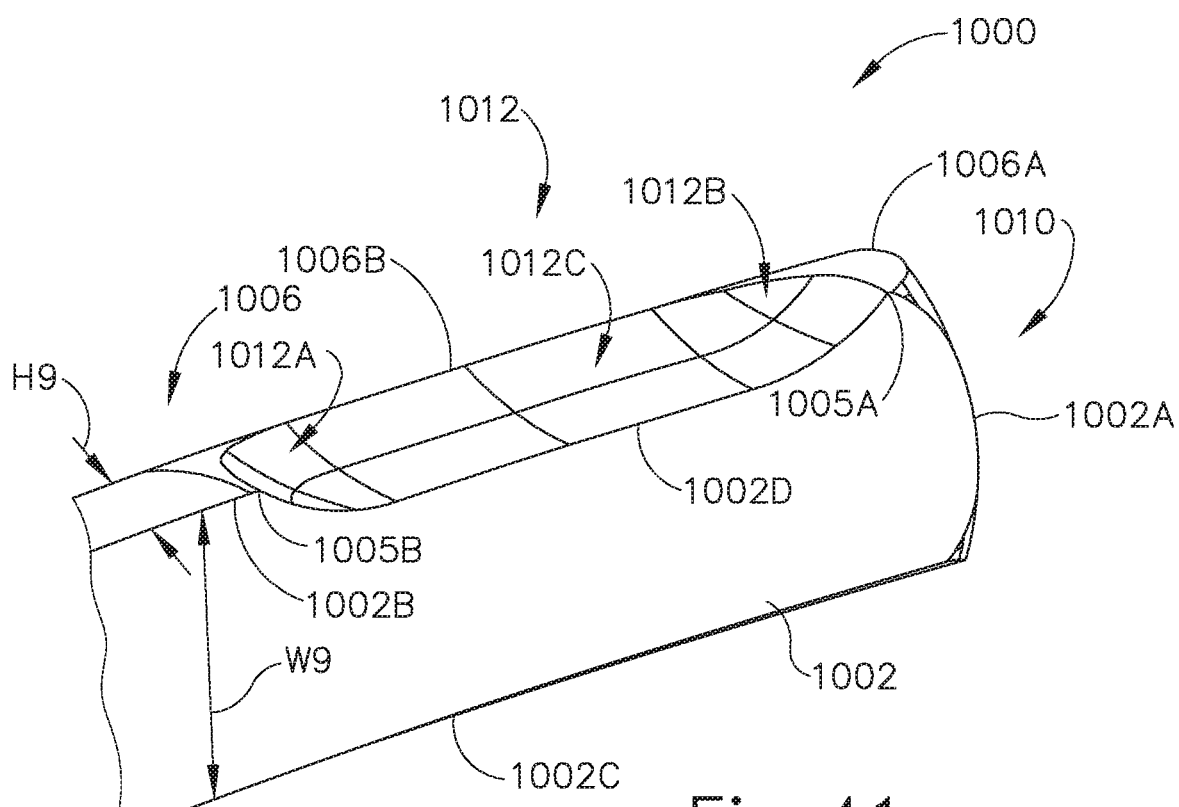
FIG. 41 depicts yet another perspective view of the blade tip of FIG. 38.

Blade tip (1000) further comprises a curved distal tip (1010). Curved distal tip (1010) comprises a curved plan view profile as best seen in FIG. 39 and a curved elevational view profile. A horizontal distal most edge (1010A) of curved distal tip (1010) comprises a larger radial circumference than curved edge (1002A) and a smaller radial circumference than curved edge (1004A). Curved distal tip (1010) is oriented such that curved edge (1002A) and curved edge (1004A) are in substantially the same longitudinal position. A vertical distal most edge (1010B) of curved distal tip (1010) comprises a larger radial circumference than either parabolic edge (1006A) or parabolic edge (1008A).

The substantially flat width (W9) of top surface (1002) transitions to the curved, surfaces of curved distal tip (1010) along curved edge (1002A). The substantially flat width (W10) of bottom surface (1004) transitions to the curved surfaces of curved distal tip (1010) along curved edge (1004A). The curved surface of first side surface (1006) transitions to the curved surfaces of curved distal tip (1010) along curved edge (1006A). The curved surface of second side surface (1008) transitions to the curved surfaces of curved distal tip (1010) along curved edge (1008A).

An elongate arcuate cutout (1012) is formed in a distal end of blade tip (1000). Elongate arcuate cutout (1012) is formed in top surface (1002) and first side surface (1006) along edge (1002B). Elongate arcuate cutout (1012) originates from a proximal point along edge (1002B) and deepens along a curved surface (1012A). Elongate arcuate cutout (1012) terminates at a distal point along edge (1002B) and deepens along a curved surface (1012B). Elongate arcuate cutout (1012) comprises a curved interior surface (1012C) that extends at a constant depth distally from the deepest portion of curved surface (1012A) to the deepest portion of cured surface (1012B). The substantially flat width (W9) of top surface (1002) transitions to curved interior surfaces (1012A, 1012B, 1012C) of elongate arcuate cutout (1012) along an edge (1002D). The curved surface of first side surface (1006) transitions to curved interior surfaces (1012A, 1012B, 1012C) of elongate arcuate cutout (1012) along an edge (1006B). A pair of sharp tips (1005A, 1005B) are formed at the intersections of edge (1002D) and edge (1006B).

Elongate arcuate cutout (1012) may be used to prevent tissue and/or vessels from squeezing out of the distal end of an end effector (not shown) as a clamp arm (not shown) applies clamping force to the tissue and/or vessels. Any surface (1002, 1004, 1006, 1008, 1010, etc.) of blade tip (1000) may be used to seal vessels that do not extend adequately from tissue (e.g., to provide spot sealing or "bleeder touch ups"). The edges of blade tip (1000) (e.g. edges (1002D, 1006B), etc.) may be used to slice through tissue without having to clamp the tissue between the clamp arm and blade tip (1000), in a back-scoring type of movement or otherwise. The sharp tips of blade tip (1000) (e.g. sharp tips (1005A, 1005B), etc.) may also be used to slice through tissue without having to clamp the tissue between the clamp arm and blade tip (1000), in a back-scoring type of movement or otherwise. Blade tip (1000) may also be used to apply monopolar and/or bipolar RF energy to tissue.

Blade tip (1000) may be used with or without a pivoting clamp arm (e.g. clamp arm (44)). Such a clamp arm may pivot toward blade tip (1000) to clamp tissue against top surface (1002), bottom surface (1004), first side surface (1006), and/or second side surface (1008). Blade tip (1000) may thus be oriented in any suitable orientation in relation to a pivoting clamp arm. It should therefore be understood that terms such as "top," "bottom," and "side," should not be read as limiting potential relationships between blade tip (1000) and a pivoting clamp arm.

F. Sixth Exemplary Blade Tip

Figure 44:
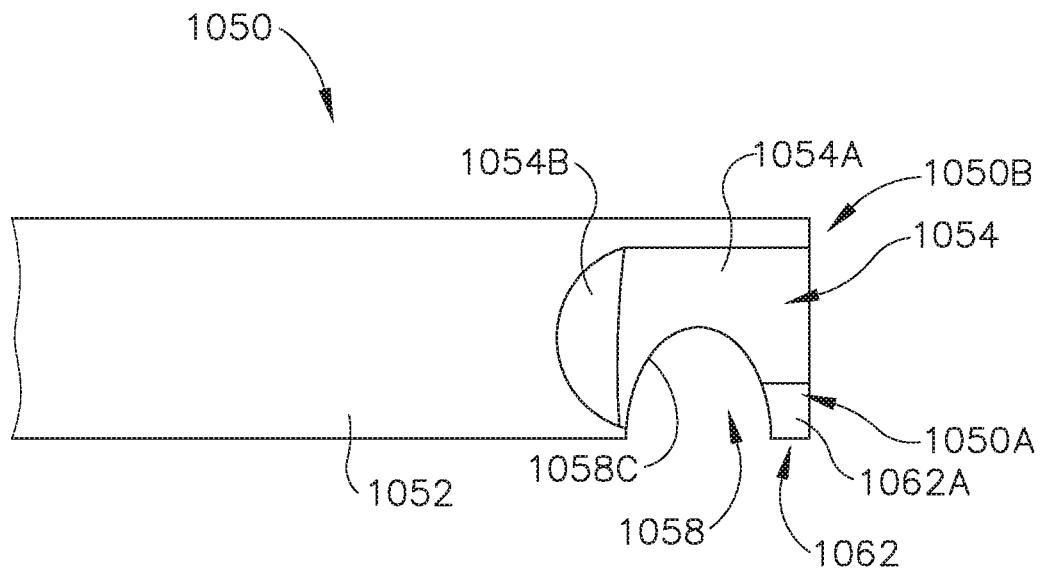
FIG. 44 depicts a top view of the blade tip of FIG. 43.
Figure 45:
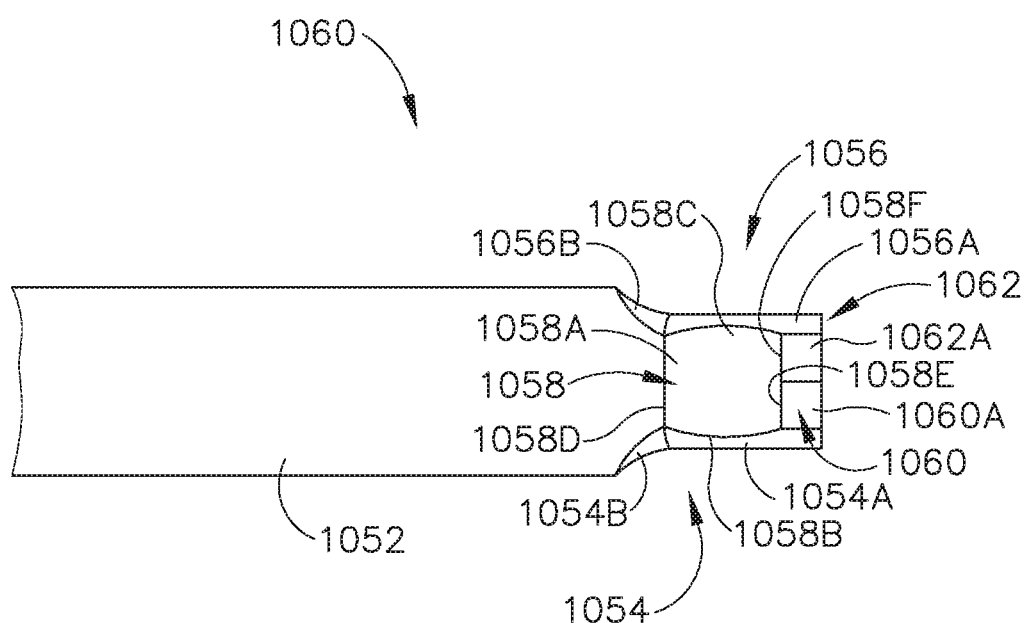
FIG. 45 depicts a side elevational view of the blade tip of FIG. 43.
Figure 46:
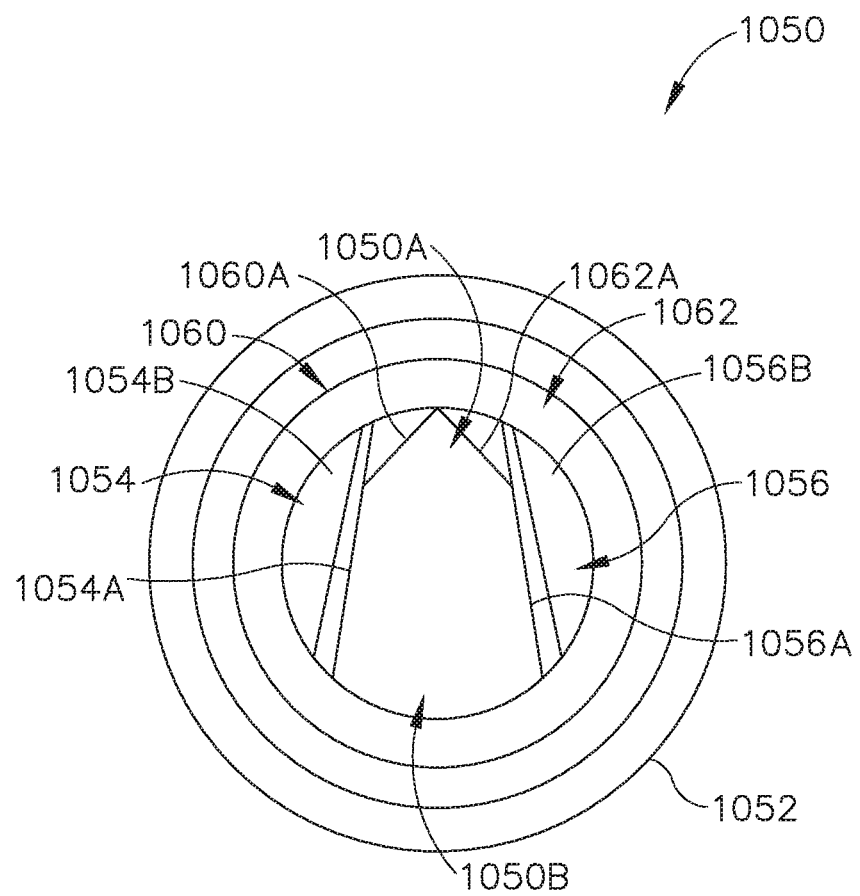
FIG. 46 depicts a front view of the blade tip of FIG. 43.

FIGS. 43-46 show an exemplary alternative blade tip (1050). Blade tip (1050) comprises a circular exterior surface (1052). Blade tip (1050) comprises a substantially straight plan view profile as best seen in FIG. 44 and a substantially straight elevational view profile as best seen in FIG. 45. Blade tip (1050) presents a pair of reliefs (1054, 1056) carved out of a distal end of blade tip (1050) on opposite sides of blade tip (1050). Each relief (1054, 1056) includes a flat surface (1054A, 1056A) and a curved surface (1054B, 1056B). As best seen in FIG. 46, flat surfaces (1054A, 1056A) is angled downwardly and outwardly such that a top portion (1050A) of the distal end of blade tip (1050) is more narrow than a bottom portion (1050B) of the distal end of blade tip (1050). Flat surfaces (1054A, 1056A) extend proximally from a distal tip of blade tip (1050) to curved surfaces (1056A, 1056B). Curved surfaces (1054A, 1056B) provide a transition between flat surfaces (1054A, 1054B) and circular exterior surface (1052).

An arcuate cutout (1058) is formed in a distal end of blade tip (1050). Arcuate cutout (1058) passes through top portion (1050A) of blade tip (1050) from flat surface (1054A) of relief (1054) to flat surface (1056A) such that a portion of each flat surface (1054A, 1056A) presents a cutout in an arcuate fashion when viewed in plan view as shown in FIG. 44. Arcuate cutout (1058) comprises a curved interior surface (1058A). Flat surface (1054A) of relief (1054) transitions to curved interior surface (1058A) of arcuate cutout (1058) along curved edge (1058B). Flat surface (1056A) of relief (1056) transitions to curved interior surface (1058A) of arcuate cutout (1058) along curved edge (1058C). Curved exterior surface (1052) of blade tip (1050) transitions to curved interior surface (1058A) of arcuate cutout (1058) along curved edge (1058D).

Blade tip (1050) further presents a pair of angular cutouts (1060, 1062) carved out of top portion (1050A) at the distal end of blade tip (1050) distal of arcuate cutout (1058) on opposite sides of blade tip (1050). Each angular cutout (1060, 1062) includes a flat surface (1060A, 1062A). As best seen in FIG. 46, flat surfaces (1060A, 1062A) are angled downwardly and outwardly at an angle steeper than flat surfaces (1054A, 1056A) of reliefs (1054, 1056). Flat surfaces (1060A, 1062A) meet and form a sharp edge (1064) at a top of blade tip (1050). Flat surfaces (1060A, 1062A) extend proximally from the distal tip of blade tip (1050) to arcuate cutout (1058). Flat surfaces (1060A, 1062A) transition to curved interior surface (1058A) of arcuate cutout (1058) along curved edges (1058E, 1058F).

Arcuate cutout (1058) may be used to prevent tissue and/or vessels from squeezing out of the distal end of an end effector (not shown) as a clamp arm (not shown) applies clamping force to the tissue and/or vessels. Any surface (1052, 1054, 1056, 1058, 1060, etc.) of blade tip (1050) may be used to seal vessels that do not extend adequately from tissue (e.g., to provide spot sealing or "bleeder touch ups"). The edges of blade tip (1050) (e.g. sharp edge (1064), etc.) may be used to slice through tissue without having to clamp the tissue between the clamp arm and blade tip (1050), in a back-scoring type of movement or otherwise. The sharp tips of blade tip (1050) may also be used to slice through tissue without having to clamp the tissue between the clamp arm and blade tip (1050), in a back-scoring type of movement or otherwise. Blade tip (1050) may also be used to apply monopolar and/or bipolar RF energy to tissue.

Blade tip (1050) may be used with or without a pivoting clamp arm (e.g. clamp arm (44)). Such a clamp arm may pivot toward blade tip (1050) to clamp tissue against top surface (1052), bottom surface (1054), first side surface (1056), and/or second side surface (1058). Blade tip (1050) may thus be oriented in any suitable orientation in relation to a pivoting clamp arm. It should therefore be understood that terms such as "top," "bottom," and "side," should not be read as limiting potential relationships between blade tip (1050) and a pivoting clamp arm.

G. Seventh Exemplary Blade Tip

Figure 42:
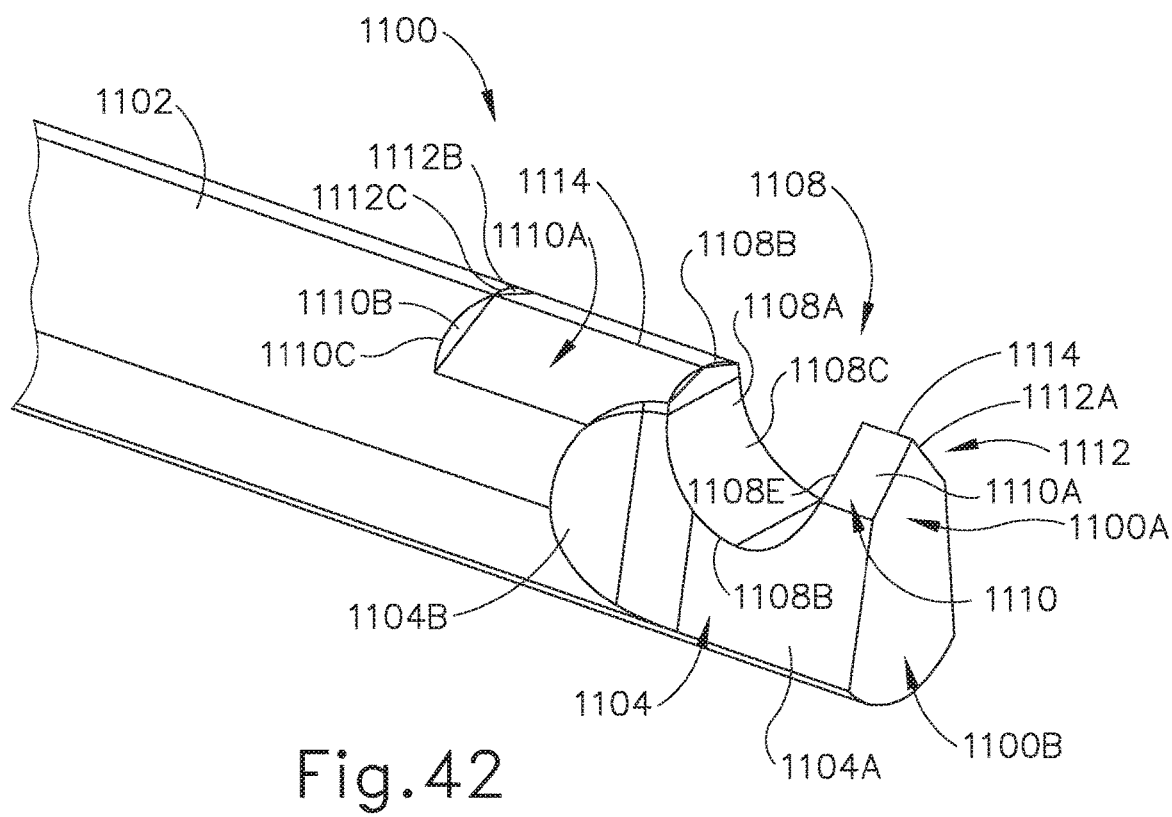
FIG. 42 depicts a perspective view of yet another exemplary alternative blade tip.
Figure 43:
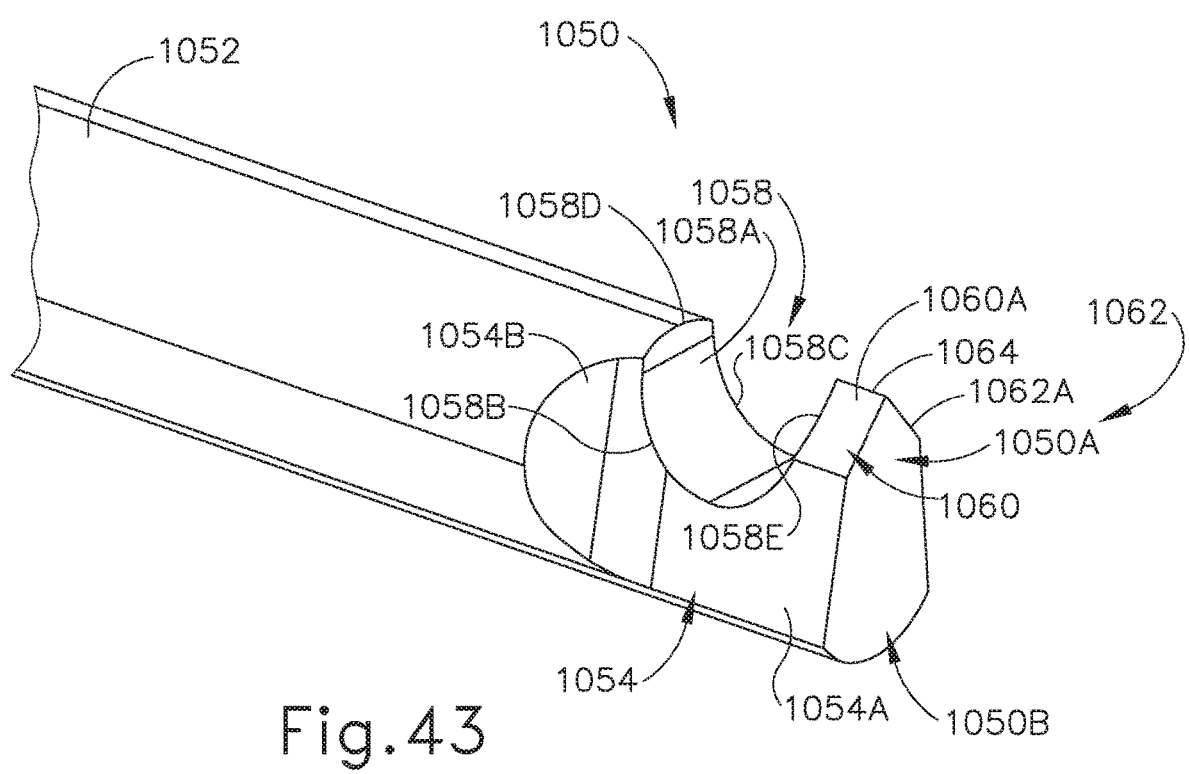
FIG. 43 depicts a perspective view of yet another exemplary alternative blade tip.

FIG. 42 shows an exemplary alternative blade tip (1100). Blade tip (1100) comprises a circular exterior surface (1102). Blade tip (1100) comprises a substantially straight plan view profile and a substantially straight elevational view profile. Blade tip (1100) presents a pair of reliefs (1104, 1106) carved out of a distal end of blade tip (1100) on opposite sides of blade tip (1100). Each relief (1104, 1106) includes a flat surface (1104A, 1106A) and a curved surface (1104B, 1106B). Flat surfaces (1104A, 1106A) is angled downwardly and outwardly such that a top portion (1100A) of the distal end of blade tip (1100) is more narrow than a bottom portion (1100B) of the distal end of blade tip (1100). Flat surfaces (1104A, 1106A) extend proximally from a distal tip of blade tip (1100) to curved surfaces (1106A, 1106B). Curved surfaces (1104A, 1106B) provide a transition between flat surfaces (1104A, 1104B) and circular exterior surface (1102).

An arcuate cutout (1108) is formed in a distal end of blade tip (1100). Arcuate cutout (1108) passes through top portion (1100A) of blade tip (1100) from flat surface (1104A) of relief (1104) to flat surface (1106A) such that a portion of each flat surface (1104A, 1106A) presents a cutout in an arcuate fashion when viewed in plan view. Arcuate cutout (1108) comprises a curved interior surface (1108A). Flat surface (1104A) of relief (1104) transitions to curved interior surface (1108A) of arcuate cutout (1108) along curved edge (1108B). Flat surface (1106A) of relief (1106) transitions to curved interior surface (1108A) of arcuate cutout (1108) along curved edge (1108C). Curved exterior surface (1102) of blade tip (1100) transitions to curved interior surface (1108A) of arcuate cutout (1108) along curved edge (1108D).

Blade tip (1100) further presents a pair of angular cutouts (1110, 1112) carved out of top portion (1100A) at the distal end of blade tip (1100) distal of arcuate cutout (1108) on opposite sides of blade tip (1100). Each angular cutout (1110, 1112) includes a flat surface (1110A, 1112A). Flat surfaces (1110A, 1112A) are angled downwardly and outwardly at an angle steeper than flat surfaces (1104A, 1106A) of reliefs (1104, 1106). Flat surfaces (1110A, 1112A) meet and form a sharp edge (1114) at a top of blade tip (1100). Flat surfaces (1110A, 1112A) extend proximally from the distal tip of blade tip (1100) through arcuate cutout (1108) to a proximal surface (1110B, 1112B). Flat surfaces (1110A, 1112A) transition to curved interior surface (1108A) of arcuate cutout (1108) along curved edges (1108E, 1108F), Proximal surfaces (1110B, 1112B) transition to curved exterior surface (1102) of blade tip (1100) along curved edges (1110C, 1112C).

Arcuate cutout (1108) may be used to prevent tissue and/or vessels from squeezing out of the distal end of an end effector (not shown) as a clamp arm (not shown) applies clamping force to the tissue and/or vessels. Any surface (1102, 1104, 1106, 1108, 1110, etc.) of blade tip (1100) may be used to seal vessels that do not extend adequately from tissue (e.g., to provide spot sealing or "bleeder touch ups"). The edges of blade tip (1100) (e.g. sharp edge (1114), etc.) may be used to slice through tissue without having to clamp the tissue between the clamp arm and blade tip (1100), in a back-scoring type of movement or otherwise. The sharp tips of blade tip (1100) may also be used to slice through tissue without having to clamp the tissue between the clamp arm and blade tip (1100), in a back-scoring type of movement or otherwise. Blade tip (1100) may also be used to apply monopolar and/or bipolar RF energy to tissue.

Blade tip (1100) may be used with or without a pivoting clamp arm (e.g. clamp arm (44)). Such a clamp arm may pivot toward blade tip (1100) to clamp tissue against top surface (1102), bottom surface (1104), first side surface (1106), and/or second side surface (1108). Blade tip (1100) may thus be oriented in any suitable orientation in relation to a pivoting clamp arm. It should therefore be understood that terms such as "top," "bottom," and "side," should not be read as limiting potential relationships between blade tip (1100) and a pivoting clamp arm.

H. Sixth Exerrrplary Blade Tip

Figure 47:
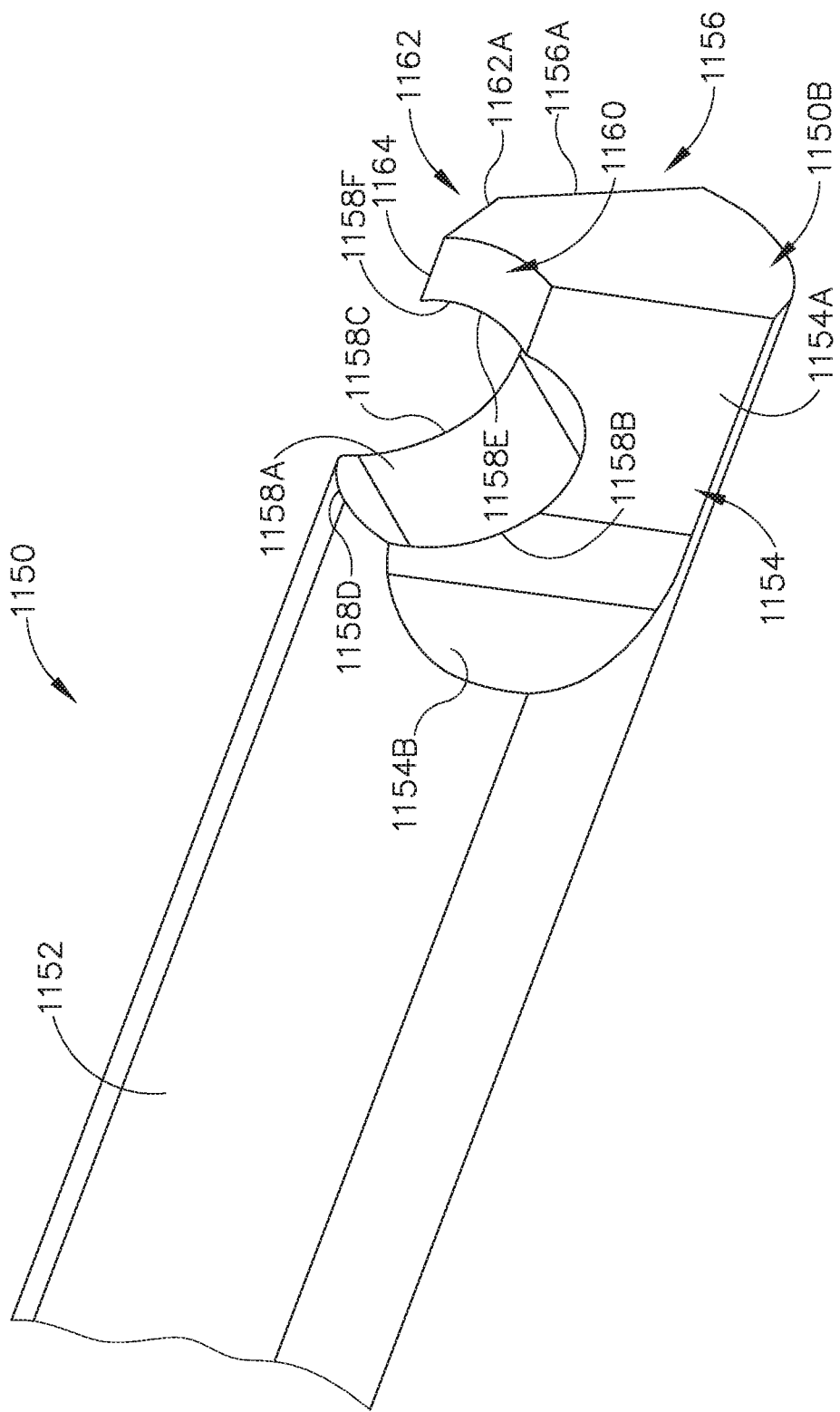
FIG. 47 depicts a perspective view of yet another exemplary alternative blade tip.

FIG. 47 shows an exemplary alternative blade tip (1150). Blade tip (1150) comprises a circular exterior surface (1152). Blade tip (1150) comprises a substantially straight plan view profile and a substantially straight elevational view profile. Blade tip (1150) presents a pair of reliefs (1154, 1156) carved out of a distal end of blade tip (1150) on opposite sides of blade tip (1150). Each relief (1154, 1156) includes a flat surface (1154A, 1156A) and a curved surface (1154B, 1156B). Flat surfaces (1154A, 1156A) is angled downwardly and outwardly such that a top portion (1150A) of the distal end of blade tip (1150) is more narrow than a bottom portion (1150B) of the distal end of blade tip (1150). Flat surfaces (1154A, 1156A) extend proximally from a distal tip of blade tip (1150) to curved surfaces (1156A, 1156B). Curved surfaces (1154A, 1156B) provide a transition between flat surfaces (1154A, 1154B) and circular exterior surface (1152).

An arcuate cutout (1158) is formed in a distal end of blade tip (1150). Arcuate cutout (1158) passes through top portion (1150A) of blade tip (1150) from flat surface (1154A) of relief (1154) to flat surface (1156A) such that a portion of each flat surface (1154A, 1156A) presents a cutout in an arcuate fashion when viewed in plan view. Arcuate cutout (1158) comprises a curved interior surface (1158A). Hat surface (1154A) of relief (1154) transitions to curved interior surface (1158A) of arcuate cutout (1158) along curved edge (1158B). Flat surface (1156A) of relief (1156) transitions to curved interior surface (1158A) of arcuate cutout (1158) along curved edge (1158C). Curved exterior surface (1152) of blade tip (1150) transitions to curved interior surface (1158A) of arcuate cutout (1158) along curved edge (1158D).

Blade tip (1150) further presents an arcuate relief (1160) and an angular cutout (1162) carved out of top portion (1150A) at the distal end of blade tip (1150) distal of arcuate cutout (1158) on opposite sides of blade tip (1150). Arcuate relief (1160) passes proximally from the distal tip of blade tip (1150) to arcuate cutout (1158) thereby defining a curved interior surface (1160A). Angular cutout (1162) includes a flat surface (1162A). Flat surface (1162A) is angled downwardly and outwardly at an angle steeper than flat surface (1156A) of relief (1156), A top portion of arcuate relief (1160) an flat surface (1162A) meet and form a sharp edge (1164) at a top of blade tip (1150). Flat surface (1162A) extends proximally from the distal tip of blade tip (1150) to arcuate cutout (1158). Hat surface (1162A) transitions to curved interior surface (1158A) of arcuate cutout (1158) along curved edge (1158E). Curved interior surface (1160A) transitions to curved interior surface (1158A) of arcuate cutout (1158) along curved edge (1158F).

Arcuate cutout (1158) may be used to prevent tissue and/or vessels from squeezing out of the distal end of an end effector (not shown) as a clamp arm (not shown) applies clamping force to the tissue and/or vessels. Any surface (1152, 1154, 1156, 1158, 1160, etc.) of blade tip (1150) may be used to seal vessels that do not extend adequately from tissue (e.g., to provide spot sealing or "bleeder touch ups"). The edges of blade tip (1150) (e.g. sharp edge (1164), etc.) may be used to slice through tissue without having to clamp the tissue between the clamp arm and blade tip (1150), in a back-scoring type of movement or otherwise. The sharp tips of blade tip (1150) may also be used to slice through tissue without having to clamp the tissue between the clamp arm and blade tip (1150), in a back-scoring type of movement or otherwise. Blade tip (1150) may also be used to apply monopolar and/or bipolar RE energy to tissue.

Blade tip (1150) may be used with or without a pivoting clamp arm (e.g. clamp arm (44)). Such a clamp arm may pivot toward blade tip (1150) to clamp tissue against top surface (1152), bottom surface (1154), first side surface (1156), and/or second side surface (1158). Blade tip (1150) may thus be oriented in any suitable orientation in relation to a pivoting clamp arm. It should therefore be understood that terms such as "top," "bottom," and "side," should not be read as limiting potentialrelationships between blade tip (1150) and a pivoting clamp arm.

VII. Exemplary Curved End Effector

Figure 48:
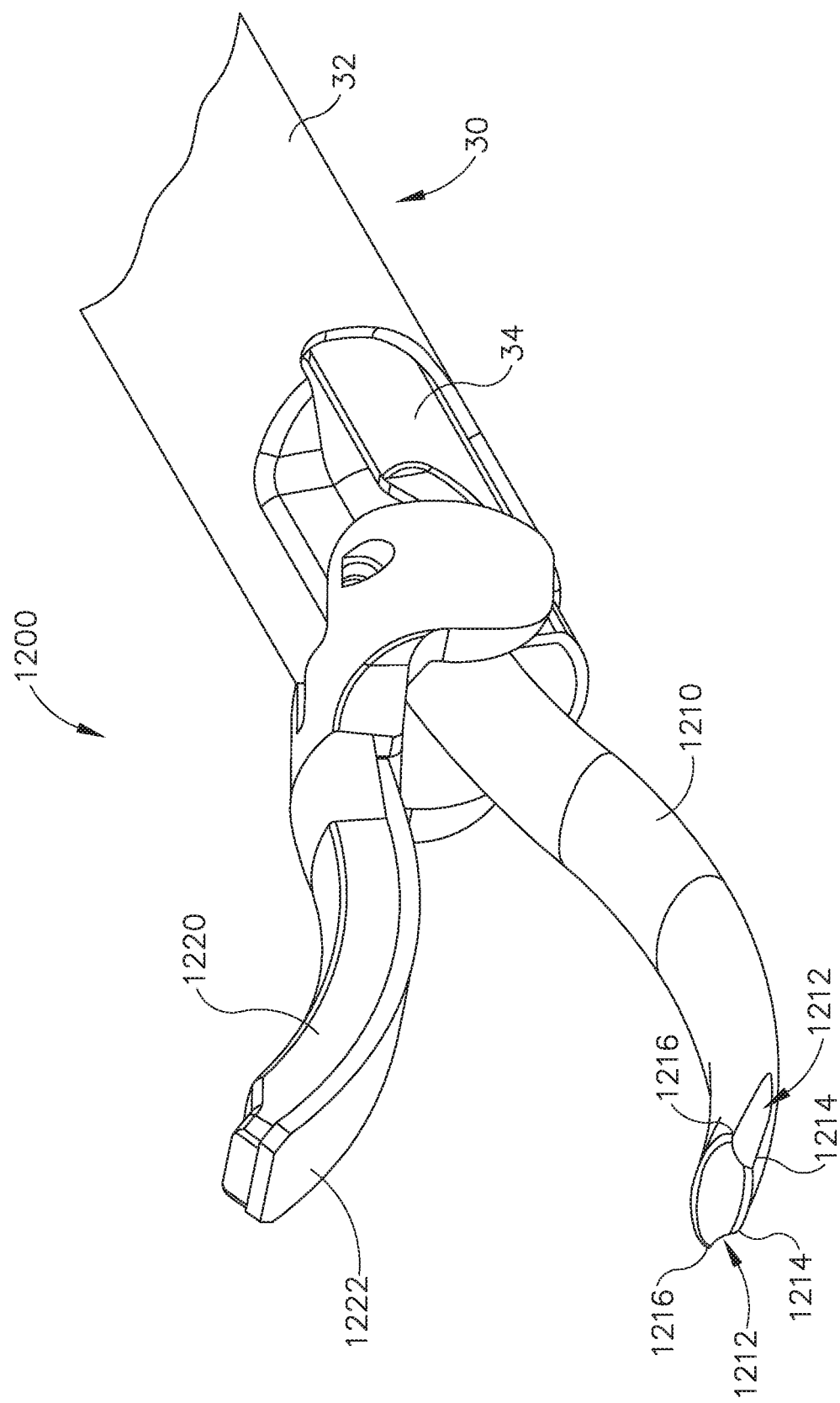
FIG. 48 depicts a perspective view of another exemplary alternative end effector that ay be incorporated into the instrument of FIG. 1.
Figure 49A:
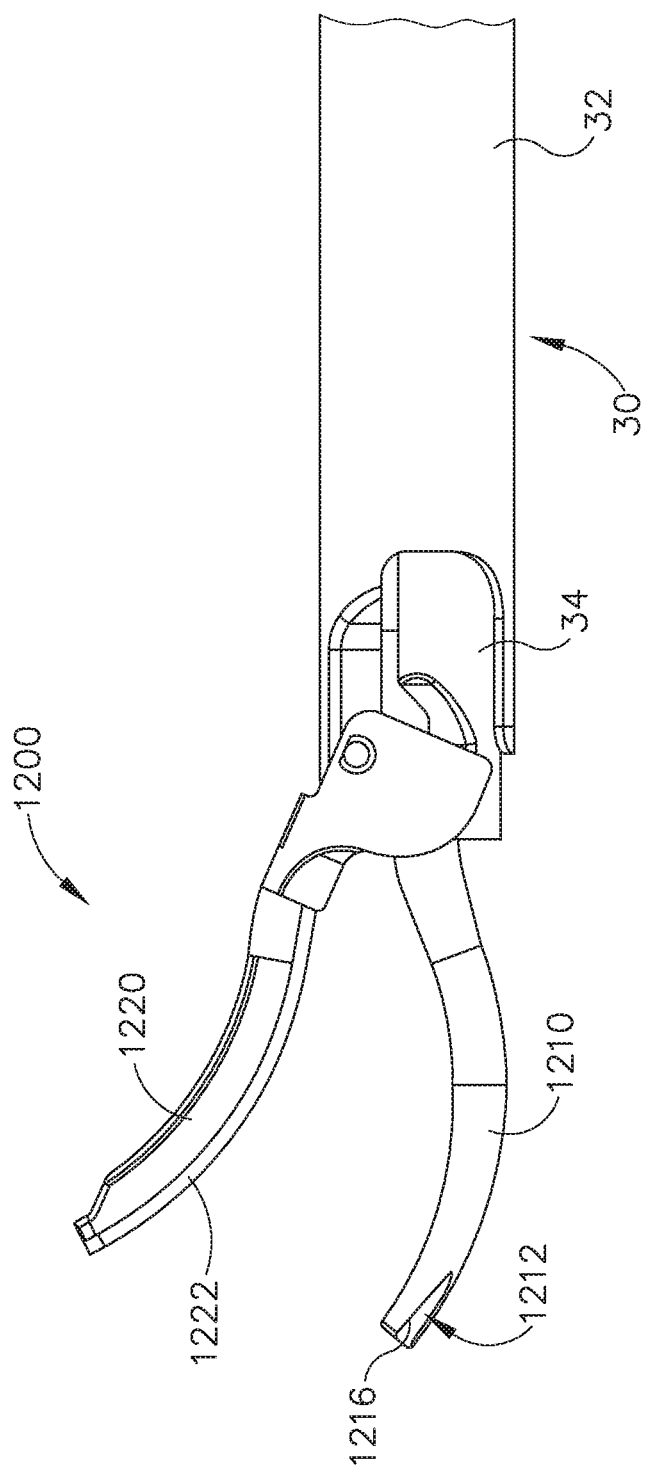
FIG. 49A depicts a side elevational view of the end effector of FIG. 48 in an open configuration.
Figure 49B:
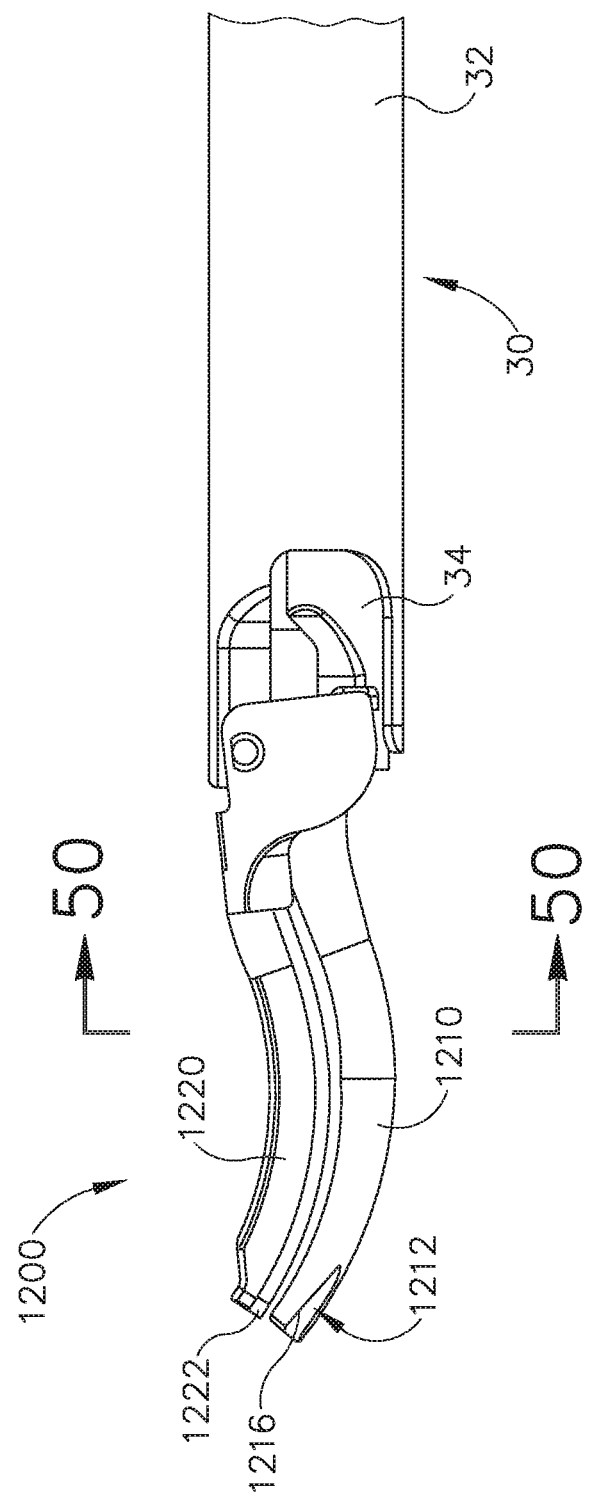
FIG. 49B depicts a side elevational view of the end effector of FIG. 48 in a closed configuration.
Figure 50:
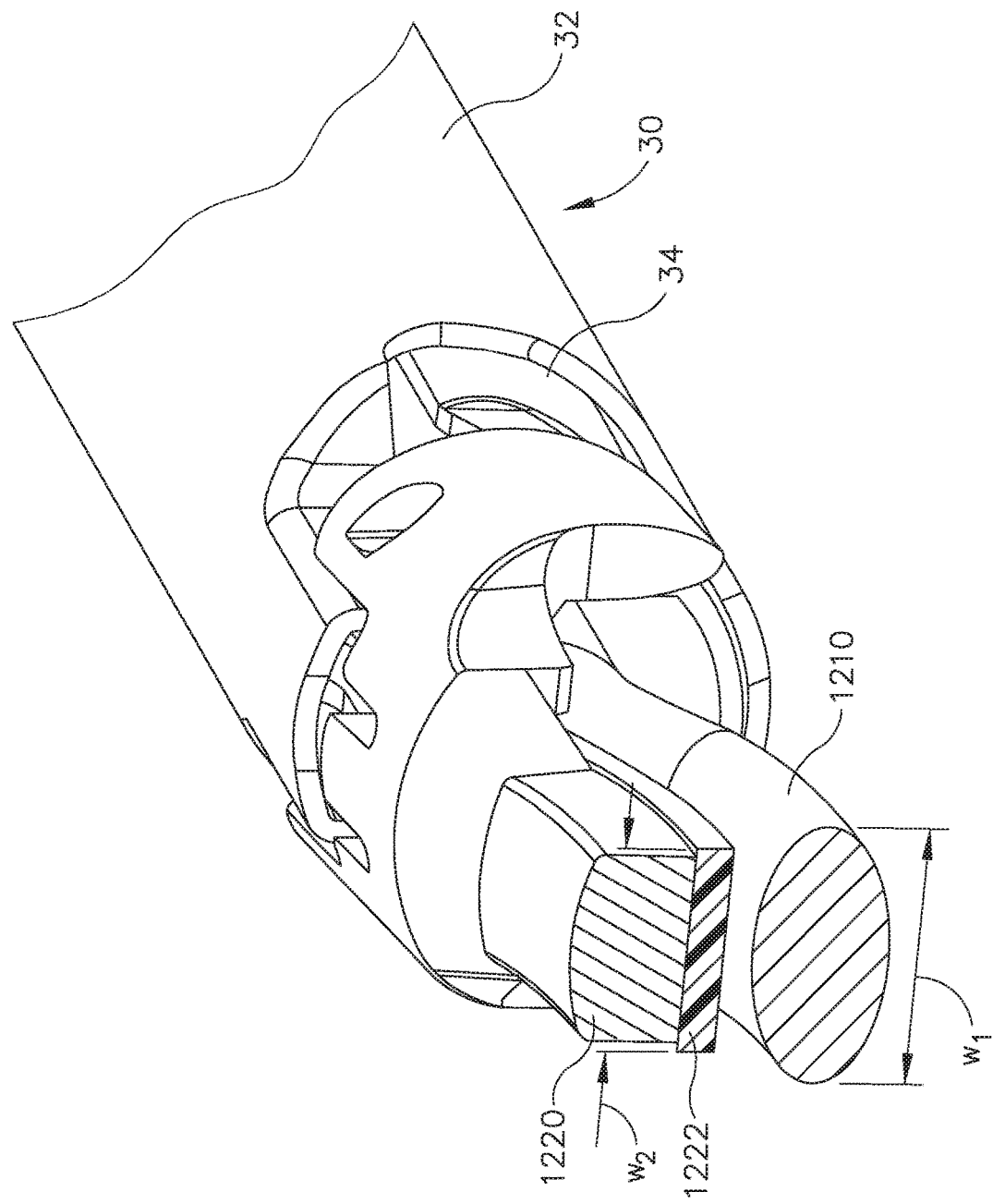
FIG. 50 depicts a cross-sectional perspective view of the end effector of FIG. 48, taken along line 50-50 of FIG. 49B.

FIGS. 48-50 show an exemplary curved end effector (1200) secured to the distal end of shaft assembly (30). It should therefore be understood that end effector (40) may be readily substituted with end effector (1200) of this example. It should also be understood that any other instrument (210, 310, 510, 610) disclosed herein may readily incorporate end effector (1200). End effector (1200) of this example comprises an ultrasonic blade (1210) and a clamp arm (1220). Ultrasonic blade (1210) is operable to vibrate at ultrasonic frequencies like ultrasonic blade (100), etc. The distal end of ultrasonic blade (1210) in this example includes a pair of scallops (1212). Each scallop (1212) is bounded by an interior edge (1214) and an exterior edge (1216). It should be understood that edges (1214, 1216) may be used to perform back scoring with blade (1200). For instance, regardless of the positioning of clamp arm (1220), the operator may drag one or more of edges (1214, 1216) along tissue while applying pressure to the tissue with blade (1200), to thereby cut the tissue with the pressed edge(s) (1214, 126).

Clamp arm (1220) of this example includes a clamp pad (1222). As best seen in FIGS. 49A-49B, clamp arm (1220) is operable to pivotably drive clamp pad (1222) toward and away from blade (1200) based on longitudinal movement of inner tube (34) relative to outer sheath (32). End effector (1200) is thus operable to clamp tissue, applying pressure to tissue interposed between clamp pad (1222) and blade (1210). When blade (1210) is activated during such clamping, blade (1210) may sever and seal the clamped tissue substantially simultaneously. Alternatively (e.g., if less pressure is applied), blade (1210) may simply seal the clamped tissue. As yet another merely illustrative alternative, when blade (1210) is not being ultrasonically activated, end effector (1200) may simply grasp and release tissue without cutting or sealing the tissue.

Clamp arm (1220), clamp pad (1222), and blade (1210) are all curved in the present example. The curvature of clamp arm (1220) and clamp pad (1222) complement the curvature of blade (1210) in this example. In some other versions, the curvatures are non-complementary. In addition or in the alternative, clamp arm (1220), clamp pad (1222), blade (1210), and/or one or more other components may be configured such that the distal end of clamp pad (1222) contacts blade (1210) first during the closure stroke of clamp arm (1220); then the remainder of clamp pad (1222) contacts blade (1210) upon completing the remainder of the closure stroke of clamp arm (1220). In other words, the distal end of clamp pad (1222) may first contact blade (1210) upon completion of a first range of motion of clamp arm (1220) toward blade (1210); and the rest of clamp pad (1220) may subsequently contact blade (1210) upon completion of a second range of motion of clamp arm (1220) toward blade (1210).

It should also be understood that clamp arm (1220), clamp pad (1222), and blade (1210) are all curved along the same plane along which clamp arm (1220) pivots toward and away from blade (1210). In other words, the plane of pivotal motion for clamp arm (1220) is the same as the plane of curvature for clamp arm (1220), clamp pad (1222), and blade (1210). Moreover, as best seen in FIG. 50, the lateral width ($w_1$) of blade (1210) is greater than the lateral width ($w_2$) of clamp pad (1222) in this example. Alternatively, these widths ($w_1$, $w_2$) may be the same; or the lateral width ($w_2$) of clamp pad (1222) may be greater than the lateral width ($w_1$) of blade (1210).

VIII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a shaft assembly longitudinally extending along a central axis and including an acoustic waveguide configured to connect to an ultrasonic transducer and communicate an ultrasonic vibration therealong; and
   (b) an end effector extending distally from the shaft assembly and including:
      (i) a clamp arm configured to pivot in a pivot plane from an open configuration to a closed configuration, wherein the clamp arm includes:
         (A) an arm body formed of a first material and having at least a portion thereof defining a lateral arm width perpendicular to the pivot plane, and
         (B) a clamp pad extending from the arm body in the pivot plane and formed of a second material different than the first material, wherein the clamp pad has at least a portion thereof defining a lateral pad width perpendicular to the pivot plane, and
      (ii) an ultrasonic blade operatively connected to the acoustic waveguide and extending along the pivot plane such that the clamp pad and the lateral pad width thereof is positioned between the arm body and the ultrasonic blade on the pivot plane and further such that the clamp arm is configured to pivot toward the ultrasonic blade, wherein the ultrasonic blade defines a lateral blade width perpendicular to the pivot plane, wherein the lateral blade width is greater than each of the lateral arm width and the lateral pad width, wherein the lateral pad width is greater than the lateral arm width.

2. The surgical instrument of claim 1, wherein the clamp pad has a clamp pad curvature that is curved downward and upward in the pivot plane, wherein the ultrasonic blade has a compression surface facing toward the clamp pad, and wherein the compression surface has a compression surface curvature that is curved downward and upward in the pivot plane.

3. The surgical instrument of claim 2, wherein the clamp pad curvature and the compression surface curvature are complementary to each other.

4. The surgical instrument of claim 1, wherein the central axis intersects the clamp arm in the closed configuration.

5. The surgical instrument of claim 1, wherein the ultrasonic blade has a blade body, and wherein at least a portion of the blade body has an oval cross-section.

6. The surgical instrument of claim 1, wherein the ultrasonic blade further includes:
   (A) a blade body including a first lateral blade portion extending laterally outward further than the clamp arm, and
   (B) a first scallop extending distally through at least a portion of the first lateral blade portion of the blade body to define a first scoring edge that distally extends along the blade body in the first lateral blade portion of the blade body.

7. The surgical instrument of claim 6, wherein the ultrasonic blade further includes:
   (A) the blade body including a second lateral blade portion extending laterally outward further than the clamp arm, wherein the second lateral blade portion is laterally opposite from the first lateral blade portion, and
   (B) a second scallop extending distally through at least a portion of the second lateral blade portion of the blade body to define a second scoring edge that distally extends along the blade body in the second lateral blade portion of the blade body.

8. The surgical instrument of claim 7, wherein the central axis is laterally between the first and second scallops.

9. The surgical instrument of claim 6, wherein the ultrasonic blade further includes:
   (A) a compression surface extending distally along the blade body and facing toward the clamp arm, and
   (B) a scoring surface extending distally along the blade body and facing away from the clamp arm.

10. The surgical instrument of claim 1, wherein the ultrasonic blade has an upper blade portion above the central axis, wherein the ultrasonic blade has a lower blade portion below the central axis, and wherein the lower blade portion of the ultrasonic blade below the central axis is larger than the upper blade portion above the central axis.

11. A surgical instrument, comprising:
    (a) a shaft assembly longitudinally extending along a central axis and including an acoustic waveguide configured to connect to an ultrasonic transducer and communicate an ultrasonic vibration therealong; and
    (b) an end effector extending distally from the shaft assembly and including an ultrasonic blade operatively connected to the acoustic waveguide, wherein the ultrasonic blade includes a proximal blade portion, a distal blade portion, and an intermediate blade portion positioned therebetween, wherein the central axis is offset and spaced from the intermediate blade portion and intersects the distal blade portion, wherein the end effector further includes a clamp arm configured to pivot in a pivot plane, wherein the ultrasonic blade extends along the pivot plane such that the clamp arm is configured to pivot toward the ultrasonic blade, wherein the ultrasonic blade curves distally downward along the pivot plane from the proximal blade portion to the intermediate blade portion, and wherein the ultrasonic blade curves distally upward along the pivot plane from the intermediate blade portion to the distal blade portion, and wherein the intermediate blade portion is below the central axis.

12. The surgical instrument of claim 11, wherein the central axis intersects the proximal blade portion.

13. The surgical instrument of claim 11, wherein the clamp arm includes a proximal arm portion, a distal arm portion, and an intermediate arm portion positioned therebetween, wherein the clamp arm curves distally downward along the pivot plane from the proximal arm portion to the intermediate arm portion, and wherein the clamp arm curves distally upward along the pivot plane from the intermediate arm portion to the distal arm portion.

14. A surgical instrument, comprising:
    (a) a shaft assembly longitudinally extending along a central axis and including an acoustic waveguide configured to connect to an ultrasonic transducer and communicate an ultrasonic vibration therealong; and
    (b) an end effector extending distally from the shaft assembly and including:
       (i) a clamp arm configured to pivot in a pivot plane from an open configuration to a closed configuration, wherein the clamp arm includes:
          (A) an arm body formed of a first material and having at least a portion thereof defining a lateral arm width perpendicular to the pivot plane, and
          (B) a clamp pad extending from the arm body in the pivot plane and formed of a second material different than the first material, wherein the clamp pad has at least a portion thereof defining a lateral pad width perpendicular to the pivot plane, and
(ii) an ultrasonic blade operatively connected to the acoustic waveguide and extending along the pivot plane such that the clamp pad and the lateral pad width thereof is positioned between the arm body and the ultrasonic blade on the pivot plane and further such that the clamp arm is configured to pivot toward the ultrasonic blade, wherein the ultrasonic blade defines a lateral blade width perpendicular to the pivot plane, wherein the lateral blade width is greater than each of the lateral arm width and the lateral pad width, wherein the ultrasonic blade further includes:
(A) a blade body including a first lateral blade portion extending laterally outward further than the clamp arm, and
(B) a first scallop extending distally through at least a portion of the first lateral blade portion of the blade body to define a first scoring edge that distally extends along the blade body in the first lateral blade portion of the blade body.

15. The surgical instrument of claim 14, wherein the ultrasonic blade further includes:
(A) the blade body including a second lateral blade portion extending laterally outward further than the clamp arm, wherein the second lateral blade portion is laterally opposite from the first lateral blade portion, and
(B) a second scallop extending distally through at least a portion of the second lateral blade portion of the blade body to define a second scoring edge that distally extends along the blade body in the second lateral blade portion of the blade body.

16. The surgical instrument of claim 15, wherein the central axis is laterally between the first and second scallops.

17. The surgical instrument of claim 14, wherein the ultrasonic blade further includes:
(A) a compression surface extending distally along the blade body and facing toward the clamp arm, and
(B) a scoring surface extending distally along the blade body and facing away from the clamp arm.

* * * * *